(12) United States Patent
Reyes et al.

(10) Patent No.: US 9,220,774 B2
(45) Date of Patent: *Dec. 29, 2015

(54) METHODS OF TREATING CANCER BY ADMINISTERING ANTI-GPR49 ANTIBODIES

(71) Applicant: Bionomics Inc., San Diego, CA (US)

(72) Inventors: Christopher L. Reyes, San Diego, CA (US); Peter Chu, San Diego, CA (US); Xiangyang Tan, Tewksbury, MA (US); Weixing Yang, Newton, MA (US); Christilyn Graff, Cambridge, MA (US)

(73) Assignee: Bionomics Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/355,189

(22) PCT Filed: Oct. 31, 2012

(86) PCT No.: PCT/US2012/062866
§ 371 (c)(1),
(2) Date: Apr. 29, 2014

(87) PCT Pub. No.: WO2013/067057
PCT Pub. Date: May 10, 2013

(65) Prior Publication Data
US 2014/0302054 A1    Oct. 9, 2014

Related U.S. Application Data

(60) Provisional application No. 61/554,435, filed on Nov. 1, 2011.

(51) Int. Cl.
*A61K 39/395*    (2006.01)
*C07K 16/28*    (2006.01)

(52) U.S. Cl.
CPC ........... *A61K 39/39558* (2013.01); *C07K 16/28* (2013.01); *C07K 2317/33* (2013.01); *C07K 2317/92* (2013.01)

(58) Field of Classification Search
CPC . C07K 16/28; C07K 2317/33; C07K 2317/92
See application file for complete search history.

(56) References Cited

U.S. PATENT DOCUMENTS

| | | | |
|---|---|---|---|
| 4,444,887 A | 4/1984 | Hoffmann |
| 4,474,893 A | 10/1984 | Reading |
| 4,676,980 A | 6/1987 | Segal et al. |
| 4,714,681 A | 12/1987 | Reading |
| 4,716,111 A | 12/1987 | Osband et al. |
| 4,741,900 A | 5/1988 | Alvarez et al. |
| 4,816,397 A | 3/1989 | Boss et al. |
| 4,816,567 A | 3/1989 | Cabilly et al. |
| 4,925,648 A | 5/1990 | Hansen et al. |
| 4,946,778 A | 8/1990 | Ladner et al. |
| 5,112,946 A | 5/1992 | Maione |
| 5,122,464 A | 6/1992 | Wilson et al. |
| 5,223,409 A | 6/1993 | Ladner et al. |
| 5,225,539 A | 7/1993 | Winter |
| 5,258,498 A | 11/1993 | Huston et al. |
| 5,314,995 A | 5/1994 | Fell et al. |
| 5,336,603 A | 8/1994 | Capon et al. |
| 5,349,053 A | 9/1994 | Landolfi |
| 5,359,046 A | 10/1994 | Capon et al. |
| 5,403,484 A | 4/1995 | Ladner et al. |
| 5,413,923 A | 5/1995 | Kucherlapati et al. |
| 5,427,908 A | 6/1995 | Dower et al. |
| 5,447,851 A | 9/1995 | Beutler et al. |
| 5,474,981 A | 12/1995 | Leder et al. |
| 5,516,637 A | 5/1996 | Huang et al. |
| 5,530,101 A | 6/1996 | Queen et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,569,825 A | 10/1996 | Lonberg et al. |
| 5,571,698 A | 11/1996 | Ladner et al. |
| 5,573,920 A | 11/1996 | Randle |
| 5,580,717 A | 12/1996 | Dower et al. |
| 5,585,089 A | 12/1996 | Queen et al. |
| 5,591,669 A | 1/1997 | Krimpenfort et al. |
| 5,601,819 A | 2/1997 | Wong et al. |
| 5,605,793 A | 2/1997 | Stemmer |
| 5,612,205 A | 3/1997 | Kay et al. |
| 5,622,929 A | 4/1997 | Willner et al. |
| 5,624,821 A | 4/1997 | Winter et al. |
| 5,633,425 A | 5/1997 | Lonberg et al. |

(Continued)

FOREIGN PATENT DOCUMENTS

| | | |
|---|---|---|
| EP | 0239400 | 9/1987 |
| EP | 0367166 | 5/1990 |

(Continued)

OTHER PUBLICATIONS

Carmon KS, et al. PNAS 108(28):11452-11457, Jul. 12, 2011. Available online at—doi/10.1073/pnas.1106083108.*

Becker, L. et al., Immunostaining of Lgr5, an intestinal stem cell marker, in normal and premalignant human gastrointestinal tissue, ScientificWorldJournal. Nov. 23, 2008;8:1168-76.

Fan, XS, et al, Expression of Lgr5 in human colorectal carcinogenesis and its potential correlation with beta-catenin, Int J Colorectal Dis. May 2010;25(5):583-90.

(Continued)

*Primary Examiner* — Robert Landsman
(74) *Attorney, Agent, or Firm* — Knobbe, Martens, Olson & Bear LLP

(57) ABSTRACT

Described herein are antibodies against GPR49 and uses of such antibodies. Various aspects relate to monoclonal, humanized, or fully human antibodies against GPR49, hybridomas or other cell lines expressing such antibodies, nucleic acids and vectors comprising nucleic acids encoding for such antibodies.

22 Claims, 21 Drawing Sheets

(56) References Cited

U.S. PATENT DOCUMENTS

| | | | |
|---|---|---|---|
| 5,643,763 A | 7/1997 | Dunn et al. |
| 5,648,260 A | 7/1997 | Winter et al. |
| 5,658,727 A | 8/1997 | Barbas et al. |
| 5,658,759 A | 8/1997 | Bebbington |
| 5,661,016 A | 8/1997 | Lonberg et al. |
| 5,677,425 A | 10/1997 | Bodmer et al. |
| 5,698,426 A | 12/1997 | Huse |
| 5,714,350 A | 2/1998 | Co et al. |
| 5,721,367 A | 2/1998 | Kay et al. |
| 5,733,743 A | 3/1998 | Johnson et al. |
| 5,750,753 A | 5/1998 | Kimae et al. |
| 5,770,429 A | 6/1998 | Lonberg et al. |
| 5,780,225 A | 7/1998 | Wigler et al. |
| 5,789,208 A | 8/1998 | Sharon |
| 5,789,215 A | 8/1998 | Berns et al. |
| 5,789,650 A | 8/1998 | Lonberg et al. |
| 5,807,715 A | 9/1998 | Morrison et al. |
| 5,811,238 A | 9/1998 | Stemmer et al. |
| 5,814,318 A | 9/1998 | Lonberg et al. |
| 5,821,047 A | 10/1998 | Garrard et al. |
| 5,827,739 A | 10/1998 | Wilson et al. |
| 5,830,721 A | 11/1998 | Stemmer et al. |
| 5,834,252 A | 11/1998 | Stemmer et al. |
| 5,837,458 A | 11/1998 | Minshull et al. |
| 5,869,046 A | 2/1999 | Presta et al. |
| 5,874,299 A | 2/1999 | Lonberg et al. |
| 5,877,397 A | 3/1999 | Lonberg et al. |
| 5,879,936 A | 3/1999 | Bebbington et al. |
| 5,885,573 A | 3/1999 | Bluestone et al. |
| 5,885,793 A | 3/1999 | Griffiths et al. |
| 5,916,771 A | 6/1999 | Hori et al. |
| 5,939,598 A | 8/1999 | Kucherlapati et al. |
| 5,969,108 A | 10/1999 | McCafferty et al. |
| 5,981,175 A | 11/1999 | Loring et al. |
| 5,981,216 A | 11/1999 | Kenten et al. |
| 6,023,010 A | 2/2000 | Krimpenfort et al. |
| 6,121,022 A | 9/2000 | Presta et al. |
| 6,165,745 A | 12/2000 | Ward et al. |
| 6,194,551 B1 | 2/2001 | Idusogie et al. |
| 6,255,458 B1 | 7/2001 | Lonberg et al. |
| 6,277,375 B1 | 8/2001 | Ward |
| 6,335,163 B1 | 1/2002 | Sharon |
| 6,350,861 B1 | 2/2002 | Co et al. |
| 6,737,056 B1 | 5/2004 | Presta et al. |
| 6,821,505 B2 | 11/2004 | Ward |
| 8,680,243 B2* | 3/2014 | Funahashi | 530/388.22 |
| 2003/0153043 A1 | 8/2003 | Carr et al. |
| 2003/0190311 A1 | 10/2003 | Dall'Acqua et al. |
| 2004/0002587 A1 | 1/2004 | Watkins et al. |
| 2014/0147383 A1* | 5/2014 | Funahashi | 424/1.49 |
| 2014/0256041 A1 | 9/2014 | Reyes et al. |
| 2014/0302049 A1 | 10/2014 | Reyes et al. |
| 2015/0037324 A1 | 2/2015 | Reyes et al. |

FOREIGN PATENT DOCUMENTS

| | | |
|---|---|---|
| EP | 0396387 | 11/1990 |
| EP | 0413622 | 2/1991 |
| EP | 0439095 | 7/1991 |
| EP | 0519596 | 12/1992 |
| EP | 0592106 | 4/1994 |
| EP | 0773288 | 5/1997 |
| EP | 0843961 | 5/1998 |
| EP | 1176195 | 1/2002 |
| EP | 2216344 | 8/2010 |
| WO | WO 86/05807 | 10/1986 |
| WO | WO 88/07089 | 9/1988 |
| WO | WO 89/01036 | 2/1989 |
| WO | WO 89/12624 | 12/1989 |
| WO | WO 90/02809 | 3/1990 |
| WO | WO 91/00360 | 1/1991 |
| WO | WO 91/06570 | 5/1991 |
| WO | WO 91/09967 | 7/1991 |
| WO | WO 91/10737 | 7/1991 |
| WO | WO 91/10741 | 7/1991 |
| WO | WO 91/14438 | 10/1991 |
| WO | WO 92/01047 | 1/1992 |
| WO | WO 92/03918 | 3/1992 |
| WO | WO 92/05793 | 4/1992 |
| WO | WO 92/08495 | 5/1992 |
| WO | WO 92/08802 | 5/1992 |
| WO | WO 92/18619 | 10/1992 |
| WO | WO 92/22324 | 12/1992 |
| WO | WO 92/22645 | 12/1992 |
| WO | WO 92/22647 | 12/1992 |
| WO | WO 92/22670 | 12/1992 |
| WO | WO 93/11236 | 6/1993 |
| WO | WO 93/12227 | 6/1993 |
| WO | WO 93/15199 | 8/1993 |
| WO | WO 93/15200 | 8/1993 |
| WO | WO 93/17715 | 9/1993 |
| WO | WO 93/21232 | 10/1993 |
| WO | WO 94/00569 | 1/1994 |
| WO | WO 94/25585 | 11/1994 |
| WO | WO 95/15982 | 6/1995 |
| WO | WO 95/20401 | 8/1995 |
| WO | WO 96/04388 | 2/1996 |
| WO | WO 96/14436 | 5/1996 |
| WO | WO 96/33735 | 10/1996 |
| WO | WO 96/34096 | 10/1996 |
| WO | WO 97/13852 | 4/1997 |
| WO | WO 97/34631 | 9/1997 |
| WO | WO 98/16654 | 4/1998 |
| WO | WO 98/24884 | 6/1998 |
| WO | WO 98/24893 | 6/1998 |
| WO | WO 98/46645 | 10/1998 |
| WO | WO 98/50433 | 11/1998 |
| WO | WO 99/54342 | 10/1999 |
| WO | WO 99/58572 | 11/1999 |
| WO | WO 00/42072 | 7/2000 |
| WO | WO 02/060919 | 8/2002 |
| WO | WO 03/035835 | 5/2003 |
| WO | WO 03/075957 | 9/2003 |
| WO | WO 2004/009618 | 1/2004 |
| WO | WO 2004/029207 | 4/2004 |
| WO | WO 2005/089285 | 9/2005 |
| WO | WO 2009/005809 | 1/2009 |
| WO | WO 2009/005809 A2 | 1/2009 |
| WO | WO 2010/016766 | 2/2010 |

OTHER PUBLICATIONS

McClanahan, T. et al, Identification of overexpression of orphan G protein-coupled receptor GPR49 in human colon and ovarian primary tumors, Cancer Biol Ther. Apr. 2006;5(4):419-26. Epub Apr. 19, 2006.

Sasaki, Y. et al, Establishment of a novel monoclonal antibody against LGR5; Biochem Biophys Res Commun. Apr. 9, 2010;394(3):498-502.

Walker, F. et al., LGR5 is a negative regulator of tumourigenicity, antagonizes Wnt signalling and regulates cell adhesion in colorectal cancer cell lines, PLoS One. 2011;6(7):e22733.

Yamamoto, Y. et al., Overexpression of orphan G-protein-coupled receptor, Gpr49, in human hepatocellular carcinomas with beta-catenin mutations, Hepatology. Mar. 2003;37(3):528-33.

International Search Report dated Feb. 4, 2013 received in International Application No. PCT/US2012/062866.

Armour, K.L. et al., Recombinant human IgG molecules lacking Fcgamma receptor I binding and monocyte triggering activities, Eur J Immunol 1999, 29:2613-2624.

Ashkenazi A. et al., Protection against endotoxic shock by a tumor necrosis factor receptor immunoadhesin. PNAS USA, Dec. 1991; 88:10535-10539.

Ausubel F.M. et al., Current Protocols in Molecular Biology, John Wiley & Sons, Inc. TOC, pp. 15.

Barker N. et al., Identification of stem cells in small intestine and colon by marker gene *Lgr5*, Nature Oct. 2007;449:1003-1008.

Better, M. et al., *Escherichia coli* Secretion of an Active Chimeric Antibody Fragment, Science May 1988; 240:1041-1043.

Bradley T.R. et al., The Growth of Mouse Bone Marrow Cells in Vitro. Aust J Exp Biol Med Sci. 1966; 44:287-300.

(56) References Cited

OTHER PUBLICATIONS

Clackson T. et al., Making antibody fragments using phage display libraries. Nature Aug. 1991; 352:624-628.
Crouse G.F. et al., Expression and Amplification of Engineered Mouse Dihydrofolate Reductase Minigenes. Mol Cell Biol. Feb. 1983; 3(2):257-266.
De Lau, W. et al., Lgr5 homologues associate with Wnt receptors and mediate R-spondin signaling, Nature. Jul. 4, 2011;476(7360):293-7-1.
Dontu G. et al., In vitro propagation and transcriptional profiling of human mammary stem/progenitor cells. Genes Dev. May 2003; 17(10):1253-1270.
Dracopoli N.C. et al., [Eds.] Current Protocols in Human Genetics, John Wiley & Sons, N.Y. 1994; Chapters 12 and 13; pp. 390.
Garnett M.C., Targeted drug conjugates: Principles and Progress. Adv Drug Deliv Rev. 2001; 53(2):171-216.
Gentz R. et al., Bioassay for trans-activation using purified human immunodeficiency virus *tat*-encoded protein: Trans-activation requires mRNA synthesis. PNAS USA. Feb. 1989; 86:821-824.
Gillies S.D. et al., Antibody-targeted interleukin 2 stimulates T-cell killing of autologous tumor cells. PNAS USA. Feb. 1992; 89:1428-1432.
Green L.L. et al., Regulation of B Cell Development by Variable Gene Complexity in Mice Reconstituted with Human Immunoglobulin Yeast Artifical Chromosomes. J Exp Med. Aug. 1998; 188(3):483-495.
Greenspan N.S. et al., Idiotypes: Structure and Immunogenicity. FASEB J. 1989;7(5):437-444.
Hansson L.O. et al., Evolution of Differential Substrate Specificities in Mu Class Glutathione Transferases Probed by DNA Shuffling. J Mol Biol. 1999; 287:265-276.
Harlow, E. et al., Antibodies: A Laboratory Manual, Cold Spring Harbor Laboratory 1988; 2nd Ed., TOC 9 pages.
Hutchins, J.T. et al., Improved biodistribution, tumor targeting, and reduced immunogenicity in mice with a gamma 4 variant of Campath-1H, Proc Natl Acad Sci. USA Dec. 1995; 92:11980-11984.
Idusogie, E.E. et al., Mapping of the C1q Binding Site on Rituxan, A Chimeric Antibody with a Human IgG1 Fc, J Immunol. 2000, 164:4178-4184.
Idusogie, E.E. et al., Engineered Antibodies with Increased Activity to Recruit Complement, J Immunol. 2001,166:2571-2575.
Inouye S. et al., Up-promoter mutations in the *Ipp* gene of *Escherichia coli*. Nuc Acids Res. 1985;13(9):3101-3110.
Jones P.T. et al., Replacing the complementarity—determining regions in a human antibody with those from a mouse. Nature May 1986; 321:522-525.
Karlin S. et al., Applications and statistics for multiple high-scoring segments in molecular sequences. PNAS USA. Jun. 1993;90:5873-5877.
Kleist B. et al., Expression of the adult intestinal stem cell marker Lgr5 in the metastatic cascade of colorectal cancer, Int J Clin Exp Pathol. 2011; 4(4):327-335.
Kobayashi, S. et al., Lgr5-positive colon cancer stem cells interconvert with drug-resistant LGR5-negative cells and are capable of tumor reconstitution, Stem Cells. Dec. 2012;30(12):2631-44.
Köhler G., Immunoglobulin chain loss in hybridoma lines. PNAS USA, Apr. 1980; 77(4):2197-2199.
Kostelny S.A. et al., Formation of a bispecific antibody by the use of leucine zippers. J Immunol. 1992; 148:1547-1553.
Liu et al., Hedgehog Signaling and Bmi-1 Regulate Self-renewal of Normal and Malignant Human Mammary Stem Cells. Can Res. Jun. 2006; 66(12):6063-6071.
Logan J. et al., Adenovirus tripartite leader sequence enhances translation of mRNAs late after infection. PNAS, USA Jun. 1984; 81:3655-3659.
Lonberg N. et al., Antigen-specific human antibodies from mice comprising four distinct genetic modifications. Nature 1994; 368:856-859.

Lorenzo M. et al. "PCR-Based Method for the Introduction of Mutations in Genes Cloned and Expressed in Vaccinia Virus", Biotechniques 1998; 24(2): 308-313.
Lund, J. et al., Oligosaccharide-protein interactions in IgG can modulate recognition by Fcgamma receptors, FASEB 1995; J 9:115-119.
McCafferty J. et al., Phage antibodies: filamentous phage displaying antibody variable domains. Nature Dec. 1990;348:552-554.
Mendez M.J. et al., Functional transplant of megabase human immunoglobulin loci recapitulates human antibody response in mice. Nat Gene. 1997;15:146-156.
Morrison S.L., Transfectomas Provide Novel Chimeric Antibodies, Science 1985; 229:1202-1207.
Mulligan R.C. et al., Selection for animal cells that express the *Escherichia coli* gene coding for xanthine-guanine phosphoribosyltransferase. PNAS USA Apr. 1981 78(4):2072-2076.
NCBI Accession No. NM_003667.2; *Homo sapiens* leucine-rich repeat containing G protein-coupled recetor 5 (LGR5), mRNA; Mar. 3, 2013, 9 pages.
O'Hare K. et al., Transformation of mouse fibroblasts to methotrexate resistance by a recombinant plasmid expressing a prokaryotic dihydrofolate reductase. PNAS USA, Mar. 1981; 78(3):1527-1531.
Oi V.T. et al., Chimeric Antibodies, BioTechniques Mar. 1986; 4(2):214-221.
Padlan, E.A., A possible procedure for reducing the immunogenicity of antibody variable domains while preserving their ligand-binding properties. Mol Immunol. 1991; 28(4/5):489-498.
Patten et al., Applications of DNA shuffling to pharmaceuticals and vaccines, 1997, Curr Opin Biotechnol. Dec. 1997; 8(6):724-733.
Presta L.G. et al., Engineering therapeutic antibodies for improved function, Biochem Soc Trans. Aug. 2002; 30(4):487-490.
Proudfoot N.J., Transcriptional interference and termination between duplicated alpha-globin gene constructs suggests a novel mechanism for gene regulation. Nature Aug. 1986; 322:562-565.
Reddy, M.P. et al., Elimination of Fc Receptor-Dependent Effector Functions of a Modified IgG4 Monoclonal Antibody to Human CD4, J Immunol. 2000, 164:1925-1933.
Reese M.G. et al., Improved Splice Site Detection in Genie. J Comp Biol. 1997; 4(3):311-323.
Riechmann L. et al., Reshaping human antibodies for therapy. Nature 1988; 332:323-327.
Roguska M.A. et al., Humanization of murine monoclonal antibodies through variable domain resurfacing. PNAS 1994; 91:969-973.
Rüther U. et al., Easy Identification of Cdna clones. EMBO J. 1983;2(10):1791-1983.
Santerre R.F. et al., Expression of prokaryotic genes for hygromycin B and G418 resistance as dominant-selection markers in mouse L cells. Gene 1984; 30:147-156.
Schäffer A.A. et al., Improving the accuracy of PSI-BLAST protein database searches with composition-based statistics and other refinements, Nucl Acids Res. 2001; 29(14):2994-3005.
Shields, R.L. et al., High Resolution Mapping of the Binding Site on Human IgG1 for FcgammaRI, FcgammaRII, FcgammaRIII, and FcRn and design of IgG1 Variants with Improved Binding to the FcgammaR, J Biol Chem. 2001 Mr; 276(():6591-6604.
Shields, R. L. et al., Lack of Fucose on Human IgG1 *N*-linked Oligosaccharide Improves Binding to Human FcgammaRIII and Antibody-dependent Cellular Toxicity, J Biol Chem. Jul. 2002; 277(3):26733-26740.
Shu L. et al., Secretion of a single-gene-encoded immunoglobuln from myeloma cells, PNAS Sep. 1993; 90(17):7995-7999.
Singh S.K. et al., Identification of human brain tumor initiating cells Nature. Nov. 2004; 432(7015):396-401.
Skerra A. et al., Assembly of a Functional Immunoglobulin Fv Fragment in *Escherichia coli*, Science 1988; 240:1038-1040.
Szybalska et al., Genetics of Human Cell Lines, IV. DNA-mediated Heritable Transformation of a Biochemical Trait. Proc. Natl. Acad. Sci. USA, 1962; 48:2026-2034.
Studnicka G.M. et al., Human-engineered monoclonal antibodies retain full specific binding activity by preserving non-CDR complementarity-modulating residues. Prot Engineer. 1994; 7(6):805-814.

(56) References Cited

OTHER PUBLICATIONS

Tutt, A. et al., Trispecific F(ab')3 derivatives that use cooperative signaling via the TCR/CD3 complex and CD2 to activate and redirect resting cytotoxic T cells, J Immunol. Jul. 1, 1991:147(1):60-9.
Van Heeke G. et al., Expression of Human Asparagine Synthetase in *Escherichia coli*. J Biol Chem. Apr. 1989;264(10):5503-5509.
Vie H. et al., Human Fusion Proteins between Interleukin 2 and IgM Heavy Chain are Cytotoxic for Cells Expressing the Interleukin 2 Receptor. PNAS USA. Dec. 1992; 89(23):11337-11341.
Wigler M. et al., Transfer of Purified Herpes Virus Thymidine Kinase Gene to Cultured Mouse Cells. Cell May 1977;11:223-232.
Wigler M. et al., Transformation of mammalian cells with an amplifiable dominant-acting gene. PNAS USA. Jun. 1980;77(6):3567-3570.

* cited by examiner

*Fig. 8A*
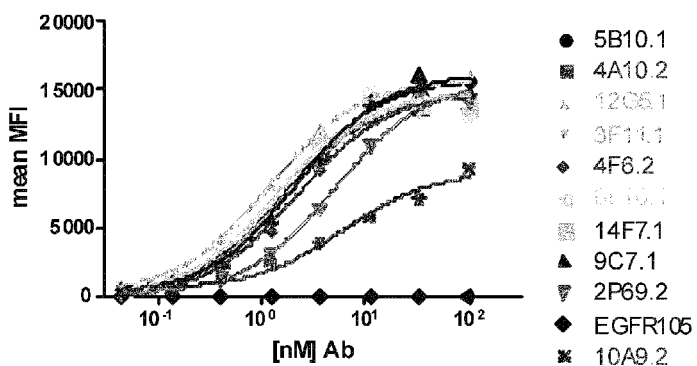
*Fig. 8B*
| | 5B10.1 | 4A10.2 | 12G5.1 | 3F11.1 | 4F6.2 | 6E10.1 | 14F7.1 | 9C7.1 | 2P69.2 | EGFR105 | 10A9.2 |
|---|---|---|---|---|---|---|---|---|---|---|---|
| EC50 | 1.941 | 1.716 | 1.210 | 1.750 | 2.206 | 1.322 | 1.476 | 2.205 | 5.116 | 0.2681 | 6.218 |
*Fig. 8C*
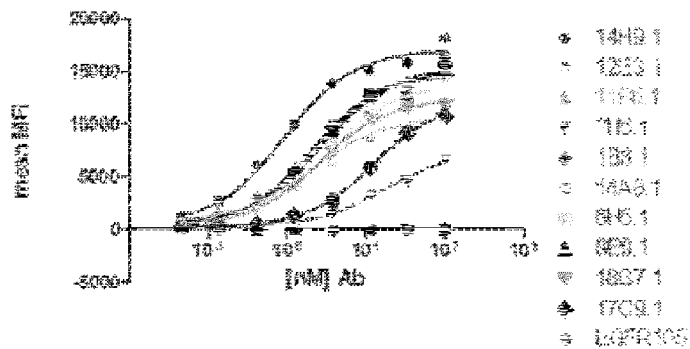
*Fig. 8D*
| | 14H9.1 | 12E3.1 | 11F6.1 | 2H5.1 | 1B8.1 | 14A8.1 | 6H5.1 | 8E9.1 | 18G7.1 | 17C9.1 |
|---|---|---|---|---|---|---|---|---|---|---|
| EC50 | 0.9161 | 2.632 | 1.853 | 17.48 | 2.239 | 2.143 | 2.991 | 2.170 | 2.460 | 12.46 |

Fig. 9A
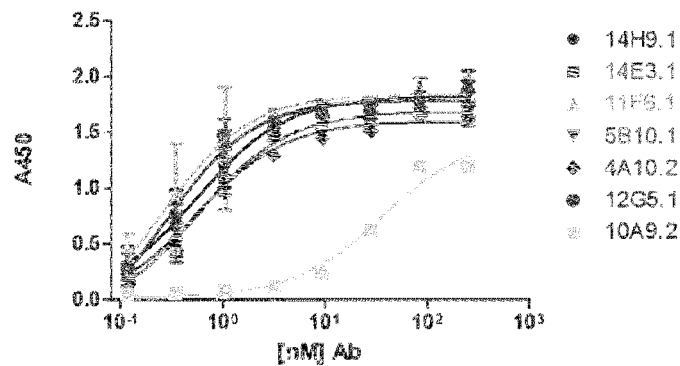
Fig. 9B
|  | 14H9.1 | 14E3.1 | 11F6.1 | 5B10.1 | 4A10.2 | 12G5.1 | 10A9.2 |
|---|---|---|---|---|---|---|---|
| EC50 | 0.5523 | 0.5587 | 0.2429 | 0.2737 | 0.5311 | 0.2565 | 35.22 |
Fig. 9C
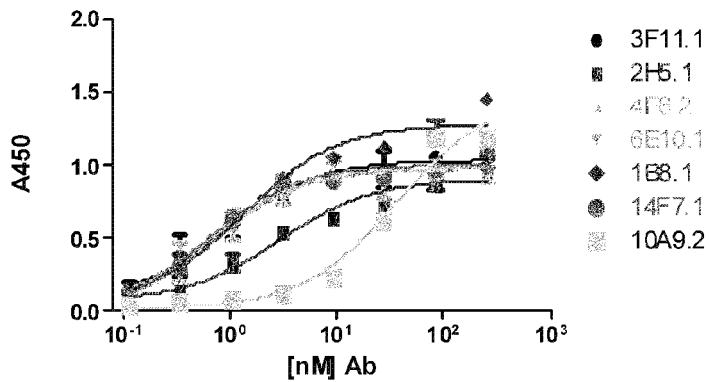
Fig. 9D
|  | 3F11.1 | 2H5.1 | 4F6.2 | 6E10.1 | 1B8.1 | 14F7.1 | 10A9.2 |
|---|---|---|---|---|---|---|---|
| EC50 | 0.8837 | 2.866 | 0.6506 | 0.6577 | 1.335 | 0.5695 | 35.22 |

*Fig. 9E*
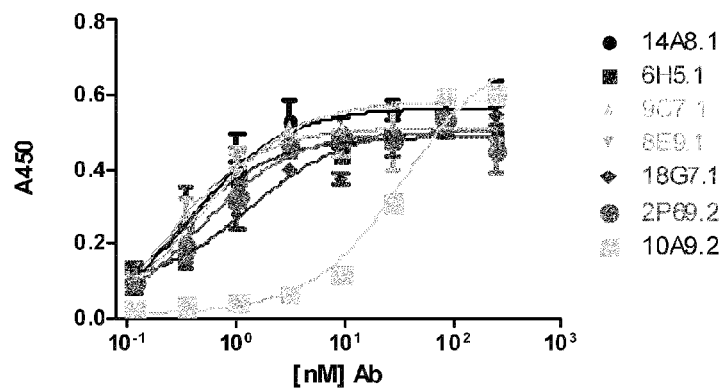
*Fig. 9F*
|  | 14A8.1 | 6H5.1 | 9C7.1 | 8E9.1 | 18G7.1 | 2P69.2 | 10A9.2 |
|---|---|---|---|---|---|---|---|
| EC50 | 0.3792 | 0.2844 | 0.4986 | 0.2036 | 1.352 | 0.4662 | 35.22 |
*Fig. 9G*
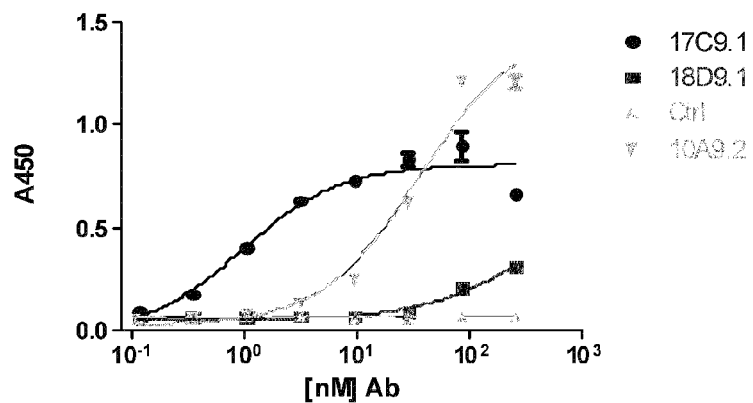
*Fig. 9H*
|  | 17C9.1 | 18D9.1 | Ctrl | 10A9.2 |
|---|---|---|---|---|
| EC50 | 0.9520 | 225.4 | 1579 | 35.22 |

A

Limiting Dilution Analysis of CSCs after GPR49 mAb Treatment

B

Colon Tumor Formation in Animals Implanted with Previously Treated Tumors

METHODS OF TREATING CANCER BY ADMINISTERING ANTI-GPR49 ANTIBODIES

CROSS-REFERENCE TO RELATED APPLICATIONS

This application is the U.S. National Phase of Application No. PCT/US2012/062866 entitled "ANTI-GPR49 ANTIBODIES" filed Oct. 31, 2012 and published in English on May 10, 2013 as WO 2013/067057 which claims the benefit of U.S. Provisional Patent Application 61/554,435, filed on Nov. 1, 2011 and entitled ANTI-GPR49 ANTIBODIES, the entirety of which is hereby incorporated by reference herein.

REFERENCE TO SEQUENCE LISTING

The present application is filed with a Sequence Listing in Electronic format. The Sequence Listing is provided as a file entitled BIONO.004WO_Sequence.txt, created Oct. 26, 2012, which is approximately 31 kb in size. The information in the electronic format of the sequence listing is incorporated herein by reference in its entirety.

FIELD

This application relates generally to the field of cancer biology. More particularly, embodiments are drawn to antibodies against GPR49 and uses of such antibodies. Several embodiments relate to monoclonal, humanized, or fully human antibodies against GPR49, hybridomas or other cell lines expressing such antibodies, nucleic acids and vectors comprising nucleic acids encoding for such antibodies.

BACKGROUND

G-Protein-coupled Receptor 49 (GPR49), also known as LGRS/HG38/FEX, belongs to the leucine-rich repeat containing G-protein-coupled receptors (LGRs) structurally similar to glycoprotein hormone receptors. LGRs are divided into three subgroups: (1) glycoprotein hormone receptors including thyroid-stimulating hormone (TSH) receptor, follicle-stimulating hormone (FSH) receptor, and luteinizing hormone (LH) receptor; (2) relaxin receptors LGR7 and LGR8; and (3) GPR48, GPR49, and LGR6. GPR49 is expressed in several tissues including the intestine, skeletal muscle, placenta, brain, and spinal cord. However, little is known about the function of GPR49.

SUMMARY

Several embodiments relate to a monoclonal antibody that binds to G-Protein Coupled Receptor 49 (GPR49) polypeptide and cross-reacts with G-Protein Coupled Receptor 48 (GPR48). In one aspect, the antibody does not cross react with Leucine-rich Repeat Containing G-protein-coupled Receptor 6 (LGR6) at a $K_d$ of less than $10^{-9}$ M. In the same aspect, the antibody does not cross-react with LGR6 at a $K_d$ of less than $10^{-6}$ M. Further in the same aspect, the antibody does not cross-react with LGR6 at a $K_d$ of less than $10^{-3}$ M. In another aspect, the antibody cross-reacts with GPR48 at a $K_d$ of less than $10^{-6}$. In the same aspect, the antibody cross-reacts with GPR48 at a $K_d$ of less than $10^{-9}$. In a further aspect, the GPR49 polypeptide has the amino acid sequence of SEQ ID NO: 1. In additional aspects, the antibody is an IgG class antibody, an IgG1 class antibody, a human antibody, or a mouse antibody. In several aspects, the antibody is monoclonal antibody 76C12. In a further aspect, the antibody binds to GPR49 polypeptide at a $K_d$ of less than $10^{-9}$ M. In the same aspect, the antibody binds to GPR49 polypeptide at a $K_d$ of less than $10^{-12}$ M.

In various aspects, the antibody competitively inhibits a monoclonal antibody selected from the group consisting of 71C10, 86C11, 66D05, 76C12, 78F05, and 76B04, or a monoclonal antibody produced by a hybridoma cell selected from the group consisting of monoclonal antibody 2B5.5, 7F8.2, 1B3.5, 9C6.4, 6H5.4, 10A6.7, 10A9.2, 2G8.1, 6C10.5, 6G10.3, 8H8.1, 6B10.2, 3B8.11, 2F12.5, 5G2.11, 1F10.5, 10E1.1, 7C3.4, 2H9.2, 5B12.4, 3G8.1, 5F2.5, 6G10.1, 14H9.1, 12G5.1, 6E10.1, 14F7.1, 4A10.2, 3F11.1, 11F6.1, 5B10.1, 14A8.1, 8E9.1, 9C7.1, 4F6.2, 1B8.1, 18G7.1, 12E3.1, 6H5.1, 2P69.2, 17C9.1, 2H5.1, and 10A9.2.

Certain embodiments are drawn to a method of producing an antibody or fragment thereof which specifically binds GPR49, comprising culturing a host cell comprising a vector which comprises a polynucleotide sequence encoding the antibody of claim 1; and recovering said antibody, or fragment thereof.

BRIEF DESCRIPTION OF THE DRAWINGS

FIGS. 8A-8D depict data for binding of murine antibodies to CHO cells expressing GPR49-Flag-His. FIGS. 8A and 8C are graphs showing binding of murine GPR49 antibodies to CHO GPR49-Flag-His expressing cells by FACs. FIGS. 8B and 8D are tables indicating the EC50 of the antibodies of FIGS. 8A and 8C, respectively.

FIGS. 9A-9H depict data for binding of murine antibodies to GPR49-Fc. FIGS. 9A, 9C, 9E, and 9G are graphs showing binding of second generation mouse antibodies to GPR49 by direct ELISA. FIGS. 9B, 9D, 9F, and 9H are tables indicating the EC50 of the antibodies of FIGS. 9A, 9C, 9E, and 9G, respectively.

FIG. 18 panel B is a graph showing that Anti-GPR49 antibody treatment inhibits the ability of CRC tumors with K-Ras, PI3K, PTEN, and p53 mutations from re-forming new tumors when transplanted into secondary recipient mice.

DETAILED DESCRIPTION

Figure 1:
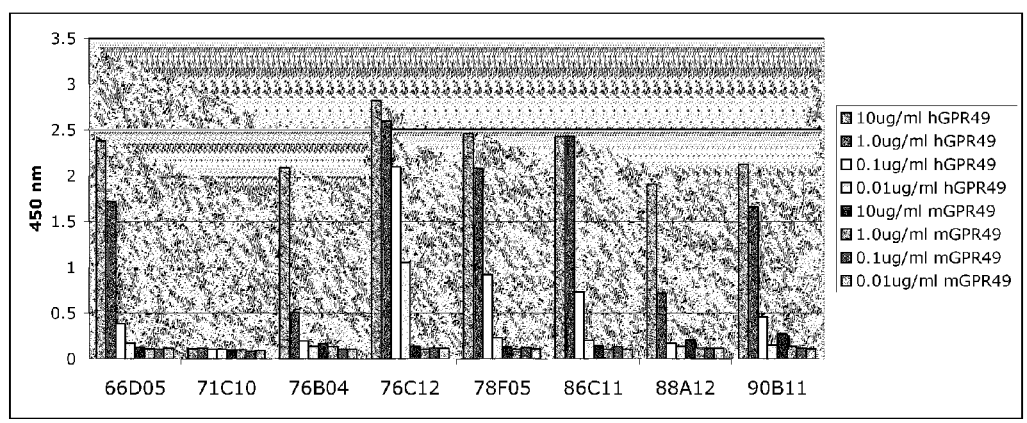
FIG. 1 is a bar graph showing binding of anti-GPR49 Fabs to human GPR49-Fc by ELISA.

Several embodiments of the present application are drawn to antibodies against GPR49 and inhibiting cancer stem cell growth with such antibodies. Various embodiments relate to humanized or fully human antibodies against GPR49, hybridomas or other cell lines expressing such antibodies, nucleic acids and vectors comprising nucleic acids encoding for such antibodies, and methods of blocking cancer stem cell growth with such antibodies.

Anti-GPR49 Antibodies

Several embodiments are drawn to anti-GPR49 antibodies. As used herein, GPR49 includes, but is not limited to, human GPR49 including the polypeptide of NCBI Accession No. NP_003658.1 (SEQ ID NO: 1), which is encoded by the coding nucleotide sequence within NM_003667.2 (SEQ ID NO: 2), or fragments thereof. The amino acid sequence of NCBI Accession No. NP_003658.1 and nucleotide sequence of NM_003667.2 are fully incorporated by reference in their entireties. Examples of GPR49 fragments contemplated herein include the GPR49 ectodomain, transmembrane domain, or intracellular domain and portions thereof As used herein, the term "antibody" includes, but is not limited to, synthetic antibodies, monoclonal antibodies, recombinantly produced antibodies, intrabodies, multispecific antibodies (including bi-specific antibodies), human antibodies, humanized antibodies, chimeric antibodies, synthetic antibodies, single-chain Fvs (scFv), Fab fragments, F(ab') fragments, disulfide-linked Fvs (sdFv) (including bi-specific sdFvs), and anti-idiotypic (anti-Id) antibodies, and epitope-binding fragments of any of the above. The antibodies of several embodiments provided herein may be mono-specific, bispecific, trispecific or of greater multispecificity. Multispecific antibodies may be specific for different epitopes of a polypeptide or may be specific for both a polypeptide as well as for a heterologous epitope, such as a heterologous polypeptide or solid support material. See, e.g., PCT publications WO 93/17715; WO 92/08802; WO91/00360; WO 92/05793; Tuft, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992); each of which is incorporated herein by reference in its entirety.

Other anti-GPR49 antibodies contemplated include "oligoclonal" antibodies. As used herein, the term "oligoclonal" antibodies" refers to a predetermined mixture of distinct monoclonal antibodies. Methods for generating oligoclonal antibodies are known in the art. See, e.g., "Examples Section", example 1, PCT publication WO 95/20401; U.S. Pat. Nos. 5,789,208 and 6,335,163; each of which is incorporated herein by reference in its entirety. In certain embodiments, oligoclonal antibodies consist of a predetermined mixture of antibodies against one or more epitopes generated in a single cell. In other embodiments, oligoclonal antibodies comprise a plurality of heavy chains capable of pairing with a common light chain to generate antibodies with multiple specificities (e.g., PCT publication WO 04/009618, which is incorporated herein by reference in its entirety). Oligoclonal antibodies are particularly useful when it is desired to target multiple epitopes on a single target molecule (e.g., GPR49). Those skilled in the art will know or can determine what type of antibody or mixture of antibodies is applicable for an intended purpose and desired need. In particular, antibodies of several embodiments include immunoglobulin molecules and immunologically active portions of immunoglobulin molecules, i.e., molecules that contain an antigen binding site that specifically binds to a GPR49 antigen (e.g., one or more complementarity determining regions (CDRs) of an anti-GPR49 antibody). It is also specifically contemplated that the antibodies of several embodiments include immunoglobulin molecules and immunologically active portions of immunoglobulin molecules, i.e., molecules that contain an antigen binding site that specifically binds to a GPR49 antigen (e.g., one or more complementarity determining regions (CDRs) of an anti-GPR49 antibody).

Several embodiments are drawn to the anti-GPR49 human Fabs produced as described in the Examples below, including antibodies 71C10, 86C11, 66D05, 76C12, 78F05, and 76B04, which bind to a human GPR49-Fc ectodomain (GPR49-RFc) (SEQ ID NO: 3). Several embodiments are drawn to the full-length human IgGs of these Fabs as described in the Examples.

Several embodiments relate to the mouse monoclonal antibodies raised against the human GPR49 ectodomain (GPR49-His) (SEQ ID NO: 4) as described in the Examples below, including antibodies 2B5.5, 7F8.2, 1B3.5, 9C6.4, 6H5.4, 10A6.7, 10A9.2, 2G8.1, 6C10.5, 6G10.3, 8H8.1, 6B10.2, 3B8.11, 2F12.5, 5G2.11, 1F10.5, 10E1.1, 7C3.4, 2H9.2, 5B12.4, 3G8.1, 5F2.5, and 6G10.1.

Several embodiments are drawn to the mouse monoclonal antibodies raised against full-length human GPR49 as described in the Examples below, including antibodies 14H9.1, 12G5.1, 6E10.1, 14F7.1, 4A10.2, 3F11.1, 11F6.1, 5B10.1, 14A8.1, 8E9.1, 9C7.1, 4F6.2, 1B8.1, 18G7.1, 12E3.1, 6H5.1, 2P69.2, 17C9.1, 2H5.1, and 10A9.2.

The anti-GPR49 antibodies of several embodiments can be of any type (e.g., IgG, IgE, IgM, IgD, IgA and IgY), class (e.g., IgG1, IgG2, IgG3, IgG4, IgA1 and IgA2) or subclass of immunoglobulin molecule. Immunoglobulins may have both a heavy and light chain. An array of IgG, IgE, IgM, IgD, IgA, and IgY heavy chains may be paired with a light chain of the kappa or lambda forms.

Several embodiments relate to a hybridoma that produces the light chain and/or the heavy chain of an anti-GPR49 antibody, including any one of the anti-GPR49 antibodies designated as 2B5.5, 7F8.2, 1B3.5, 9C6.4, 6H5.4, 10A6.7, 10A9.2, 2G8.1, 6C10.5, 6G10.3, 8H8.1, 6B10.2, 3B8.11, 2F12.5, 5G2.11, 1F10.5, 10E1.1, 7C3.4, 2H9.2, 5B12.4, 3G8.1, 5F2.5, 6G10.1, 14H9.1, 12G5.1, 6E10.1, 14F7.1, 4A10.2, 3F11.1, 11F6.1, 5B10.1, 14A8.1, 8E9.1, 9C7.1, 4F6.2, 1B8.1, 18G7.1, 12E3.1, 6H5.1, 2P69.2, 17C9.1, 2H5.1, and 10A9.2 produced and described in the Examples below. In one aspect, the hybridoma produces the light chain and/or the heavy chain of a humanized or fully human monoclonal antibody.

Some embodiments are drawn to a nucleic acid molecule encoding the light chain or the heavy chain of an anti-GPR49 antibody, including any one of the anti-GPR49 antibodies designated as 2B5.5, 7F8.2, 1B3.5, 9C6.4, 6H5.4, 10A6.7, 10A9.2, 2G8.1, 6C10.5, 6G10.3, 8H8.1, 6B10.2, 3B8.11, 2F12.5, 5G2.11, 1F10.5, 10E1.1, 7C3.4, 2H9.2, 5B12.4, 3G8.1, 5F2.5, 6G10.1, 14H9.1, 12G5.1, 6E10.1, 14F7.1, 4A10.2, 3F11.1, 11F6.1, 5B10.1, 14A8.1, 8E9.1, 9C7.1, 4F6.2, 1B8.1, 18G7.1, 12E3.1, 6H5.1, 2P69.2, 17C9.1, 2H5.1, and 10A9.2 produced and described in the Examples below. In one aspect, a nucleic acid molecule encodes the light chain or the heavy chain of a humanized or fully human monoclonal antibody.

Various embodiments are directed to a vector comprising a nucleic acid molecule or molecules encoding a light chain and/or a heavy chain of an anti-GPR49 antibody, including any one of the anti-GPR49 antibodies designated as 2B5.5, 7F8.2, 1B3.5, 9C6.4, 6H5.4, 10A6.7, 10A9.2, 2G8.1, 6C10.5, 6G10.3, 8H8.1, 6B10.2, 3B8.11, 2F12.5, 5G2.11, 1F10.5, 10E1.1, 7C3.4, 2H9.2, 5B12.4, 3G8.1, 5F2.5, 6G10.1, 14H9.1, 12G5.1, 6E10.1, 14F7.1, 4A10.2, 3F11.1, 11F6.1, 5B10.1, 14A8.1, 8E9.1, 9C7.1, 4F6.2, 1B8.1, 18G7.1, 12E3.1, 6H5.1, 2P69.2, 17C9.1, 2H5.1, and 10A9.2 produced and described in the Examples below.

Other embodiments relate to a method of making an anti-GPR49 antibody comprising transfecting at least one host cell with at least one nucleic acid molecule encoding an anti-GPR49 antibody, expressing the nucleic acid molecule in said host cell and isolating said antibody. In several aspects, such anti-GPR49 antibody includes any one of the anti-GPR49 antibodies designated as 2B5.5, 7F8.2, 1B3.5, 9C6.4, 6H5.4, 10A6.7, 10A9.2, 2G8.1, 6C10.5, 6G10.3, 8H8.1, 6B10.2, 3B8.11, 2F12.5, 5G2.11, 1F10.5, 10E1.1, 7C3.4, 2H9.2, 5B12.4, 3G8.1, 5F2.5, 6G10.1, 14H9.1, 12G5.1, 6E10.1, 14F7.1, 4A10.2, 3F11.1, 11F6.1, 5B10.1, 14A8.1, 8E9.1, 9C7.1, 4F6.2, 1B8.1, 18G7.1, 12E3.1, 6H5.1, 2P69.2, 17C9.1, 2H5.1, and 10A9.2 produced and described in the Examples below In several embodiments, antibodies can specifically bind GPR49 and antigenic fragments thereof with a dissociation constant or $K_d$ ($k_{off}/k_{on}$) of less than $10^{-5}$ M, or of less than $10^{-6}$ M, or of less than $10^{-7}$ M, or of less than $10^{-8}$ M, or of less than $10^{-9}$ M, or of less than $10^{-10}$ M, or of less than $10^{-11}$ M or of less than $10^{-12}$ M or of less than $10^{-13}$ M.

In another embodiment, the antibody can bind to GPR49 and/or antigenic fragments thereof with a $K_{off}$ of less than $1\times10^{-3}$ s$^{-1}$. In other embodiments, the antibody binds to GPR49 and antigenic fragments thereof with a $K_{off}$ of less than $10^{-3}$ s$^{--1}$, less than $5\times10^{-3}$ s$^{-1}$, less than $10^{-4}$ s$^{-1}$, less than $5\times10^{-4}$ s$^{-1}$, less than $10^{-5}$ s$^{-1}$, less than $5\times10^{-5}$ s$^{-1}$, less than $10^{-6}$ s$^{-1}$, less than $5\times10^{-6}$ s$^{-1}$, less than $10^{-7}$ s$^{-1}$, less than $5\times10^{-7}$ s$^{-1}$, less than $10^{-8}$ s$^{-1}$, less than $5\times10^{-8}$ s$^{-1}$, less than $10^{-9}$ s$^{-1}$, less than $5\times10^{-9}$ s$^{-1}$, or less than $10^{-10}$ s$^{-1}$.

In another embodiment, the antibody binds to GPR49 and/or antigenic fragments thereof with an association rate constant or $k_{on}$ rate of at least $10^{-5}$ M s$^{-1}$, at least $5\times10^{-5}$ M$^{-1}$s$^{-1}$, at least $10^{-6}$ M$^{-1}$ s$^{-1}$, at least $5\times10^{-6}$ M$^{-1}$ s$^{-1}$, at least $10^{-7}$ M$^{-1}$ s$^{-1}$, at least $5\times10^{-7}$ M$^{-1}$ s$^{-1}$, or at least $10^{-8}$ M$^{-1}$ s$^{-1}$, or at least $10^{-9}$ M$^{-1}$ s$^{-1}$.

An additional embodiment includes antibodies that have certain preferred biochemical characteristics such as a particular isoelectric point (pI) or melting temperature (Tm).

In one embodiment, the high affinity antibodies have a pI ranging from 5.5 to 9.5. In one embodiment, the high affinity antibodies of several embodiments have a Tm ranging from about 65° C. to about 120° C.

Antibodies of several embodiments also encompass those that have half-lives (e.g., serum half-lives) in a mammal, (e.g., a human), of greater than 1 day, greater than 2 days, greater than 3 days, greater than 4 days, greater than 5 days, greater than 6 days, greater than 7 days, greater than 8 days, greater than 9 days, greater than 10 days, greater than 15 days, greater than 20 days, greater than 25 days, greater than 30 days, greater than 35 days, greater than 40 days, greater than 45 days, greater than 2 months, greater than 3 months, greater than 4 months, or greater than 5 months. The increased half-lives of the antibodies in a mammal, (e.g., a human), results in a higher serum titer of said antibodies or antibody fragments in the mammal, and thus, reduces the frequency of the administration of said antibodies or antibody fragments and/or reduces the concentration of said antibodies or antibody fragments to be administered. Antibodies having increased in vivo half-lives can be generated by techniques known to those of skill in the art. For example, antibodies with increased in vivo half-lives can be generated by modifying (e.g., substituting, deleting or adding) amino acid residues identified as involved in the interaction between the Fc domain and the FcRn receptor (see, e.g., International Publication Nos. WO 97/34631; WO 04/029207; U.S. Pat. No. 6,737,056 and U.S. Patent Publication No. 2003/0190311 and discussed in more detail below); each of which is incorporated herein by reference in its entirety.

In several embodiments, the antibodies may comprise modifications/substitutions and/or novel amino acids within their Fc domains such as, for example, those disclosed in Ghetie et al., 1997, Nat. Biotech. 15:637-40; Duncan et al, 1988, Nature 332:563-564; Lund et al., 1991, J. Immunol. 147:2657-2662; Lund et al, 1992, Mol Immunol 29:53-59; Alegre et al, 1994, Transplantation 57:1537-1543; Hutchins et al., 1995, Proc Natl. Acad Sci USA 92:11980-11984; Jefferis et al, 1995, Immunol Lett. 44:111-117; Lund et al., 1995, Faseb J 9:115-119; Jefferis et al, 1996, Immunol Lett 54:101-104; Lund et al, 1996, J Immunol 157:4963-4969; Armour et al., 1999, Eur J Immunol 29:2613-2624; Idusogie et al, 2000, J Immunol 164:4178-4184; Reddy et al, 2000, J Immunol 164:1925-1933; Xu et al., 2000, Cell Immunol 200:16-26; Idusogie et al, 2001, J Immunol 166:2571-2575; Shields et al., 2001, J Biol Chem 276:6591-6604; Jefferis et al, 2002, Immunol Lett 82:57-65; Presta et al., 2002, Biochem Soc Trans 30:487-490); U.S. Pat. Nos. 5,624,821; 5,885,573; 5,677,425; 6,165,745; 6,277,375; 5,869,046; 6,121,022; 5,624,821; 5,648,260; 6,194,551; 6,737,056; 6,821,505; 6,277,375; U.S. patent application Ser. No. 10/370,749 and PCT Publications WO 94/2935; WO 99/58572; WO 00/42072; WO 02/060919, WO 04/029207; each of which is incorporated herein by reference in its entirety. Other modifications/substitutions of the Fc domain will be readily apparent to one skilled in the art.

Antibodies can comprise modifications/substitutions and/or novel amino acid residues in their Fc regions that can be generated by numerous methods well known to one skilled in the art. Non-limiting examples include, isolating antibody coding regions (e.g., from hybridoma) and making one or more desired substitutions in the Fc region of the isolated antibody coding region. Alternatively, the variable regions of an antibody may be subcloned into a vector encoding an Fc region comprising one or modifications/substitutions and/or novel amino acid residues.

Antibodies of several embodiments may also be modified to alter glycosylation, again to alter one or more functional properties of the antibody.

In various embodiments, the glycosylation of the antibodies can be modified. For example, an aglycosylated antibody can be made (i.e., the antibody lacks glycosylation). Glycosylation can be altered to, for example, increase the affinity of the antibody for a target antigen. Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861; each of which is incorporated herein by reference in its entirety.

Additionally or alternatively, an antibody of several embodiments can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies to thereby produce an antibody with altered glycosylation. See, for example, Shields, R. L. et al. (2002) *J. Biol. Chem.* 277:26733-26740; Umana et al. (1999) *Nat. Biotech.* 17:176-1, as well as, European Patent No: EP 1,176,195; PCT Publications WO 03/035835; WO 99/54342; each of which is incorporated herein by reference in its entirety.

The antibodies of several embodiments can be used either alone or in combination with other compositions. The antibodies may further be recombinantly fused to a heterologous polypeptide at the N- or C-terminus or chemically conjugated (including covalent and non-covalent conjugations) to polypeptides or other compositions. For example, antibodies can be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387; each of which is incorporated herein by reference in its entirety.

Antibodies provided herein can include derivatives that are modified, i.e., by the covalent attachment of any type of molecule to the antibody such that covalent attachment does not prevent the antibody from binding an GPR49 polypeptide or fragment thereof and/or generating a desired response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

In several embodiments, the antibodies specifically bind a polypeptide comprising or consisting of a GPR49 polypeptide having at least 60% identity, or at least 70% identity, or at least 80% identity, at least 85% identity, at least 90% identity, at least 95% identity, or at least at least 97% identity, or at least 99% identity, or 100% identity to the human GPR49 polypeptide of NCBI Accession Nos. NP_003658.1 (SEQ ID NO: 1) or fragments thereof. Such fragments can, for example, be at least about 5, 10, 15, 20, 25, 50, 75, 100, 150, 200, 250, 300, 350, 400, 450, 500, 550, 600, 650, 700, 750, 800, 850, or 900 contiguous or non-contiguous amino acids of SEQ ID NO: 1, or any number of contiguous or non-contiguous amino acids in between any of the aforementioned lengths.

The percent identity of two amino acid sequences (or two nucleic acid sequences) can be determined, for example, by aligning the sequences for optimal comparison purposes (e.g., gaps can be introduced in the sequence of a first sequence). The amino acids or nucleotides at corresponding positions are then compared, and the percent identity between the two sequences is a function of the number of identical positions shared by the sequences (i.e., % identity=# of identical positions/total # of positions ×100). The actual comparison of the two sequences can be accomplished by well-known methods, for example, using a mathematical algorithm. A specific, non-limiting example of such a mathematical algorithm is described in Karlin et al., Proc. Natl. Acad. Sci. USA, 90:5873-5877 (1993), which is incorporated herein by reference in its entirety. Such an algorithm is incorporated into the BLASTN and BLASTX programs (version 2.2) as described in Schaffer et al., Nucleic Acids Res., 29:2994-3005 (2001), which is incorporated herein by reference in its entirety. When utilizing BLAST and Gapped BLAST programs, the default parameters of the respective programs (e.g., BLASTN) can be used. See http://www.ncbi.nlm.nih.gov, as available on Apr. 10, 2002. In one embodiment, the database searched is a non-redundant (NR) database, and parameters for sequence comparison can be set at: no filters; Expect value of 10; Word Size of 3; the Matrix is BLOSUM62; and Gap Costs have an Existence of 11 and an Extension of 1.

Several embodiments also encompass variants of the above described antibodies, including any one of the anti-GPR49 antibodies designated as 2B5.5, 7F8.2, 1B3.5, 9C6.4, 6H5.4, 10A6.7, 10A9.2, 2G8.1, 6C10.5, 6G10.3, 8H8.1, 6B10.2, 3B8.11, 2F12.5, 5G2.11, 1F10.5, 10E1.1, 7C3.4, 2H9.2, 5B12.4, 3G8.1, 5F2.5, 6G10.1, 14H9.1, 12G5.1, 6E10.1, 14F7.1, 4A10.2, 3F11.1, 11F6.1, 5B10.1, 14A8.1, 8E9.1, 9C7.1, 4F6.2, 1B8.1, 18G7.1, 12E3.1, 6H5.1, 2P69.2, 17C9.1, 2H5.1, and 10A9.2 produced and described in the Examples below, comprising one or more amino acid residue substitutions in the variable light ($V_L$) domain and/or variable heavy ($V_H$) domain. Several also encompass variants of the above described antibodies with one or more additional amino acid residue substitutions in one or more $V_L$ CDRs and/or one or more $V_H$ CDRs. The antibody generated by introducing substitutions in the $V_H$ domain, $V_H$ CDRs, $V_L$ domain and/or $V_L$ CDRs of the above described antibodies can be tested in vitro and in vivo, for example, for its ability to bind to GPR49 (by, e.g., immunoassays including, but not limited to ELISAs and BIAcore).

In other embodiments, antibodies can have at least one, at least two, at least three, at least four, at least five, or at least six of the CDRs of the antibodies described above, including any one of the anti-GPR49 antibodies designated as 2B5.5, 7F8.2, 1B3.5, 9C6.4, 6H5.4, 10A6.7, 10A9.2, 2G8.1, 6C10.5, 6G10.3, 8H8.1, 6B10.2, 3B8.11, 2F12.5, 5G2.11, 1F10.5, 10E1.1, 7C3.4, 2H9.2, 5B12.4, 3G8.1, 5F2.5, 6G10.1, 14H9.1, 12G5.1, 6E10.1, 14F7.1, 4A10.2, 3F11.1, 11F6.1, 5B10.1, 14A8.1, 8E9.1, 9C7.1, 4F6.2, 1B8.1, 18G7.1, 12E3.1, 6H5.1, 2P69.2, 17C9.1, 2H5.1, and 10A9.2 produced and described in the Examples below.

Various embodiments include antibodies that specifically bind to GPR49 comprising derivatives of the $V_H$ domains, $V_H$ CDRs, $V_L$ domains, or $V_L$ CDRs of anti-GPR49 antibodies, such as any one of the anti-GPR49 antibodies designated as 2B5.5, 7F8.2, 1B3.5, 9C6.4, 6H5.4, 10A6.7, 10A9.2, 2G8.1, 6C10.5, 6G10.3, 8H8.1, 6B10.2, 3B8.11, 2F12.5, 5G2.11, 1F10.5, 10E1.1, 7C3.4, 2H9.2, 5B12.4, 3G8.1, 5F2.5, 6G10.1, 14H9.1, 12G5.1, 6E10.1, 14F7.1, 4A10.2, 3F11.1, 11F6.1, 5B10.1, 14A8.1, 8E9.1, 9C7.1, 4F6.2, 1B8.1, 18G7.1, 12E3.1, 6H5.1, 2P69.2, 17C9.1, 2H5.1, and 10A9.2 produced and described in the Examples below, that specifically bind to GPR49. Standard techniques known to those of skill in the art can be used to introduce mutations (e.g., additions, deletions, and/or substitutions) in the nucleotide sequence encoding an antibody, including, for example, site-directed mutagenesis and PCR-mediated mutagenesis are routinely used to generate amino acid substitutions. In one embodiment, the $V_H$ and/or $V_L$ CDRs derivatives include less than 25 amino acid substitutions, less than 20 amino acid substitutions, less than 15 amino acid substitutions, less than 10 amino acid substitutions, less than 5 amino acid substitutions, less than 4 amino acid substitutions, less than 3 amino acid substitutions, or less than 2 amino acid substitutions relative to the original $V_H$ and/or $V_L$ CDRs. In another embodiment, the $V_H$ and/or $V_L$ CDRs derivatives have conservative amino acid substitutions (e.g. supra) made at one or more predicted non-essential amino acid residues (i.e., amino acid residues which are not critical for the antibody to specifically bind to GPR49). Alternatively, mutations can be introduced randomly along all or part of the $V_H$ and/or $V_L$ CDR coding sequence, such as by saturation mutagenesis, and the resultant mutants can be screened for biological activity to identify mutants that retain activity. Following mutagenesis, the encoded antibody can be expressed and the activity of the antibody can be determined.

Several embodiments also encompass antibodies that specifically bind to GPR49 or a fragment thereof, said antibodies comprising an amino acid sequence of a variable heavy chain and/or variable light chain that is at least 45%, at least 50%, at least 55%, at least 60%, at least 65%, at least 70%, at least 75%, at least 80%, at least 85%, at least 90%, at least 95%, or at least 99% identical to the amino acid sequence of the variable heavy chain and/or light chain of any of the antibodies described herein including any one of the anti-GPR49 antibodies designated as 2B5.5, 7F8.2, 1B3.5, 9C6.4, 6H5.4, 10A6.7, 10A9.2, 2G8.1, 6C10.5, 6G10.3, 8H8.1, 6B10.2, 3B8.11, 2F12.5, 5G2.11, 1F10.5, 10E1.1, 7C3.4, 2H9.2, 5B12.4, 3G8.1, 5F2.5, 6G10.1, 14H9.1, 12G5.1, 6E10.1, 14F7.1, 4A10.2, 3F11.1, 11F6.1, 5B10.1, 14A8.1, 8E9.1, 9C7.1, 4F6.2, 1B8.1, 18G7.1, 12E3.1, 6H5.1, 2P69.2, 17C9.1, 2H5.1, and 10A9.2 produced and described in the Examples below.

Various embodiments further encompass antibodies that specifically bind to GPR49 or a fragment thereof, said antibodies or antibody fragments comprising an amino acid sequence of one or more CDRs that is at least 45%, at least 50%, at least 55%, at least 60%, at least 65%, at least 70%, at least 75%, at least 80%, at least 85%, at least 90%, at least 95%, or at least 99% identical to the amino acid sequence of one or more CDRs of the antibodies described herein including any one of the anti-GPR49 antibodies designated as 2B5.5, 7F8.2, 1B3.5, 9C6.4, 6H5.4, 10A6.7, 10A9.2, 2G8.1, 6C10.5, 6G10.3, 8H8.1, 6B10.2, 3B8.11, 2F12.5, 5G2.11, 1F10.5, 10E1.1, 7C3.4, 2H9.2, 5B12.4, 3G8.1, 5F2.5, 6G10.1, 14H9.1, 12G5.1, 6E10.1, 14F7.1, 4A10.2, 3F11.1, 11F6.1, 5B10.1, 14A8.1, 8E9.1, 9C7.1, 4F6.2, 1B8.1, 18G7.1, 12E3.1, 6H5.1, 2P69.2, 17C9.1, 2H5.1, and 10A9.2 produced and described in the Examples below. The determination of percent identity of two amino acid sequences can be determined by any method known to one skilled in the art, including BLAST protein searches.

Another embodiment includes the introduction of conservative amino acid substitutions in any portion of an anti-GPR49 antibody, such as any one of the anti-GPR49 antibodies designated as 2B5.5, 7F8.2, 1B3.5, 9C6.4, 6H5.4, 10A6.7, 10A9.2, 2G8.1, 6C10.5, 6G10.3, 8H8.1, 6B10.2, 3B8.11, 2F12.5, 5G2.11, 1F10.5, 10E1.1, 7C3.4, 2H9.2, 5B12.4, 3G8.1, 5F2.5, 6G10.1, 14H9.1, 12G5.1, 6E10.1, 14F7.1, 4A10.2, 3F11.1, 11F6.1, 5B10.1, 14A8.1, 8E9.1, 9C7.1, 4F6.2, 1B8.1, 18G7.1, 12E3.1, 6H5.1, 2P69.2, 17C9.1, 2H5.1, and 10A9.2 produced and described in the Examples below. It is well known in the art that "conservative amino acid substitution" refers to amino acid substitutions that substitute functionally-equivalent amino acids. Conservative amino acid changes result in silent changes in the amino acid sequence of the resulting peptide. For example, one or more amino acids of a similar polarity act as functional equivalents and result in a silent alteration within the amino acid sequence of the peptide. Substitutions that are charge neutral and which replace a residue with a smaller residue may also be considered "conservative substitutions" even if the residues are in different groups (e.g., replacement of phenylalanine with the smaller isoleucine). Families of amino acid residues having similar side chains have been defined in the art. Several families of conservative amino acid substitutions are shown in Table 1.

TABLE 1

Families of Conservative Amino Acid Substitutions

| Family | Amino Acids |
|---|---|
| non-polar | Trp, Phe, Met, Leu, Ile, Val, Ala, Pro |
| uncharged polar | Gly, Ser, Thr, Asn, Gln, Tyr, Cys |
| acidic/negatively charged | Asp, Glu |
| basic/positively charged | Arg, Lys, His |
| Beta-branched | Thr, Val, Ile |
| residues that influence chain orientation | Gly, Pro |
| aromatic | Trp, Tyr, Phe, His |

The term "conservative amino acid substitution" also refers to the use of amino acid analogs or variants.

Methods of Generating Antibodies

Antibodies that specifically bind to a GPR49 polypeptide can be identified, for example, by immunoassays, BIAcore, or other techniques known to those of skill in the art.

The antibodies of several embodiments may be generated by any suitable method known in the art. Polyclonal antibodies to an antigen-of-interest can be produced by various procedures well known in the art. For example, a GPR49 polypeptide can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981); each of which is incorporated herein by reference in its entirety. The term "monoclonal antibody" (abbreviated as "mAb") as used herein is not limited to antibodies produced through hybridoma technology. The term "monoclonal antibody" refers to an antibody that is derived from a single clone, including any eukaryotic, prokaryotic, or phage clone, and not the method by which it is produced. A "monoclonal antibody" may comprise, or alternatively consist of, two proteins, i.e., a heavy and a light chain.

Methods for producing and screening for specific antibodies using hybridoma technology are routine and well known in the art. In a non-limiting example, mice can be immunized with a GPR49 polypeptide or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a GPR49 polypeptide. Ascites fluid, which generally contains high levels of antibodies, can be generated by immunizing mice with positive hybridoma clones.

Accordingly, several embodiments provide methods of generating monoclonal antibodies as well as antibodies produced by the method comprising culturing a hybridoma cell secreting an antibody wherein the hybridoma is generated by fusing splenocytes isolated from a mouse immunized with a GPR49 antigen with myeloma cells and then screening the hybridomas resulting from the fusion for hybridoma clones that secrete an antibody able to bind a GPR49 polypeptide.

Antibody fragments which recognize specific epitopes may be generated by known techniques. For example, Fab and F(ab')2 fragments of several embodiments may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

The antibodies of various embodiments can also be generated using various phage display methods known in the art. In phage display methods, functional antibody domains are displayed on the surface of phage particles which carry the polynucleotide sequences encoding them. In a particular embodiment, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of several embodiments include those disclosed in PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988), each of which is incorporated herein by reference in its entirety.

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988), each of which is incorporated herein by reference in its entirety.

Human Antibodies and Humanization of Antibodies

For some uses, including in vivo use of antibodies in humans and in vitro detection assays, it may be desirable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See, e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816,397; each of which is incorporated herein by reference in its entirety. Humanized antibodies are antibody molecules from non-human species antibody that bind the desired antigen having one or more complementarity determining regions (CDRs) from the non-human species and a framework region from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988); each of which is incorporated herein by reference in its entirety).

Human antibodies avoid some of the problems associated with antibodies that possess murine or rat variable and/or constant regions. The presence of such murine or rat derived proteins can lead to the rapid clearance of the antibodies or can lead to the generation of an immune response against the antibody by a patient. In order to avoid the utilization of murine or rat derived antibodies, antibodies can be humanized using a variety of techniques known in the art including, for example, CDR-grafting (EP 239,400; PCT publication WO 91/09967; U.S. Pat. Nos. 5,225,539; 5,530,101; and 5,585,089; each of which is incorporated herein by reference in its entirety), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), de-immunization (U.S. Patent Publication No. 20030153043) and chain shuffling (U.S. Pat. No. 5,565,332), each of which is incorporated herein by reference in its entirety.

Completely human antibodies can be used for therapeutic treatment of human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741, each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a GPR49 polypeptide. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995), which is incorporated herein by reference in its entirety. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598; each of which is incorporated herein by reference in its entirety. In addition, companies such as Abgenix, Inc. (Fremont, Calif.) and Genpharm (San Jose, Calif.) can be engaged to provide human antibodies directed against a selected antigen using technology similar to that described above. Abgenix, Inc. (Fremont, Calif.) provides XenoMouse® strains of mice that have been engineered to contain up to but less than 1000 kb-sized germline configured fragments of the human heavy chain locus and kappa light chain locus. See Mendez et al. Nature Genetics 15:146-156 (1997) and Green and Jakobovits J. Exp. Med. 188:483-495 (1998).

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and usually a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, 5,814,318, 5,877,397, 5,874,299, and 6,255,458 each to Lonberg and Kay, U.S. Pat. No. 5,591,669 and 6,023.010 to Krimpenfort and Berns, U.S. Pat. Nos. 5,612,205, 5,721,367, and 5,789, 215 to Berns et al., and U.S. Pat. No. 5,643,763 to Choi and Dunn, and GenPharm International U.S. patent application Ser. No. 07/574,748, filed Aug. 29, 1990, Ser. No. 07/575,962, filed Aug. 31, 1990, Ser. No. 07/810,279, filed Dec. 17, 1991, Ser. No. 07/853,408, filed Mar. 18, 1992, Ser. No. 07/904,068, filed Jun. 23, 1992, Ser. No. 07/990,860, filed Dec. 16, 1992, Ser. No. 08/053,131, filed Apr. 26, 1993, Ser. No. 08/096,762, filed Jul. 22, 1993, Ser. No. 08/155,301, filed Nov. 18, 1993, Ser. No. 08/161,739, filed Dec. 3, 1993, Ser. No. 08/165,699, filed Dec. 10, 1993, Ser. No. 08/209,741, filed Mar. 9, 1994, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175, the disclosures of which are hereby incorporated by reference in their entirety. See further Taylor et al., 1992, Chen et al., 1993, Tuaillon et al., 1993, Choi et al., 1993, Lonberg et al., (1994), Taylor et al., (1994), and Tuaillon et al., (1995), Fishwild et al., (1996), the disclosures of which are hereby incorporated by reference in their entirety.

Human antibodies can be produced from transgenic mice that have had large pieces of chromosomes or entire chromosomes introduced through microcell fusion. See European Patent Application Nos. 773 288 and 843 961, the disclosures of which are hereby incorporated by reference. Additionally, KM™-mice, which are the result of cross-breeding of Tc mice with Medarex's minilocus (Humab) mice have been generated. These mice possess the human IgH transchromosome of the Kirin mice and the kappa chain transgene of the Genpharm mice (Ishida et al., Cloning Stem Cells, (2002) 4:91-102).

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., *Bio/technology* 12:899-903 (1988), which is incorporated herein by reference in its entirety).

Further, antibodies to GPR49 polypeptides can, in turn, be utilized to generate anti-idiotype antibodies that "mimic" GPR49 polypeptides using techniques well known to those skilled in the art (See, e.g., Greenspan & Bona, FASEB J. 7(5):437-444; (1989) and Nissinoff, *J. Immunol.* 147(8): 2429-2438 (1991); each of which is incorporated herein by reference in its entirety).

In several embodiments, antibodies provided herein can be used therapeutically in vivo. Accordingly, the antibody can be modified to make it less immunogenic in the individual. For example, if the individual is human the antibody can be "humanized" where the complementarity determining region(s) of the antibody is transplanted into a human antibody (for example, as described in Jones et al., *Nature* 321:522-525, 1986; and Tempest et al., *Biotechnology* 9:266-271, 1991), which is incorporated herein by reference in its entirety.

Phage display technology can also be utilized to select antibody genes with binding activities towards the polypeptide either from repertoires of PCR amplified v-genes of lymphocytes from humans screened for possessing anti-GPR49 antibodies or from naive libraries (McCafferty et al., *Nature* 348:552-554, 1990; and Marks, et al., *Biotechnology* 10:779-783, 1992, which is incorporated herein by reference in its entirety). The affinity of these antibodies can also be improved by chain shuffling (Clackson et al., *Nature* 352: 624-628, 1991, which is incorporated herein by reference in its entirety).

Methods of Producing Antibodies

The antibodies of several embodiments can be produced by any method known in the art for the synthesis of antibodies, in particular, by chemical synthesis or preferably, by recombinant expression techniques.

Recombinant expression of an antibody or fragment, derivative or analog thereof, (e.g., a heavy or light chain of an antibody or a single chain antibody), requires construction of an expression vector containing a polynucleotide that encodes the antibody. Once a polynucleotide encoding an antibody molecule or a heavy or light chain of an antibody, or portion thereof (preferably containing the heavy or light chain variable domain) has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. Various embodiments thus provide replicable vectors comprising a nucleotide sequence encoding an antibody molecule, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464; each of which is incorporated herein by reference in its entirety) and the variable domain of the antibody may be cloned into such a vector for expression of the entire heavy or light chain.

The expression vector is transferred to a host cell by conventional techniques and the transfected cells are then cultured by conventional techniques to produce an antibody. Thus, several embodiments include host cells containing a polynucleotide encoding an antibody, or a heavy or light chain thereof, or a single chain antibody, operably linked to a heterologous promoter. Vectors encoding both the heavy and light chains may be co-expressed in the host cell for expression of the entire immunoglobulin molecule, as detailed below.

A variety of host-expression vector systems may be utilized to express the antibody molecules described herein. Such host-expression systems represent vehicles by which the coding sequences of interest may be produced and subsequently purified, but also represent cells which may, when transformed or transfected with the appropriate nucleotide coding sequences, express an antibody molecule in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, NSO, 3T3, PerC6 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Bacterial cells such as *Escherichia coli*, and eukaryotic cells can be used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., *Gene* 45:101 (1986); Cockett et al., *Bio/Technology* 8:2 (1990)). Also see, e.g., U.S. Pat. Nos. 5,827,739, 5,879,936, 5,981,216, and 5,658,759, each of which is incorporated herein by reference in its entirety.

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited to, the *E. coli* expression vector pUR278 (Ruther et al., *EMBO J.* 2:1791 (1983)), which is incorporated herein by reference in its entirety, in which the antibody coding sequence may be ligated individually into the vector in frame with the lacZ coding region so that a fusion protein is produced; pIN vectors (Inouye & Inouye, *Nucleic Acids Res.* 13:3101-3109 (1985); Van Heeke & Schuster, *J. Biol. Chem.* 24:5503-5509 (1989)), each of which is incorporated herein by reference in its entirety; and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts (e.g., see Logan & Shenk, *Proc. Natl. Acad. Sci. USA* 81:3655-3659 (1984), which is incorporated herein by reference in its entirety). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., *Methods in Enzymol.* 153:51-544 (1987), which is incorporated herein by reference in its entirety).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, W138, NSO, Per.C6 and in particular, breast cancer cell lines such as, for example, BT483, Hs578T, HTB2, BT20 and T47D, and normal mammary gland cell lines such as, for example, CRL7030 and Hs578Bst.

For long-term, high-yield production of recombinant proteins, stable expression can be used. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., *Cell* 11:223 (1977)), hypoxanthine-guanine phosphoribosyltransferase (Szybalska & Szybalski, *Proc. Natl. Acad. Sci. USA* 48:202 (1992)), and adenine phosphoribosyltransferase (Lowy et al., *Cell* 22:817 (1980)) genes can be employed in tk-, hgprt- or aprt-cells, respectively. Also, antimetabolite resistance can be used as the basis of selection for the following genes: dhfr, which confers resistance to methotrexate (Wigler et al., *Proc Natl. Acad. Sci. USA* 77:3567-3570 (1980); O'Hare et al., *Proc. Natl. Acad. Sci. USA* 78:1527 (1981)); gpt, which confers resistance to mycophenolic acid (Mulligan & Berg, *Proc. Natl. Acad. Sci. USA* 78:2072 (1981)); neo, which confers resistance to the aminoglycoside G-418 Clinical Pharmacy 12:488-505; Wu and Wu, *Biotherapy* 3:87-95 (1991); Tolstoshev, *Ann. Rev. Pharmacol. Toxicol.* 32:573-596 (1993); Mulligan, *Science* 260:926-932 (1993); and Morgan and Anderson, *Ann. Rev. Biochem.* 62:191-217 (1993); May, 1993, *TIB TECH* 11(5):155-215); and hygro, which confers resistance to hygromycin (Santerre et al., *Gene* 30:147 (1984), each of which is incorporated herein by reference in its entirety). Methods commonly known in the art of recombinant DNA technology may be routinely applied to select the desired recombinant clone, and such methods are described, for example, in Ausubel et al. (eds.), *Current Protocols in Molecular Biology*, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., *J. Mol. Biol.* 150:1 (1981), each of which is incorporated herein by reference in its entirety.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987), which is incorporated herein by reference in its entirety). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., *Mol. Cell. Biol.* 3:257 (1983), which is incorporated herein by reference in its entirety).

The host cell may be co-transfected with two expression vectors, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:562 (1986); Kohler, *Proc. Natl. Acad. Sci. USA* 77:2197 (1980), which is incorporated herein by reference in its entirety). The coding sequences for the heavy and light chains may comprise cDNA or genomic DNA.

Once an antibody molecule has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies or fragments thereof can be fused to heterologous polypeptide sequences described herein or otherwise known in the art, to facilitate purification.

Moreover, the antibodies or fragments thereof can be fused to marker sequences, such as a peptide to facilitate purification. In certain embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., *Proc. Natl. Acad. Sci. USA* 86:821-824 (1989), which is incorporated herein by reference in its entirety, for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., *Cell* 37:767 (1984), which is incorporated herein by reference in its entirety) and the "flag" tag.

The antibodies described herein include derivatives that are modified (e.g., by the covalent attachment of any type of molecule to the antibody). For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

Antibodies or fragments thereof with increased in vivo half-lives can be generated by attaching to said antibodies or antibody fragments polymer molecules such as high molecular weight polyethyleneglycol (PEG). PEG can be attached to said antibodies or antibody fragments with or without a multifunctional linker either through site-specific conjugation of the PEG to the N- or C-terminus of said antibodies or antibody fragments or via epsilon-amino groups present on lysine residues. Linear or branched polymer derivatization that results in minimal loss of biological activity will be used. The degree of conjugation will be closely monitored by SDS-PAGE and mass spectrometry to ensure proper conjugation of PEG molecules to the antibodies. Unreacted PEG can be separated from antibody-PEG conjugates by, e.g., size exclusion or ion-exchange chromatography.

Further, antibodies can be conjugated to albumin in order to make the antibody or antibody fragment more stable in vivo or have a longer half life in vivo. The techniques are well known in the art, see e.g., International Publication Nos. WO 93/15199, WO 93/15200, and WO 01/77137; and European Patent No. EP 413, 622, each of which is incorporated herein by reference in its entirety. Embodiments provided herein encompass the use of antibodies or fragments thereof conjugated or fused to one or more moieties, including but not limited to, peptides, polypeptides, proteins, fusion proteins, nucleic acid molecules, small molecules, mimetic agents, synthetic drugs, inorganic molecules, and organic molecules.

Various embodiments encompass the use of antibodies or fragments thereof recombinantly fused or chemically conjugated (including both covalent and non-covalent conjugations) to a heterologous protein or polypeptide (or fragment thereof, specifically to a polypeptide of at least 10, at least 20, at least 30, at least 40, at least 50, at least 60, at least 70, at least 80, at least 90 or at least 100 amino acids) to generate fusion proteins. In some embodiments, the antibodies or fragments thereof can be recombinantly fused or chemically conjugated (including both covalent and non-covalent conjugations) to a heterologous protein or polypeptide (or fragment thereof, specifically to a polypeptide of at least about 10, at least about 20, at least about 30, at least about 40, at least about 50, at least about 60, at least about 70, at least about 80, at least about 90 or at least about 100 amino acids) to generate fusion proteins. The fusion does not necessarily need to be direct, but may occur through linker sequences. For example, antibodies may be used to target heterologous polypeptides to particular cell types, either in vitro or in vivo, by fusing or conjugating the antibodies to antibodies specific for particular cell surface receptors. Antibodies fused or conjugated to heterologous polypeptides may also be used in in vitro immunoassays and purification methods using methods known in the art. See e.g., International publication No. WO 93/21232; European Patent No. EP 439,095; Naramura et al., 1994, Immunol. Lett. 39:91-99; U.S. Pat. No. 5,474,981; Gillies et al., 1992, PNAS 89:1428-1432; and Fell et al., 1991, J. Immunol. 146:2446-2452, each of which is incorporated herein by reference in its entirety.

Several embodiments include formulations comprising heterologous proteins, peptides or polypeptides fused or conjugated to antibody fragments. For example, the heterologous polypeptides may be fused or conjugated to a Fab fragment, Fd fragment, Fv fragment, F(ab)2 fragment, a VH domain, a VL domain, a VH CDR, a VL CDR, or fragment thereof. Methods for fusing or conjugating polypeptides to antibody portions are well known in the art. See, e.g., U.S. Pat. Nos. 5,336,603, 5,622,929, 5,359,046, 5,349,053, 5,447,851, and 5,112,946; European Patent Nos. EP 307,434 and EP 367, 166; International publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341, each of which is incorporated herein by reference in its entirety.

Additional fusion proteins of antibodies that specifically bind GPR49 or fragments thereof (e.g., supra), may be generated through the techniques of gene-shuffling, motif-shuffling, exon-shuffling, and/or codon-shuffling (collectively referred to as "DNA shuffling"). DNA shuffling may be employed to alter the activities of antibodies or fragments thereof (e.g., antibodies or fragments thereof with higher affinities and lower dissociation rates). See, generally, U.S. Pat. Nos. 5,605,793; 5,811,238; 5,830,721; 5,834,252; and 5,837,458, and Patten et al., 1997, Curr. Opinion Biotechnol. 8:724-33; Harayama, 1998, Trends Biotechnol. 16(2): 76-82; Hansson, et al., 1999, J. Mol. Biol. 287:265-76; and Lorenzo and Blasco, 1998, Biotechniques 24(2): 308-313, each of which is incorporated herein by reference in its entirety. Antibodies or fragments thereof, or the encoded antibodies or fragments thereof, may be altered by being subjected to random mutagenesis by error-prone PCR, random nucleotide insertion or other methods prior to recombination. One or more portions of a polynucleotide encoding an antibody or antibody fragment, which portions specifically bind to a C/CLP may be recombined with one or more components, motifs, sections, parts, domains, fragments, etc. of one or more heterologous molecules.

Moreover, the antibodies or fragments thereof can be fused to marker sequences, such as a peptide to facilitate purification. In certain embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, which is incorporated herein by reference in its entirety, for instance, hexahistidine provides for convenient purification of the fusion protein. Other peptide tags useful for purification include, but are not limited to, the hemagglutinin "HA" tag, which corresponds to an epitope derived from the influenza hemagglutinin protein (Wilson et al., 1984, *Cell* 37:767, which is incorporated herein by reference in its entirety) and the "flag" tag.

Various embodiments further encompass antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900, which is incorporated herein by reference in its entirety, for metal ions which can be conjugated to antibodies for use as diagnostics. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin; and examples of suitable radioactive material include but are not limited to, $^{125}$I, $^{131}$I, $^{111}$In or $^{99}$Tc, in addition positron emitting metals using various positron emission tomographies, nonradioactive paramagnetic metal ions, and molecules that are radiolabelled or conjugated to specific radioisotopes can be conjugated to the antibodies described herein.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, $^{213}$Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum(II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine). A more extensive list of therapeutic moieties can be found in PCT publication WO 03/075957, which is incorporated herein by reference in its entirety.

The conjugates can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, an apoptotic agent or an anti-angiogenic agent.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody in Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982), each of which is incorporated herein by reference in its entirety.

The antibodies can be conjugated to other polypeptides. Methods for fusing or conjugating antibodies to polypeptide moieties are known in the art. See, e.g., U.S. Pat. Nos. 5,336,603; 5,622,929; 5,359,046; 5,349,053; 5,447,851, and 5,112,946; EP 307,434; EP 367,166; PCT Publications WO 96/04388 and WO 91/06570; Ashkenazi et al., 1991, PNAS USA 88:10535; Zheng et al., 1995, J Immunol 154:5590; and Vil et al., 1992, PNAS USA 89:11337, each of which is incorporated herein by reference in its entirety. The fusion of an antibody to a moiety does not necessarily need to be direct, but may occur through linker sequences. Such linker molecules are commonly known in the art and described in Denardo et al., 1998, Clin Cancer Res 4:2483; Peterson et al., 1999, Bioconjug Chem 10:553; Zimmerman et al., 1999, Nucl Med Biol 26:943; Garnett, 2002, Adv Drug Deliv Rev 53:171. Alternatively, an antibody can be conjugated to a second antibody to form an antibody heteroconjugate as described by Segal in U.S. Pat. No. 4,676,980, each of which is incorporated herein by reference in its entirety.

While the present embodiments have been described in some detail for purposes of clarity and understanding, one skilled in the art will appreciate that various changes in form and detail can be made without departing from the true scope of the invention.

EXAMPLES

Having generally described embodiments drawn to antibodies against GPR49, hybridomas or other cell lines expressing such antibodies, nucleic acids and vectors comprising nucleic acids encoding for such antibodies, and methods of blocking cancer stem cell growth with such antibodies, a further understanding can be obtained by reference to certain specific examples which are provided for purposes of illustration only and are not intended to be limiting.

Example 1

Development of a Tumorsphere Assay to Maintain, Propagate and Enumerate Colon Cancer Stem Cells from Primary Colon Tumors An in vitro method was developed to maintain and propagate colon cancer stem cells based on the observation that normal and malignant stem cells from neural and breast tissue can be maintained in non-adherent neurosphere or mammosphere cultures. These sphere cultures are grown under "cancer stem cell" conditions: ultra-low-attachment plates to ensure non-adherent cultures, with no serum and supplemented with growth factors (i.e. EGF, bFGF) and anti-differentiation factors such as Leukemia-inhibitor-factor (LIF) (Singh et al., Nature 2004; Dontu et al., Genes Dev, 2003; Liu et al., Can Res 2006). Neuro- and mammospheres have stem cell features such as the capacity for self-renewal and differentiation. Sphere cultures established from malignant tumor tissue, termed tumorspheres, are highly tumorigenic in vivo, in addition to having self-renewal and differentiation capacity. Tumorspheres also have increased resistance to chemotherapeutic reagents, indicating that they are a relevant model for cancer drug development (Bao, 2006; Dean, 2005; Diehn, Clarke 2006; Eyler, Rich 2008; Li 2008). Colon cancer stem cells can be maintained and propagated in vitro as primary colon tumorspheres established from colon tumor biopsies (referred to as primary colon tumors). Primary colon tumorspheres described below successfully established xenograft tumors in immune deficient with as few as 10-100 cells. In contrast, typical standard tumor lines require 1e6 or greater cells to successfully establish xenograft tumors.

Methods:

The tumorsphere assay and cancer stem cells maintained in the tumorsphere cultures were used to design an assay to measure the number of CSCs based on the hematopoietic bone marrow assay used to measures stem/progenitor cells by their ability to form colonies in methycellulose (Bradley and Metcalf, 1966). In this assay, live single colon tumor cells derived from primary colon tumor xenografts or fresh patient biopsies were sorted by MoFlo and plated at between 1-1000 cells per well into 96-well ultra-low attachment plates. The cells were maintained in CSC medium for 3 weeks, with fresh medium exchange performed every 3-4 days. After 3 weeks, the number of cancer stem cells present in each well was determined by counting the number of colonies or tumorspheres in each well using a GELCOUNT colony counter and software (Oxford Optronix).

Results:

Three tumorsphere models were developed using primary colon xenograft tumorspheres CT1 and CT3 (29), and the tumor line DLD-1 to assess anti-cancer stem cell (CSC) activity in vitro.

Example 2

Selection of Human Fabs Specific to Human GPR49 from Phage Display Libraries

Human antibodies that specifically recognize the extracellular domain of a human GPR49 receptor were isolated using phage display technology.

Part I: Phage-Display Panning

Methods:

Recombinant human GPR49-Fc ectodomain (GPR49-Fc) (SEQ ID NO: 3) was used to screen a human naive phagemid Fab library containing $3.5 \times 10^{10}$ unique clones (Hoet, R. M., et al. NatBiotechnol. 23(3): 344-8 (2005)). Prior to incubation with the phage library, a biotinylated anti-Fc antibody was captured on magnetic beads, followed by captured of the GPR49-Fc fusion protein. Selections were performed as described in Hoet et al. After 3 rounds of panning, the 479 by gene III stump was removed by Mlu1 digestion, and the vector was relegated for soluble Fab expression in TGI cells.

Results:

61 unique clones were isolated in this panning. Unique clones were subsequently purified and binding was reconfirmed.

Part II: ELISA

Binding of Fabs to recombinant human GPR49-Fc ectodomain was demonstrated by ELISA. Methods: In brief, soluble GPR49-Fc fusion protein at 2.5 ug/ml in 0.025 M carbonate buffer, pH 9.6 was coated at 50 ul/well in a 96-well (IMMULON2 HB, Dynex Technologies, Inc., Cat. #3455) plate and incubated overnight at 4° C. The plate washed with phosphate-buffered saline (PBS, Irvine Scientific, Cat#9240), pH 7.4 plus 0.025% Tween 20 in the Skan Washer 300 (Skatron Instruments), blocked with buffer containing 1% nonfat milk, 0.05% Tween 20 in PBS, pH 7.4, and then incubated at room temperature for 1 hour. After incubation the plate was washed with PBS plus 0.025% Tween 20 in the Skan Washer 300. For the assay, the GPR49-coated plate was next incubated with the control and test antibodies of varied concentrations, diluted in 1% nonfat milk, 0.05% Tween 20 in PBS at 50 ul/well. Following one hour incubation at room temperature, plate washed with PBS plus 0.025% Tween 20 in the Skan Washer 300. A 2000-fold dilution in 1% nonfat milk, 0.05% Tween 20 in PBS of goat anti-human Kappa-HRP (Southern Biotech Cat#2060-05) was added 50 ul/well to detect bound Fab. Plate incubated for 1 hour at room temperature washed with PBS plus 0.025% Tween 20 in the Skan Washer 300. TMB solution (KIRKEGAARD & PERRY LABS, INC. cat: 50-76-00) was added 100 ul/well, and the reaction was stopped with 50 ul/well of 4N H2SO4 (Lab-Chem, Cat#LC25830-0 after two minutes. The absorbance was measured at 450 nm, background 540 nm for TMB using the Molecular Devices plate reader. Data was analyzed using the SOFTMAX PRO software package version 4.3 LS (Molecular Devices Corp.) (FIG. 1).

Results:

This resulted in six Fabs with titratable binding: 71C10, 86C11, 66D05, 76C12, 78F05, and 76B04.

Part III: FACS Analysis

Methods:

The six GPR49 Fabs were diluted 1:20, 1:40, and 1:80 and tested for binding to HEK293E transfected with HA-GPR49 by FACS. Twenty-four to forty-eight hours post-transfection, cells are collected in suspension and incubated on ice with anti-GPR49 antibodies or control IgG. The cells were washed and primary antibodies detected with anti-mouse secondary antibodies conjugated to a fluorescent chromophore. Labeled cells were then sorted by FACS to identify anti-GPR49 antibodies that specifically recognize expression of native cell-surface GPR49 protein.

Figure 2:
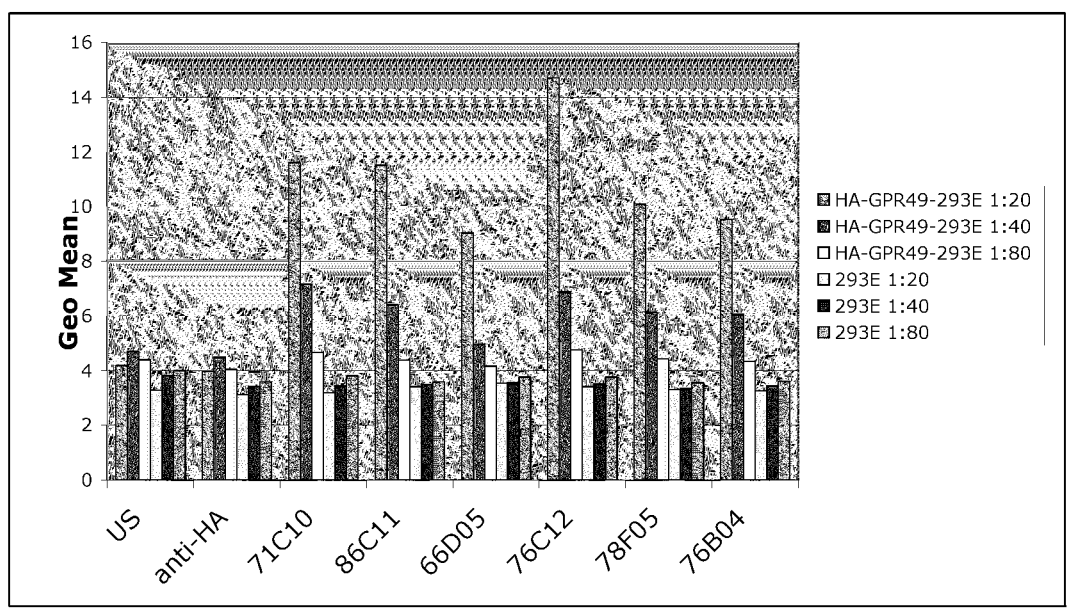
FIG. 2 is a bar graph showing binding of anti-GPR49 Fabs to human GPR49-HA transfected HEK293E cells by FACS.
Figure 3A:
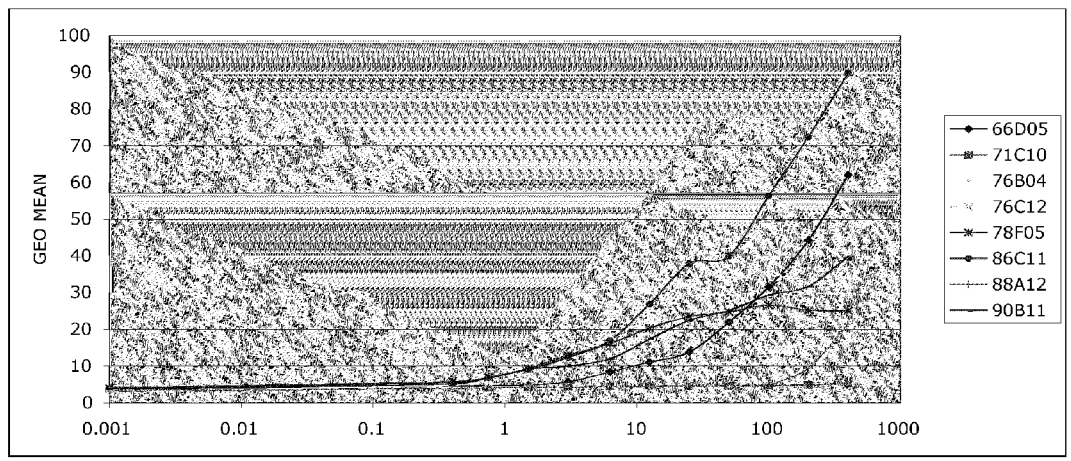
FIGS. 3A and 3B are graphs showing the EC50 values of 3 Dyax Fab candidates on CHO-GPR49 cells (FIG. 3A) or parental CHO cells (FIG. 3B) by FACS binding.
Figure 3B:
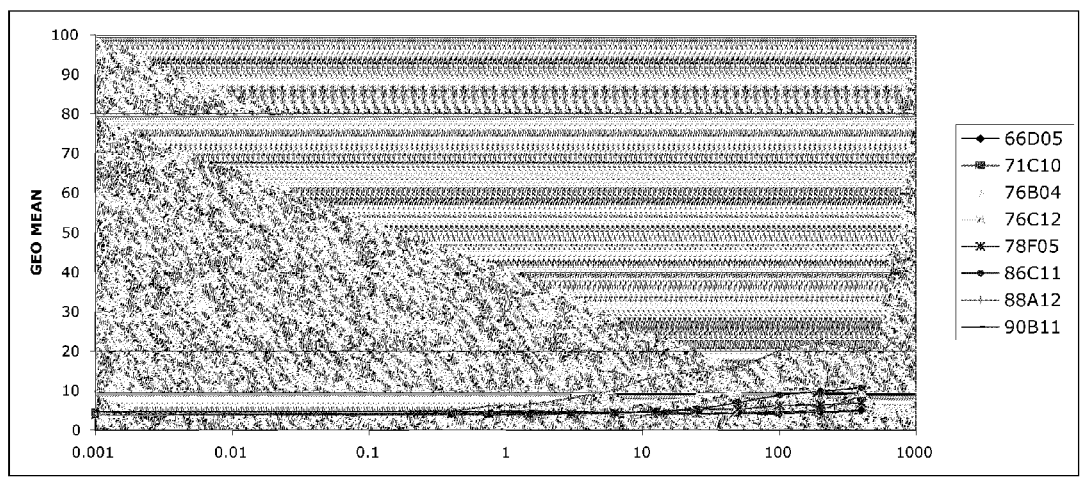
Figure 4A:
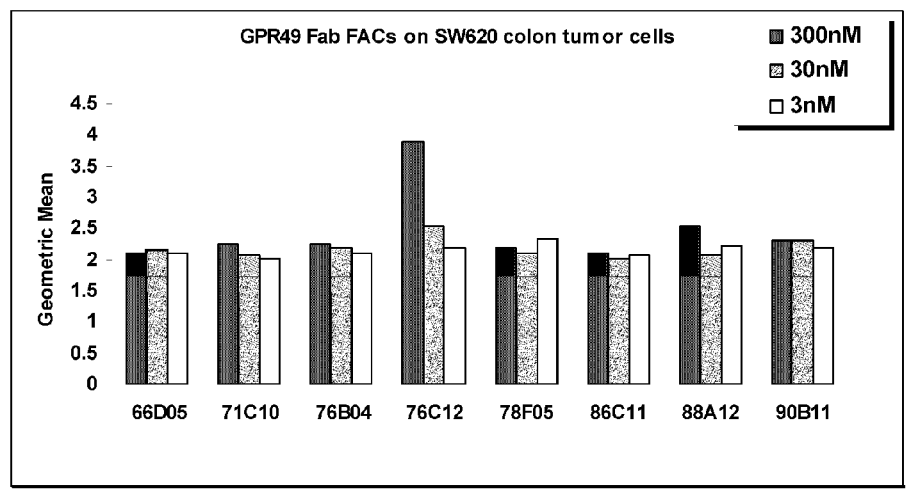
FIGS. 4A and 4B are bar graphs showing binding of GPR49 Fabs to SW620 colon tumor cells as measured by geometric mean (FIG. 4A) or percent positive cells (FIG. 4B).
Figure 4B:
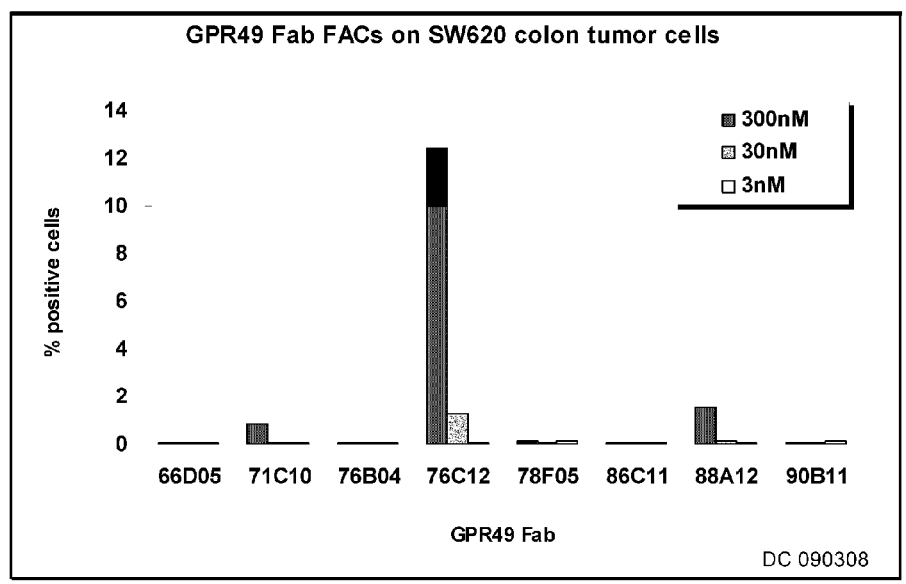
Figure 5A:
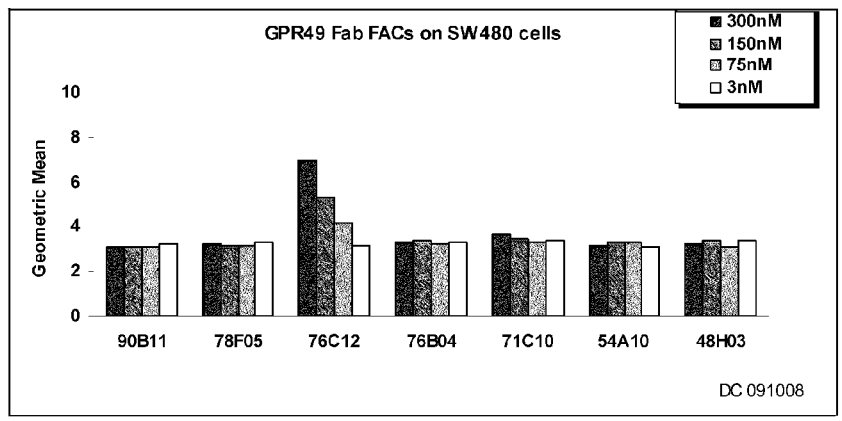
FIG. 5A is a bar graph showing binding of GPR49 Fabs to SW480 colon tumor cells as measured by FACS geometric mean.
Figure 5B:
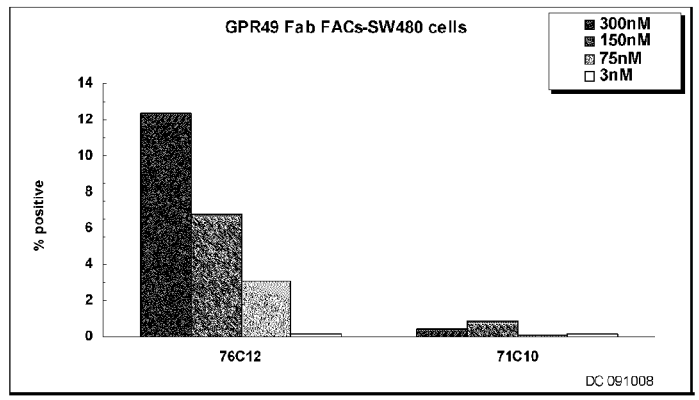
FIG. 5B is a bar graph showing binding of GPR49 Fabs to SW480 colon tumor cells as measured by FACS percent positive cells.
Figure 5C:
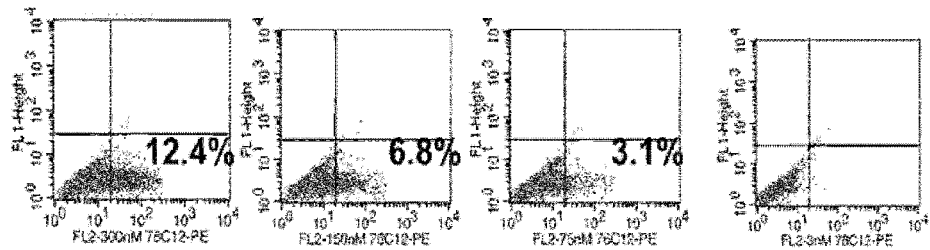
FIG. 5C is a panel of FACS histograms of various concentrations of the 76C12 Fab used to bind SW480 colon tumor cells.
Figure 6A:
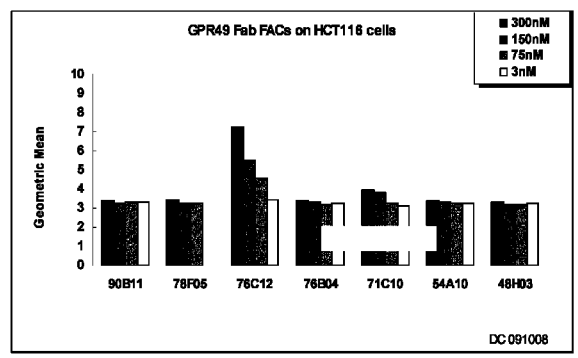
FIG. 6A is a bar graph showing binding of GPR49 Fabs to HCT116 colon tumor cells as measured by FACS geometric mean.
Figure 6B:
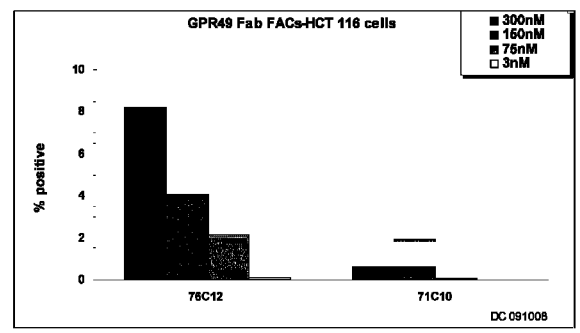
FIG. 6B is a bar graph showing binding of GPR49 Fabs to HCT116 colon tumor cells as measured by FACS percent positive cells.
Figure 6C:
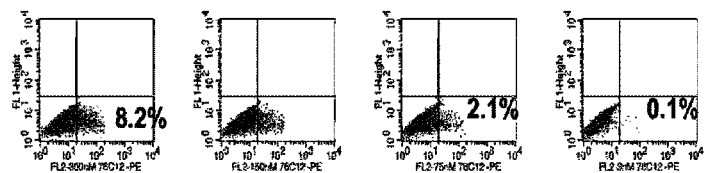
FIG. 6C is a panel of FACS histograms of various concentrations of the 76C12 Fab used to bind HCT116 colon tumor cells.

Results:

All six prospective FACS positive GPR49 Fabs showed a decrease in binding to HA-GPR49-HEK293E with increasing Fab dilution and none showed binding to HEK293E (FIG. 2). Low geometric means may be due to Fab epitopes not being very accessible, low expression of GPR49 on cell surface, or Fabs may be low affinity. Additional testing by FACS of GPR49 Fabs (diluted 2-fold from 400 nM down to zero) on CHO-GPR49 (50 nM MTX) compared to parental CHO revealed three Fabs with approximate EC50<10 nM: 76C12, 76B04, and 78F05 (FIGS. 3A and 3B). Testing of the Fabs against tumor cell lines (SW480, SW620 and HCT116) revealed only Fab 76C12 is capable of binding by FACS (FIGS. 4A, 4B, 5A-C, and 6A-C).

Part IV: Biacore Analysis

Methods:

Three particular Fabs (76C12, 78F05 and 76B04) were identified that specifically bound the human GPR49 receptor with less than 10 nM affinity by FACS. To analyze the binding kinetics, biotinylated anti-human IgG Fc antibody was immobilized on a Biacore SA chip to a level of 2950 RUs. GPR49-Fc was then captured to a density of ~400 RUs in flow cell 2 with flow cell 1 used as a reference. Purified Fabs (100, 50, 25 nM in HSP-EP) were injected at 30 µl/min for 7 minutes with 20 minutes allowed for dissociation. The data were analyzed with BIA evaluation software (v4.1) assuming a 1:1 model. To test the cross reactivity of the Fabs with the Fc domain, IgG1 Fc was then captured to a density of ~250 RUs in flow cell 2 with flow cell 1 used as a reference. All Fabs were then tested under the same conditions as above. All biacore experiments were performed at 25° C. on a BIAcore 3000 instrument.

Results:

Fabs 76C12 and 78F05 bound with $K_D$'s of 3.4 nM and 1.7 nM respectively. Fab 76B04 exhibited weak binding.

Example 3

Construction of Full-Length Anti-GPR49 IgGs

Methods:

Three Fabs were converted to human IgG1 and expressed in CHO cells. DNA sequences encoding three distinct anti-GPR49 Fabs 76C12, 78F05 and 76B04 were selected from a human antibody phage library (Dyax Corp) by biopanning against a recombinant human GPR49 ectodomain-Fc fusion protein. The Fab gene sequences were used to construct expression plasmids encoding full-length antibodies using the pV90AS expression vector system for antibody production in mammalian cells. pV90AS is a modified pV90 expression vector designed to generate two transcripts from a single promoter through alternate splicing of a primary transcript (Reference: USPTO Application WO2005/089285). The natural CMV splice donor is spliced either to a partially impaired splice acceptor to generate an antibody light chain-encoding transcript, or to a natural CMV splice acceptor to generate the antibody heavy chain-coding transcript. The partially impaired splice acceptor has been engineered to result in similar amounts of both heavy and light chain transcripts. Light chain Variable (VL) and Constant (CL) regions were amplified by PCR. The 5' light chain PCR primer included a Sfi I restriction endonuclease site followed by sequence encoding an immunoglobulin light chain signal peptide MDMRVPAQLLGLLLLWLPGARC (SEQ ID NO: 5) in frame to sequences corresponding to the amino-terminus of the VL region according to the methods described in Nakamura T, et al., Int J Immunopharmacol. 22:131-41 (2000), which is incorporated herein by reference in its entirety. The PCR product was purified by agarose gel electrophoresis and extraction using the QIAquick GelExtration kit protocol (QIAGEN CA), digested with restriction endonucleases Sfi I and Asc I and ligated with the Sfi I/Asc I digested pHLP025 vector (Holly Prentice). The pHLP025 vector contains Sfi I/Asc I restriction endonuclease sites for receiving antibody light chain (signal peptide-VL-CL) as a Sfi I/Asc I digested PCR fragment in addition to the natural CMV splice donor site sequence, a partially impaired splice acceptor site sequence, and a poly A signal sequence (Reference: USPTO Application WO2005/089285).

The heavy chain Variable (VH) region of each anti-GPR49 Fab (76C12, 78F05, 76B04) was amplified by PCR. The 5' heavy chain VH PCR included a Nco I restriction endonuclease site followed by sequence encoding synthetic heavy chain signal peptide MGWSLILLFLVAVATRVLS (SEQ ID NO: 6) in frame to sequences corresponding to the aminoterminus of the VH region as described above. The 3' heavy chain VH PCR primer included sequence corresponding to the carboxyl-terminus of the VH region and an Sfi I site. The PCR product was purified by agarose gel electrophoresis and extraction using the QIAquick GelExtration kit protocol (QIAGEN, CA), digested with restriction endonucleases Nco I and Sfi I and ligated with the Nco I/Sfi I digested pHLP029 vector (Holly Prentice). The pHLP029 vector contains Nco I/Sfi I sites for receiving the antibody signal peptide-VH sequence as a Nco I/Sfi I digested PCR fragment in addition to an upstream poly A signal sequence, a natural CMV splice acceptor site sequence, and a downstream poly A signal sequence (Reference: USPTO Application WO2005/089285).

The gene sequences coding for (Sfi I site-light chain signal peptide-anti-GPR49 VL and CL) in pHLP025 and (heavy chain signal peptide-anti-GPR49 VH-Sfi I site) in pHLP029 were assembled into a single DNA fragment by PCR amplification through common overlapping sequences present in both vectors using the 5' light chain and 3' heavy chain VH PCR primers described above. The resulting PCR product was purified by agarose gel electrophoresis and extraction using the QIAquick GelExtration kit protocol (QIAGEN, CA), digested with restriction endonuclease Sfi I and ligated with the Dra III digested IgG1 parental vector.

Results:

The resulting plasmid produces a bi-cistronic precursor transcript that upon alternative splicing results in translationally active antibody heavy and light chain mRNAs in approximately stoichiometric quantities. Correct sequences were confirmed by DNA sequence analysis. Expression of full-length in mammalian cells resulted in production of stable, human IgG1 antibodies.

Example 4

Construction of Full-Length Anti-GPR49 IgGs for Improved Expression in Mammalian Cells To improve antibody expression yields and product quality the original VH gene sequences from anti-GPR49 Fabs 76C12, 78F05, 76B04 were modified.

Methods:

First, anti-GPR49 VH sequences were analyzed for sequences containing putative splice sites with public sequence recognition programs (www.tigr.org/tdb/GeneSplicer/gene_spl.html (The Institute for Genomic Research, 9712 Medical Center Drive, Rockville, Md. 20850), www.fruitfly.org/seq_tools/splice.html). (Martin G. Reese and Frank H. Eeckman, Lawrence Berkeley National Laboratory, Genome Informatics Group, 1 Cyclotron Road, Berkeley, Calif., 94720; see also, Reese M G, Eeckman, F H, Kulp, D, Haussler, D, 1997. "Improved Splice Site Detection in Genie". J Comp Biol 4(3), 311-23.). Second, codons in the heavy chain variable region of the anti-GPR49 Fabs were replaced with codons corresponding to the identical Kabat positions from antibodies that have been successfully expressed in CHO cells without encountering any changes in the original anti-GPR49 VH polypeptide sequence. This second step mostly removes putative splice sites but an additional splice site analysis followed by synonymous codon exchange was performed to reduce the predicted likelihood of a putative splice site being present.

DNA fragments encoding synthetic heavy chain leader in frame with sequence-optimized VH sequences of anti-GPR49Fabs were obtained as chemically synthesized double stranded DNA sequences from a commercial provider (Blue Heron Biotechnology, Inc. Bothell Wash.). The Nco I and Sfi I restriction endonuclease sites at 5' and 3' were included in the synthesized fragments. The leader and anti-GPR49 sequence-optimized VH region fragments were cloned into the Nco I/Sfi I digested the pHLP029 vector as described in Example 3 above. Recombination with the appropriate corresponding light chains in pHLP025 and subsequent cloning of the single fragment is as described in Example 3 above. Correct sequences were confirmed by DNA sequence analysis.

Results:

Expression of full-length antibodies from this plasmid series in mammalian cells results in increased production of stable, human IgG1 antibodies.

Example 5

Transient Expression and Characterization of GPR49 Antibodies

Methods:

Plasmid DNAs were used to transform CHO DG44 cells for transient production of antibody protein. 20 u.g of plasmid DNA was combined with 4×106 cells in a volume of 0.4 mL of 1×PBS. The mixture was added to a 0.4 cm cuvette (Bio-Rad) and placed on ice for 15 min. The cells were electroporated at 600 uF and 350 volts with a Gene Pulser electroporator (BioRad). The cells were placed into a T-25 flask containing CHO-SSFM II media plus 100 uM Hypoxanthine and 16 uM Thymidine and incubated at 37° for 4 days. In addition, plasmid DNA was also used to transfect 293E cells for transient expression of antibody protein. 1.2 u.g of each (heavy and light) plasmid DNA was transfected into 2×106 cells with Qiagen's Effectene Transfection Protocol (Qiagen, CA). Cells were incubated at 37° C. for 3 days.

Results:

Supernatant was harvested and full-length antibody confirmed by both Western Blot and ELISA methods. The ability of full IgG1 to bind to GPR49 was confirmed by ELISA.

Example 6

Development of Anti-GPR49 Antibody Producing CHO Cell Line

This example gives a detailed description of expression of the anti-GPR49 antibody comprising the binding domain of the Fab 76C12 as full-length IgG1. The other Fabs described herein, i.e., those listed in Example 2, were expressed in a similar manner.

Methods:

The variable and constant regions of 76C12 are of human sequence origin. The entire light chain and heavy chain variable regions are derived from a Fab generated against human GPR49 by the DYAX phage display technology. The variable, as well as the light chain constant regions were subcloned into an alternate splice expression vector. The alternate splice configuration links the light and heavy chain through the usage of a single splice donor with two splice acceptors where each splice acceptor generates a transcript encoding one of the two chains. The expression vector DNA encoding the immunoglobulin genes was electroporated into insulin independent Chinese hamster ovary cells (CHO DG44i). A CHO transfectoma was selected for production purposes.

Complementary DNA from the corresponding variable (VL) and constant (CL) domains of the light chain gene of 76C12 and the variable (VH) domain of the heavy chain gene of 76C12 was cloned into an expression vector. The vector contains cloning sites for inserting the entire light chain and variable heavy cDNAs directly upstream of the human heavy chain constant region. In addition to the Ig genes, this expression vector contains a dihydrofolate reductase (DHFR) gene that can be used for selection in mammalian cells. The resulting expression vector was then transfected into CHO cells to initiate the generation of the anti-GPR49 secreting CHO cell lines.

The expression vector was electroporated into CHO cells. Immunoglobulin light chain specific PCR primers were used to PCR amplify the Fab light chain cDNA. The 5' specific oligo sequence included the native signal peptide from the light chain of the Biogen Idec anti-CD23 molecule. The 5' and 3' oligos contain Sfi I and Asc I restriction endonuclease recognition sequences, respectively, for subcloning into an intermediate vector. The VH cDNA was PCR amplified using a 5' oligo that included a synthetic heavy chain signal peptide. The 5' and 3' oligos contain Nco I and Sfi I restriction endonuclease recognition sequences, respectively, for subcloning into an intermediate vector.

Overlapping PCR using the light chain 5' and VH 3' oligos as templates was employed to combine the light chain and the VH region as one cDNA segment. The resultant product was subcloned into the Dra III site thus creating the final alternate splice expression vector. The alternate splice configuration generates two transcripts from a single promoter through alternate splicing of the primary transcript. The natural CMV splice donor is spliced either to a suboptimal splice acceptor to generate a light chain-encoding transcript, or to a natural CMV splice acceptor to generate the heavy chain-coding transcript. The sub-optimal splice acceptor has been designed to generate similar amounts of both transcripts.

The final DNA vector was prepared in HEBS buffer at a concentration of 700 ng/uL prior to electroporation in to CHO cells. Five electroporations were performed using various concentrations of DNA (15, 20, 30, 40, and 45 ug). Each electroporation was done in a disposable 0.4 cm cuvette (Invitrogen) containing 4×106 log phase CHO cells in 0.7 ml sterile HEBS buffer and DNA in 0.1 mL HEBS (0.8 mL total volume). Cells were shocked using a Bio-Rad Gene Pulser XCELL, set at 290 volts, 950 micro Faradays. Shocked cells were then allowed to stand at room temperature for 10 minutes then mixed with 10 mL room temp insulin free CHOM16 medium, centrifuged (3'@ 1000 rpm), and aspirated. Cells were then resuspended in 12 mL insulin free CHOM16 medium (RT) and transferred to a T-75 tissue culture flask.

Cells and Media: prior to electroporation the CHO cells were grown in serum free media (CHOM24) with the addition of 1× nucleosides. CHOM24 is a chemically defined in-house media formulation that does not contain any animal components. Methotrexate selection was performed in nucleoside free CHOM16 and CHOM24 chemically defined media.

Following electroporation, 4×106 CHO cells were pooled into a T-75 flask. Selection for DHFR expression began immediately as the cells were inoculated in nucleoside free medium. Cells were eventually expanded to 125 mL shake flasks in CHOM24 (~3 weeks). To isolate clonal cell lines, the transfected stable pools were diluted and plated at 1 cell/well in 200 uL CHOM16 on four 96-well plates. Plates were maintained at 37° C. until they were screened for antibody titer.

CHO colonies were screened for immunoglobulin production by assaying cell supernatants using an ELISA specific for the human kappa chain (day 21 to day 28 after plating). The capture antibody used in the ELISA was a polyclonal goat anti-human IgG (SouthernBiotech) and the detection antibody was a polyclonal goat anti-human kappa conjugated to horseradish peroxidase (SouthernBiotech). Colonies secreting the highest amount of immunoglobulin were expanded.

Results:
High-expressing CHO cell lines were developed that resulted in anti-GPR49 mAbs with expected biochemical and biophysical properties suitable for scale-up and manufacturing.

Example 7

Purification and Characterization of Fully Human Anti-GPR49 IgG1 Antibodies

The antibody produced in CHO cells were purified and characterized by methods described below.

Methods:
Protein A Capture: A Protein A column was pre-equilibrated with 1×PBS (equilibration buffer) at 100-150 cm/hr with 3 column volumes. Supernatant was loaded at 150 cm/hr with a maximum of 10 mg of GPR49 mAb per milliliter of resin. After loading, the column was washed with 5 column volumes of equilibration buffer. Then, the column was step eluted in an upflow direction with 100 mM Glycine, pH 3.0. Desired fractions were collected and titrated to neutral pH with 2 M Tris base. Collected fractions were dialyzed against 1×PBS and concentrate material to prepare for the size exclusion step. A Size Exclusion aggregate removal step involved equilibration of SUPERDEX 200 with 1×PBS with 1.5 column volumes at a flow rate of 36 cm/hr followed by loading of protein and collecting desired fractions.

Identity testing was performed as follows:
1) Intact mass analysis by mass spectrometry where molecular mass measurements were performed on an electrospray mass spectrometer (ESI-MSD). Prior to analysis, the sample was reduced to remove disulfide bonds. The deconvoluted mass spectrum represents the masses of the heavy and light chains.
2) N-terminal sequence analysis was performed by Edman degradation using an ABI protein sequencer equipped with an on-line PTH analyzer. The sequences for the initial amino acids of the light chain and heavy chain were identified.
3) Peptide mapping with mass spectrometric analysis: tryptic or/and EndoLysC peptide maps were performed to obtain complete sequence coverage by analysis of the LC/MS data generated from each peptide. In addition, determination of sites and amounts of oxidation and deamidation were detected.

Purity testing was performed by; 1) SDS-Page or CE-SDS: Reduced and non-reduced samples, this technique is used to measure antibody fragmentation, aggregation and impurities, 2) SEC-HPLC with LS and RI technique was used to measure aggregation and fragmentation and light scattering determines the molar mass of sample components. 3) SDS gel or capillary IEF method was used to determine the isoelectric focusing pattern and pi distribution of charge isoforms that can result from C- and N-terminal heterogeneity and/or deamidation. Finally, endotoxin concentrations were measured by the Limulus amoebocyte lysate (LAL) kinetic turbidometric method.

Results:
The purification of anti-GPR49 mAbs resulted in greater than 99% monomer, endotoxin free mAbs in gram quantities with properties suitable for scale-up and manufacturing.

Example 8

Production of Mouse Antibodies to Human GPR49 Ectodomain

Part I: Hybridoma Selection
Methods:
To produce antibodies against the ectodomain of GPR49, mice were immunized three times with purified and endotoxin free GPR49-His (SEQ ID NO: 4) using standard techniques. Blood from individual mice was screened for antigen recognition using ELISA and FACS analysis. The animals with the highest antibody titers were then selected for final antigen boost after which spleen cells were isolated for hybridoma production. Approximately 1,000 clones were transferred from 4×24-well fusion plates to 10×96-well culture plates. 199 positive clones were selected by GPR49-Fc capture ELISA, and transferred to 48-well plates. From these, 100 positive clones were not selected because they either showed GPR49-CHO negative or positive binding to parental CHO by FACS. 50 of the 99 positive clones were then selected depending upon isotype.

Results:

36 clones were sub-cloned (single or mixed IgGs bands, such as, IgG1/k, IgG2a/G and IgG1/2b/k). 8 clones lost expression from the parental to subclones. Monoclonal antibodies (mAbs) from 24 selected subclones were purified from the hybridoma supernatant using protein A or protein G agarose chromatography and antibodies were tested by FACS as described below.

Part II: FACS Analysis

Methods:

The 24 murine GPR49 mAbs were serially diluted and tested for binding to CHO transfected with GPR49-Flag-His and parental CHO by FACS (standard methods).

Figure 7A:
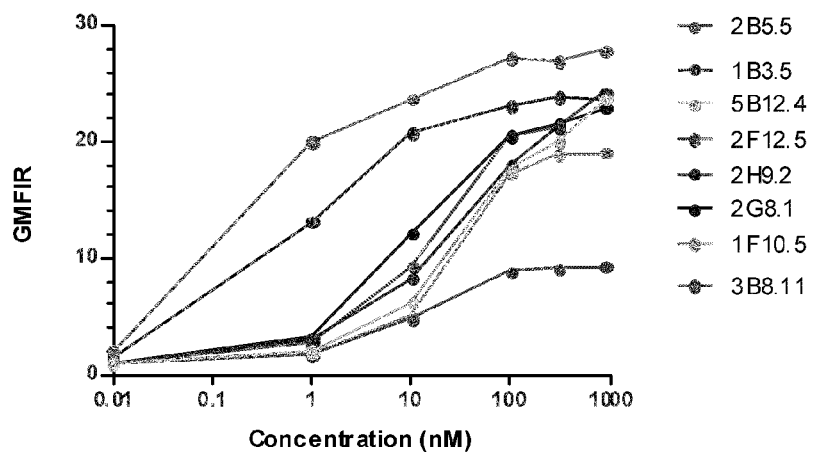
FIGS. 7A-C are graphs showing binding of murine GPR49 antibodies to CHO GPR49-Flag-His expressing cells by FACs.
Figure 7B:
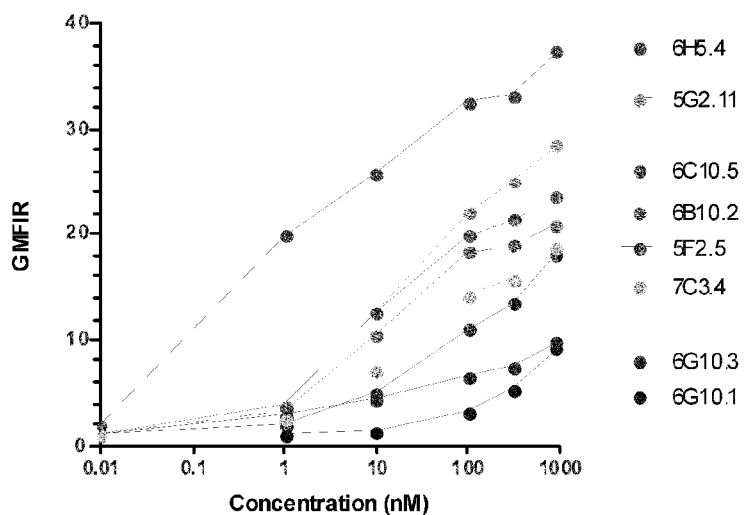
Figure 7C:
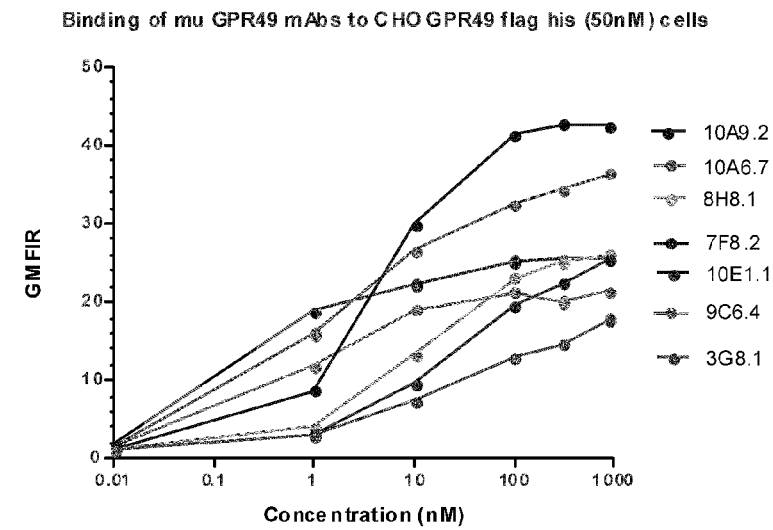

Results:

The results are summarized in Table 2 (data shown in FIGS. 7A-C)

TABLE 2

| GPR49 ms mAb | FACs EC50 (nM) |
| --- | --- |
| 2B5.5 | ~0.2 |
| 7F8.2 | ~0.2 |
| 1B3.5 | 0.8129 |
| 9C6.4 | 0.8297 |
| 6H5.4 | ~1 |
| 10A6.7 | 1.428 |
| 10A9.2 | 4.522 |
| 2G8.1 | 9.766 |
| 6C10.5 | 9.978 |
| 6G10.3 | ~10 |
| 8H8.1 | 11.19 |
| 6B10.2 | 11.2 |
| 3B8.11 | 12.14 |
| 2F12.5 | 14.64 |
| 5G2.11 | 20.94 |
| 1F10.5 | 24.54 |
| 10E1.1 | 29.49 |
| 7C3.4 | 34.51 |
| 2H9.2 | 43.27 |
| 5B12.4 | 43.56 |
| 3G8.1 | 63.83 |
| 5F2.5 | 530.5 |
| 6G10.1 | 2658 |

Part III: Biacore Analysis

The binding kinetics of the mouse mAbs were analyzed by Biacore.

Methods:

Biotinylated anti-human IgG Fc antibody was immobilized on a Biacore SA chip to a level of 2950 RUs. GPR49-Fc was then captured to a density of ~400 RUs in flow cell 2 with flow cell 1 used as a reference. Purified murine mAbs (100, 50, 25 nM in HSP-EP) were injected at 30 µl/min for 7 minutes with 20 minutes allowed for dissociation. The data were analyzed with BIAevaluation software (v4.1) assuming a 1:1 model. All biacore experiments were performed at 25° C. on a BIAcore 3000 instrument.

Results:

Murine mAbs bound to GPR49-Fc with 64 nM to less than 1 nM affinities ($K_D$). Data are shown in Table 3.

TABLE 3

| mAb | BIAcore $K_D$ nM |
| --- | --- |
| 1B3-5 | 1.11 |
| 5B12.4 | 7.52 |
| 6C10.5 | 0.68 |
| 9C6.4 | 1.44 |
| 5G2.11 | 1.59 |
| 6G10_3 | 2.72 |
| 10E1_1 | 3.98 |
| 7F8.2 | 0.91 |
| 10A9.2 | <100pM |
| 6B10_2 | 3.05 |
| 2H9-2 | 0.71 |
| 2G8.1 | N/A |
| 6H5.4 | 0.17 |
| 10A6_7 | <100pM |
| 3B8-11 | 3.92 uM |
| 3G8.1 | 0.99 |
| 7C3_4 | 6.32 |
| 2B5-5 | 1.67 |
| 8H8_1 | 1.54 |
| 2F12.5 | 1.29 |
| 1F10.5 | 64.0 |
| 5F2_5 | 5.52 |
| 6G10.1 | 0.14 |

Example 9

Production of Mouse Antibodies to Full-Length Human GPR49

Part I: Hybridoma Selection

Methods:

To produce antibodies against the full length receptor, mice were immunized three times with 10 ug/mouse of DNA vector encoding the full-length cDNA clone of the GPR49 gene mixed with gold particles. Blood from individual mice was screened approximately 75 days after initial immunization for antigen recognition using ELISA and FACS analysis. The animals with the highest antibody titers were then selected for final antigen boost (25 ug GPR49-Fc, bug GPR49-DNA/gold particle, and $5 \times 10^6$ GPR49-CHO cells) after which spleen cells were isolated for hybridoma production. Approximately 10,000 clones were generated with approximately 200 positive clones were selected by GPR49-CHO capture ELISA.

Results:

67 clones were confirmed by ELISA and GPR49-CHO FACS. 22 of the positive clones were then sub-cloned (single or mixed IgGs bands, such as, IgG1/k, IgG2a/G and IgG1/2b/k). Monoclonal antibodies (mAbs) from 19 selected subclones were purified from the hybridoma supernatant using protein A or protein G agarose chromatography and antibodies were tested by FACS as described below.

Part II: FACS Analysis

Methods:

The 19 murine GPR49 mAbs were serially diluted and tested for binding to CHO transfected with GPR49-Flag-His and parental CHO by FACS (standard methods).

Results:

Murine mAbs bound to GPR49 with 17 nM to less than 1 nM (EC50's). The results are summarized in Table 4 (data shown in FIGS. 8A-D). Antibody 10A9.1 was used as a control.

TABLE 4

| mAb | EC50 (nM, CHO-GPR49) |
|---|---|
| 14H9.1 | 0.9 |
| 12G5.1 | 1.2 |
| 6E10.1 | 1.3 |
| 14F7.1 | 1.5 |
| 4A10.2 | 1.7 |
| 3F11.1 | 1.8 |
| 11F6.1 | 1.9 |
| 5B10.1 | 1.9 |
| 14A8.1 | 2.1 |
| 8E9.1 | 2.2 |
| 9C7.1 | 2.2 |
| 4F6.2 | 2.2 |
| 1B8.1 | 2.2 |
| 18G7.1 | 2.5 |
| 12E3.1 | 2.6 |
| 6H5.1 | 3.0 |
| 2P69.2 | 5.1 |
| 17C9.1 | 12.5 |
| 2H5.1 | 17.5 |
| 10A9.2 | (1st gen mAb) 6.2 |

Part III: GPR49 Direct Binding ELISA

To characterize the binding of the mouse antibodies to GPR49, a direct binding ELISA assay was performed.

Methods:

Soluble GPR49-Fc fusion protein at 2.5 ug/ml in 0.025 M carbonate buffer, pH 9.6 was coated at 50 ul/well in a 96-well (IMMULON2 HB, Dynex Technologies, Inc., Cat. #3455) plate and incubated overnight at 4° C. The plate washed with phosphate-buffered saline (PBS, Irvine Scientific, Cat#9240), pH 7.4 plus 0.025% Tween 20 in the Skan Washer 300 (Skatron Instruments), blocked with buffer containing 1% nonfat milk, 0.05% Tween 20 in PBS, pH 7.4, and then incubated at room temperature for 1 hour. After incubation plate was washed with PBS plus 0.025% Tween 20 in the Skan Washer 300. For the assay, the GPR49-coated plate was next incubated with the control and test antibodies of varied concentrations, diluted in 1% nonfat milk, 0.05% Tween 20 in PBS at 50 ul/well. Following one hour incubation at room temperature, plate washed with PBS plus 0.025% Tween 20 in the Skan Washer 300. A 2000-fold dilution in 1% nonfat milk, 0.05% Tween 20 in PBS of goat anti-mouse-Fc-HRP (Southern Biotech Cat#2060-05) was added 50 ul/well to detect bound Fab. Plate incubated for 1 hour at room temperature washed with PBS plus 0.025% Tween 20 in the Skan Washer 300. TMB solution (KIRKEGAARD & PERRY LABS, INC. cat: 50-76-00) was added 100 ul/well, and the reaction was stopped with 50 ul/well of 4N H2SO4 (Lab-Chem, Cat#LC25830-1) after two minutes. The absorbance was measured at 450 nm, background 540 nm for TMB using the Molecular Devices plate reader. Data was analyzed using the SOFTMAX PRO software package version 4.3 LS (Molecular Devices Corp.) EC50 values were obtained as a result.

Results:

Murine mAbs bound to GPR49-Fc with EC50's in the range of 224 nM to less than 1 nM (Table 5; FIGS. 9A-D).

TABLE 5

| EC50 (ELISA) [nM] | Hybridoma |
|---|---|
| 0.2 | 8E9.1 |
| 0.24 | 11F6.1 |
| 0.25 | 12G5.1 |
| 0.27 | 5B10.1 |
| 0.28 | 6H5.1 |
| 0.38 | 14A8.1 |
| 0.5 | 9C7.1 |
| 0.53 | 4A10.2 |
| 0.55 | 14H9.1 |
| 0.55 | 14E3.1 |
| 0.57 | 14F7.1 |
| 0.65 | 4F6.2 |
| 0.657 | 6E10.1 |
| 0.67 | 2P69.2 |
| 0.88 | 3F11.1 |
| 0.95 | 17C9.1 |
| 1.34 | 1B8.1 |
| 1.35 | 18G7.1 |
| 2.86 | 2H5.1 |
| 225.4 | 18D9.1 |

Example 10

Cancer Tumors can be Sorted with Anti-GPR49 Antibodies

Methods:

The expression of GPR49 in colon and other tumor cells was measured by flow cytometry (FACs) using the anti-GPR49 mAbs 76C12 and 78F05.

Results:

GPR49 was found to be expressed in multiple colon tumors (CT1, CT3, LS174T, Sw480, HCT116, SW620, DLD-1, Lovo), gastric tumor N87, lung tumor A549, and the positive control GPR49-CHO stable transfectants. In addition, the specificity of anti-GPR49 mAb binding to GPR49 was confirmed by RNAi knockdown of GPR49 in LS174T cells, which significantly inhibited the binding of GPR49 mAbs 76C12, 76B04, 78F05 to bind LS174T cells.

Example 11

Validation of GPR49 as a Marker of Colon Cancer Stem Cells (CSC)

The colon tumorsphere assay described in Example 1 was used to determine whether colon tumor cells isolated based on anti-GPR49 mAb binding were enriched for cancer stem cells.

Part I:

Methods:

CT1 primary colon tumor cells maintained in cancer stem cell tumorsphere conditions were sorted by FACs using GPR49 mAbs 76C12. GPR49 positive (GPR49+), GPR49 negative (GPR49−) and unsorted live PI (propidium iodide) negative cells were seeded at 1 cell per well in 96 well plates, and analyzed 3 weeks later for sphere forming ability (i.e. number of cancer stem cells).

Figure 10A:
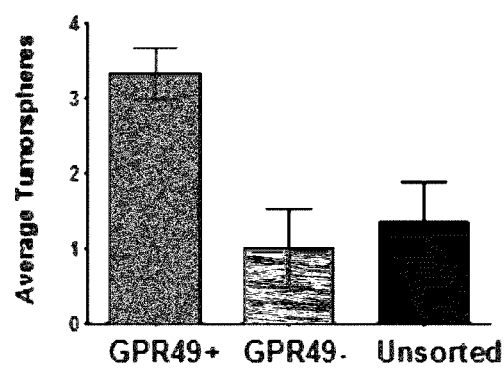
FIGS. 10A and 10B are a bar graph showing the average number of tumorspheres from sorted GPR49+, sorted GPR49−, or unsorted colon tumor cells; and a microscopic image of GPR49+ and GPR49− cells in the tumorsphere assay, respectively.
Figure 10B:
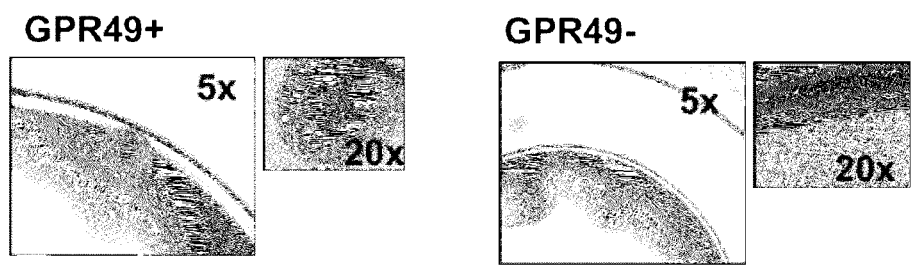

Results:

The sorted GPR49 positive (GPR49+) colon tumor cells were highly enriched for cancer stem cell activity compared to GPR49 negative and unsorted cells (FIGS. 10A and 10B). GPR49 sorted LS174T colon tumor cells were similarly highly enriched for cancer stem cells in 2 separate, independent experiments.

Part II:

Methods:

To further corroborate these results, we performed an additional experiment where colon cancer stem cell tumorspheres were treated with GPR49 or control RNAi-1 and then seeded in 96-well plates at 250 cells per well.

Results:

Treatment with GPR49 RNAi-1 but not control RNAi significantly reduced the number of colon cancer stem cells measured 14 days after treatment.

Example 12

GPR49 Positive Colon Tumor Cells have Cancer Stem Cell Properties In Vivo

Methods:

To show that isolated GPR49+ cells have cancer stem cell properties, in vivo cancer stem cell assays comparing the in vivo growth of GPR49+ versus GPR49− cells were performed. GPR49+ cells from the primary colon tumor line CT1 were sorted with 76C12 using a MoFlo, and implanted at 1000 cells per mouse. Mice were analyzed for tumor formation and weight loss over the next 50 days.

Figure 11A:
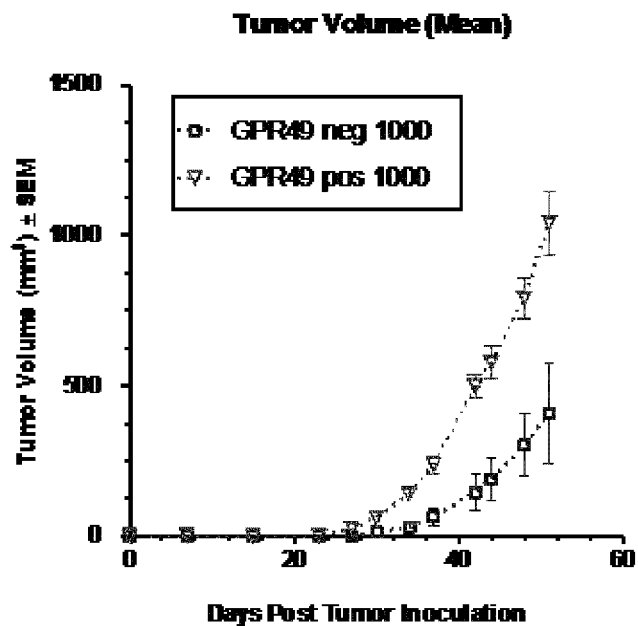
FIGS. 11A and 11B are graphs showing tumor volume (FIG. 11A) and body weight (FIG. 11B) over time of GPR49+ MoFlo sorted colon tumor cells inoculated into mice.
Figure 11B:
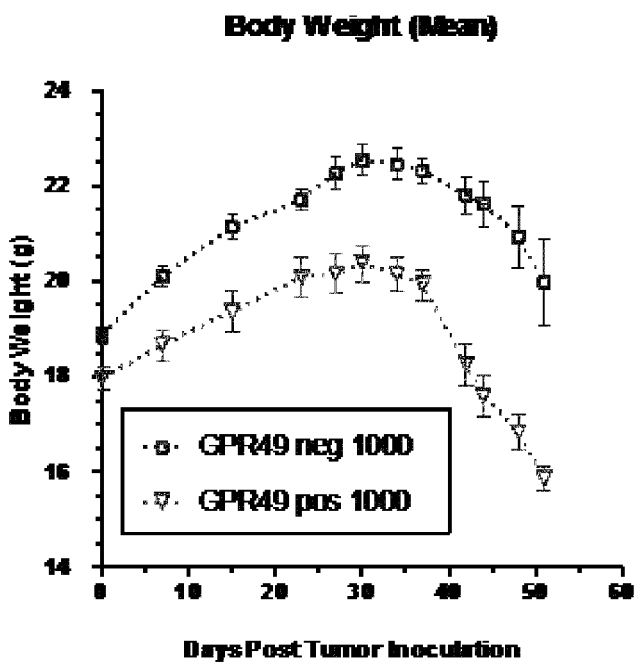

Results:

GPR49+ primary colon tumor cells cause aggressive tumor growth (FIG. 11A) and rapid weight loss (FIG. 11B) in a primary tumor xenograft study. In contrast, GPR49− cells grew very slowly and did not cause rapid weight loss. These findings demonstrate that GPR49 high expressing colon tumor cells are highly tumorigenic, an important feature of cancer stem cells.

Example 13

R-Spondins Bind to GPR49 with High Affinity but do not Activate GPR49-Mediated Signalling Part I: GPR49 is an orphan G protein-coupled receptor (GPCR) related to the glycoprotein hormone receptor family (e.g. receptors for FSH, TSH, LH) and is an intestinal and stomach stem cell marker that was identified by screening Wnt target genes in the gut (Barker et al., Nature, 2007). To identify the natural ligand of GPR49, binding studies were focused on known Wnt-pathway modulators Noggin, Gremlin1, DAN, Chordin-like 1, Cerberus1, PRDC, stanniocalcin-1, COCO, Chordin, R-spondin1-3, BMP2 and BMP4.

Methods:

Ligand binding activity to GPR49-Fc was determined in a biolayer interometry-based assay. In brief, GPR49-Fc and test ligands (all purchased from R& D systems) were all diluted in OB buffer (PBS, pH 7.4, 0.01% (w/v) NaN3, 1 mg/ml BSA, 0.02% (v/v) Tween 20). GPR49-Fc was captured on anti-human IgG Octet tips (ForteBio, Inc., Menlo Park, Calif.; Part#18-5001), using an Octet Red System (ForteBio, Inc., Menlo Park, Calif.). Tips were washed in OB buffer and moved to wells containing test ligand in OB buffer. Binding of test ligand to GPR49-Fc was recorded as biointerferometry signals during an association phase (120 seconds) and dissociation phase (120 seconds). In addition, the ligands were tested against murine GPR49-Fc.

Results:

R-spondin (RSPO) family members interact to human GPR49-Fc, but show a non-specific component that makes interpretation difficult. Specifically, the two-phase association and dissociation observed suggests multiple binding events. RSPO family members do not interact with mouse GPR49-Fc [88% identity (91% similar)].

Part II:

Although the GPR49-Fc used is a dimer of GPR49 ectodomain in solution (due to interacting Fc halves), the bi-phasic binding cannot be explained by this due to the immobilization of the GPR49-Fc to the tip and the monomeric state of the test RSPO molecules. Therefore, the bi-phasic nature of the RPOS binding to GPR49-Fc was further investigated by a solution affinity surface plasmon resonance assay.

Methods:

Binding of RSPO to GPR49 was analyzed using solution affinity surface plasmon resonance (Day ES, et al. Biochemistry. 2005 Feb. 15; 44(6):1919-31.). The method utilizes conditions of so-called "mass-transport-limited" binding, in which the initial rate of ligand binding (protein binding to the sensor chip) is proportional to the concentration of ligand in solution (BIApplications Handbook (1994) Chapter 6: Concentration measurement, pp 6-1-6-10, Pharmacia Biosensor AB). Under these conditions, binding of the soluble analyte (protein flowing over chip surface) to the immobilized protein on the chip is fast compared to the diffusion of the analyte into the dextran matrix on the chip surface. Therefore, the diffusion properties of the analyte and the concentration of analyte in solution flowing over the chip surface determine the rate at which analyte binds to the chip. In this experiment, the concentration of free RSPO-1 in solution is determined by the initial rate of binding to a CM5 Biacore chip containing immobilized GPR49-Fc. Into these RSPO-1 solutions were titrated the competing GPR49-Fc.

Results:

Initial binding rates were obtained from raw sensorgram data. R-spondin-1 showed a bi-phasic binding profile suggesting multiple cooperative binding sites for RSPO on GPR49.

Part III.

To test for the effects of RSPO on GPR49 signaling, multiple assays were utilized.

Methods:

Cyclic AMP, Calcium flux and β-arrestin assays were conducted by standard methods. In addition, a β-catenin/TCF reporter assay which is a transcription-based reporter assay that characterizes the Wnt/beta-catenin signaling pathway. The β-catenin/TCF reporter assay utilized transfected cells with SAbioscience TCF/LEF reporter or negative construct. After 24 hour transfection, cells were counted and aliquoted ($2 \times 10^4$ cells/well) into a 96 well plate. Cells were then starved with Opti-MEM+0.5% FBS+0.1 mM NEAA+1 mM sodium pyruvate+1× antibotic media for 6 hours. Cells were then treated with titrated amount of RSPO and mWnt3a (200 ng/ml) with or without antibody for 18 hours. Dual luciferase activities are developed with Promega dual luciferase kit. In addition, GPR49 RNAi was used to examine the specific contribution of GPR49 to RSPO dependent β-catenin/TCF reporter activity.

Results:

No measurable activity was observed in the cAMP, calcium flux or β-arrestin activity assays for RSPO. However, RSPO drove β-catenin/TCF reporter activity in a dose-dependent manner that was knocked down by GPR49 RNAi.

Example 14

Stimulation of GPR49-3T3 Cells with R-Spondin-1

Methods:

To test the effects of R-spondin on the proliferation of GPR49 overexpressed cells, 2500 NIH 3T3 fibroblast cells stably transfected with GPR49 (GPR49-3T3 clone 50) were incubated with R-spondin 1 for 2 days and the Cell Titer Glo ATP assay used to assess cell proliferation. GPR49-3T3 clone 50 was previously shown to express high levels of cell surface GPR49 by FACs with anti-GPR49 mAb 76C12.

Results:

R-spondin 1 stimulation caused a 25-40% increase in cell proliferation of GPR49-3T3 cells compared to control stimulation with Stanniocalcin in serum free conditions. This result was confirmed in a second independent experiment using a different clone, GPR49-3T3 clone 28, which showed a 4-fold increase in proliferation in response to R-spondin 1 compared to Stanniocalcin control stimulated cells.

Example 15

Inhibition of R-Spondin Binding by GPR49 mAbs

The ability of the anti-GPR49 mAbs detailed in this invention to block RSPO binding to soluble GPR49-Fc was determined.

Methods:

The ligand blocking ability of the anti-GPR49 antibodies was determined by a solution phase competition surface plasmon resonance assay. Briefly, the antibodies (1 uM) co-incubated with 200 nM RSPO for 45 minutes on ice. RSPO alone (200 nM) or in combination with incubated antibodies were then flowed over a CM5 Biacore chip immobilized with GPR49-Fc (as detailed in Example 2). The Rmax, which is the binding signal at the end of the association phase of 60 seconds (Rmax) was used as a measure of the fraction bound at stead state/equilibrium.

Results:

Anti-GPR49 antibodies 3B8.11, 10A6.7, 2B5.5, 6C10.5 all decreased Rmax great than 20%. 3G8.1, 6H5.4 and 7F8.2 all decreased the Rmax by less than 20%.

Example 16

GPR49 mAbs Cross-Reactivity and Specificity to Related Family Members GPR48 (LGR4) and LGR6

Methods:

In order to determine the specificity of the anti-GPR49 antibodies detailed in this invention for related family members, GPR48 (LGR4) and LGR6, recombinant GPR48, GPR49 and LGR6 were independently expressed in mammalian cells (HEK293T). Binding of antibodies to cells overexpressing the receptors was assessed by FACS (standard methods) and compared to cells transfected with control vector (pV100).

Results:

76C12 antibody binds to GPR48 but not to LGR6 expressed in mammalian cells. None of the other antibodies test bind to either GPR48 or LGR6 (Table 6)

TABLE 6

|        | Human GPR48 (LGR4) | Human LGR6 |
|--------|--------------------|------------|
| 76C12  | Y                  | N          |
| 78F05  | N                  | N          |
| 1B8.1  | N                  | N          |
| 14E3.1 | N                  | N          |
| 14A8.1 | N                  | N          |
| 14F7.1 | N                  | N          |
| 18G7.1 | N                  | N          |
| 6H5.4  | N                  | N          |
| 7C3.4  | N                  | N          |
| 7F8.2  | N                  | N          |
| 14H9.1 | N                  | N          |
| 9C7.3  | N                  | N          |
| 1B3.5  | N                  | N          |

Example 17

Internalization of GPR49 by Fully Human Anti-GPR49 Antibodies

Methods:

Lovo cells were seeded at 50,000 cells per well into 8 well chamber slides (Becton Dickinson Collagen Type 1 coated culture slides, BD BioCoat™#354630) 48 hours prior to staining procedures. Cells were routinely maintained below 20 passages. On day of staining procedures, culture media was discarded from each well and replaced with 500 ul cold incubation buffer (MEM Eagle ATCC #30-2003+1% BSA). Cells were washed 2× with this buffer for 3 min each wash. 250 ul of each mAb (76C12, 78F05 and murine 10A9.2) to be tested was then added to the appropriate well at a concentration of 10 ug/ml, diluted in incubation media, and incubated on ice for 1 hour. A human anti-human-IGF-1R antibody was used as a positive control to compare degree of internalization. Antibody 5A7 (anti-Id mAb), IDEC152 (anti-CD23 mAb) and no antibody were used as negative controls. After the 45 minutes incubation on ice, the time zero (t=0') slide washed 3× with 500 ul of cold wash buffer (PBS+1% BSA+ 2% Goat serum) for 3 min each wash (slides always kept on ice). The t=0 slide was then fixed with 500 ul 14% paraformaldehyde (diluted with PBS from 16% stock; EMS #15710) for 15 minutes at room temperature. The t=0 slide was then washed again 3× with cold wash buffer for 3 minutes each wash, then left on ice. Meanwhile, the remaining slides were put into a 37° C. incubator for their designated time points (15 and 60 minutes). At the end of their incubation time each slide followed the same procedures as above-washes and fixation, and put on ice. All slides were then permeabilized with 200 ul cold permeabilization buffer (Wash buffer+0.5% Triton-X) for 10 minutes on ice. All slides were then washed 3× with 500 (×1 cold wash buffer for 3 minutes each wash. The secondary antibody was prepared at a 1:1000 dilution (AlexaFluor 488 Goat-anti-mouse IgG (H+L), Molecular Probes #A11029 for the mAbs and AlexaFluor 488 Goat-anti-human IgG (H+L), Molecular Probes #A11013 for G4 antibodies) in wash buffer, after an initial spin of the stock vial at 10,000 rpm for 10 min at 4° C. 250 ul of the diluted secondary antibody was added to each well and incubated for 40 min at room temperature in the dark (covered). Slides were again washed 3× with 500 ul cold wash buffer. On the final wash, the buffer was discarded and all wells were left empty. The chambers were then disassembled from the slide using the provided disassembly tool, and cover slips were mounted with Vectashield mounting medium containing DAPI (Vector #H-1500, Hard Set™). Slides were stored at 4° C. in the dark overnight to allow the mounting medium to dry. Pictures of the slides were taken with a confocal microscope using the LaserSharp 2000 program (BioRad v5.2) and represented as a merge of blue and green components from Kalman 10 average.

Results:

76C12, 78F05 and 10A9.2 all showed rapid internalization of GPR49 in 60 min. As expected the positive control, IGF1R C06, showed internalized of the IGF1R receptor whereas isotype matched negative controls (mouse 5A7, IDEC152 (primatized anti-CD23 mAb antibody)) did not bind or internalize.

Example 18

GPR49 Antibodies Bind to Murine GPR49

Methods:

In order to determine the specificity of the anti-GPR49 antibodies described herein to murine GPR49, recombinant murine GPR49 was expressed in mammalian cells (HEK293T). Binding of antibodies to cells overexpressing the receptors was assessed by FACS (standard methods) and compared to cells transfected with control vector (pV100).

Results:

76C12 binds to murine GPR49 expressed in mammalian cells with high affinity. Multiple additional GPR49 mAbs bind to murine GPR49 (Table 7).

TABLE 7

|  | murine GPR49 (Lgr5) |
| --- | --- |
| 76C12 | HI |
| 78F05 | LO |
| 1B8.1 | MED |
| 14E3.1 | MED |
| 14A8.1 | MED |
| 14F7.1 | MED |
| 18G7.1 | LO |
| 6H5.4 | LO |
| 7C3.4 | LO |
| 7F8.2 | LO |
| 14H9.1 | LO |
| 9C7.3 | +/− |
| 1B3.5 | +/− |

Example 19

Epitope Grouping of Anti-GPR49 mAbs

An equilibrium binding assay was developed and used to determine common epitope binding groups for the panel of GPR49 antibodies detailed in this invention. Cross-blocking of binding to GPR49 was used to define groups of antibodies that bind to distinct binding epitopes of GPR49.

Methods:

GPR49-Fc binding activity to the test anti-GPR49 mAb was compared to that of GPR49-Fc pre-incubated with secondary test mAb (either self or different mAb) in a biolayer interometry-based assay. Primary anti-GPR49 test mAb (primary mAb) was biotinylated with a Thermo Scientific EZ-Link Sulfo-NHS-Biotin (Thermo Scientific, #21425) according to manufacturer's protocol. Biotinylated primary mAb, GPR49-Fc, and GPR49-Fc plus secondary test anti-GPR49 mAb (secondary mAb) were all diluted in OB buffer (PBS, pH 7.4, 0.01% (w/v) NaN3, 1 mg/ml BSA, 0.02% (v/v) Tween 20). Biotinylated primary mAbs were captured on streptavidin Octet tips (ForteBio, Inc., Menlo Park, Calif.; Part#18-5001), using an Octet Red System (ForteBio, Inc., Menlo Park, Calif.). Tips were washed in OB buffer and moved to wells containing GPR49-Fc in OB buffer. Binding of GPR49-Fc to the primary mAb on the tips was recorded as biointerferometry signals to saturation, during an association phase (120 seconds) and the binding signal at the end of the association phase (Rmax) was used as a measure of the fraction bound at stead state/equilibrium. Binding during the dissociation phase (120 seconds) was also recorded. To measure the cross-blocking ability of the various mAbs to each other, a second binding experiment was performed in which the GPR49-Fc outlined above, was preincubated with a 5 fold molar excess of secondary test mAb (unbiotinylated). This was then bound to the tips pre-load with biotinylated primary mAb to determine the Rmax'. The Rmax' prime was then compared to the Rmax and the percentage of Rmax'/Rmax was calculated to determine the amount of blocking the secondary mAb had on the ability of GPR49-Fc to bind to the primary mAb pre-bound to the tip. Cross-blocking (Rmax'/Rmax×100) of secondary to primary mAbs was recorded as follows: 0-25% full cross-blocking, 25-50% partial cross-blocking, 50-75% low cross blocking, 75-100% no cross-blocking. All mAbs were tested against self (primary and secondary mAb were the same test mAb) to ensure proper analysis.

Results:

Six distinct epitope binding groups were observed for the anti-GPR49 mAbs tested. The groups are: group 1 (76C12, 1B3.5, 6B10.2, 4F6.2), group 2 (18G7.1, 14A8.1, 5B10.1, 14F7.1, 11F6.1, 14E3.1, 1B8.1), group 3 (5F2.5, 6B10.2), group 4 (3F11.1), group 5 (10A.2) and group 6 (6E10.1). Cross-blocking by self-mAbs is shown in Table 8 and 9.

TABLE 8

|  | 18G7.1 | 1B3.5 | 76C12 | 14A8.1 | 5B10.1 | 14F7.1 | 5D6.3 | 5F2.5 |
| --- | --- | --- | --- | --- | --- | --- | --- | --- |
| 18G7.1 | 11 | 100 | 100 | 20 | 28 | 14 | 62 | 100 |
| 1B3.5 | 100 | 4 | 7 | 100 | 100 | 100 | 47 | 100 |
| 76C12 | 100 | 4 | 5 | 100 | 100 | 100 | 25 | 100 |
| 14A8.1 | 5 | 100 | 100 | 6 | 9 | 4 | 99 | 100 |
| 5B10.1 | 13 | 100 | 100 | 16 | 11 | 14 | 76 | 100 |
| 14F7.1 | 7 | 100 | 100 | 7 | 11 | 5 | 100 | 100 |
| 5D6.3 | 100 | 96 | 81 | 100 | 100 | 100 | 66 | 97 |
| 5F2.5 | 100 | 100 | 100 | 100 | 100 | 100 | 79 | 13 |
| 11F6.1 | 9 | 100 | 100 |  |  |  |  | 93 |
| 3F11.1 | 78 | 68 | 100 |  |  |  |  | 100 |
| 14E3.1 | 5 | 88 | 95 |  |  |  |  | 83 |
| 1B8.1 | 6 | 85 | 96 |  |  |  |  | 85 |

TABLE 9

|        | 11F6.1 | 3F11.1 | 14E3.1 | 1B8.1 | 10A9.2 | 6B10.2 | 4F6.2 | 6E10.1 |
|--------|--------|--------|--------|-------|--------|--------|-------|--------|
| 18G7.1 |        |        |        |       |        |        |       |        |
| 1B3.5  |        |        |        |       |        |        |       |        |
| 76C12  |        |        |        |       | 100    | 4      | 6     | 100    |
| 14A8.1 |        |        |        |       |        |        |       |        |
| 5B10.1 |        |        |        |       |        |        |       |        |
| 14F7.1 |        |        |        |       |        |        |       |        |
| 5D6.3  |        |        |        |       |        |        |       |        |
| 5F2.5  |        |        |        |       | 100    | 8      | 100   | 100    |
| 11F6.1 | 4      | 99     | 0      | 1     | 100    | 100    | 100   | 100    |
| 3F11.1 | 100    | 5      | 86     | 75    | 100    | 100    | 100   | 100    |
| 14E3.1 | 4      | 87     | 2      | 0     |        |        |       |        |
| 1B8.1  | 5      | 86     | 2      | 3     |        |        |       |        |

Example 20

GPR49 mAbs Inhibit Growth of Cancer Stem Cells In Vitro

GPR49 mAbs were tested for their ability to inhibit growth of cancer stem cells in a colon cancer stem cell tumorsphere assay.

Figure 12A:
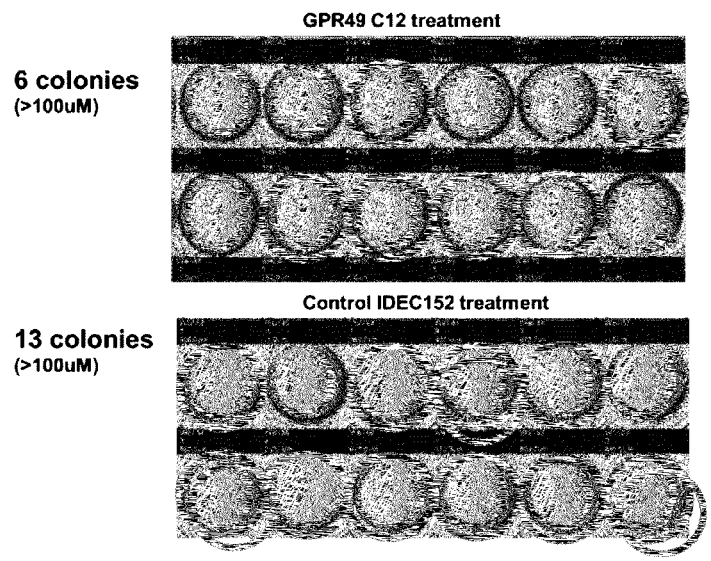
FIGS. 12A and 12B are a picture of colonies formed by cells treated with the 76C12 antibody (upper panel) or control IDEC152 treatment (lower panel) in the tumorsphere assay; and a graph showing percent inhibition of cancer stem cell tumorsphere growth of cells treated with the 78F05 or 76C12 antibodies, respectively.
Figure 12B:
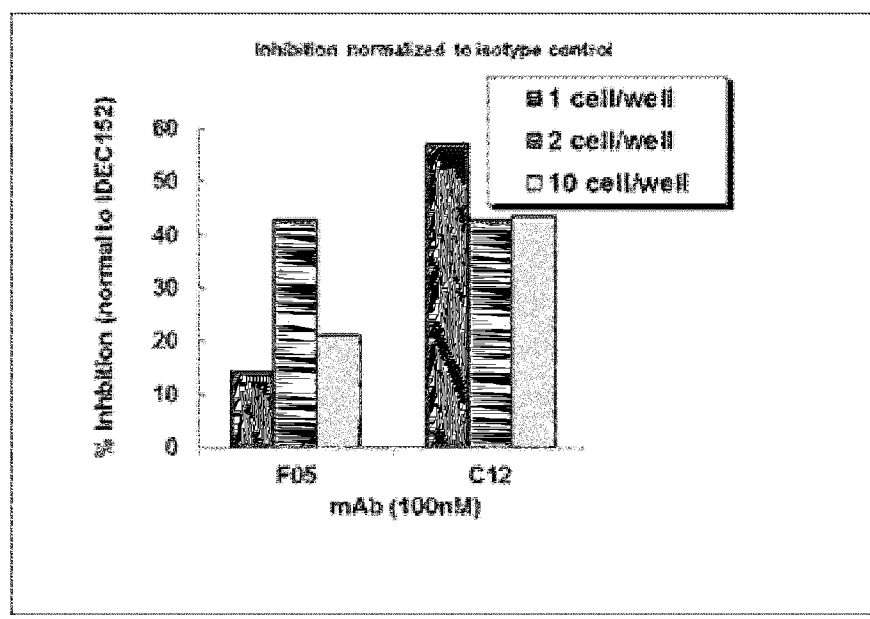

Methods:

Tumorspheres were established as previously described in Example 1, and seeded in the presence of GPR49 mAbs, or control isotype IgG1 at 1-2000 cells per well in ultra-low-attachment plates. In one experiment, test and control mAbs were used to treat CT1 primary colon tumorspheres that were plated at 1, 2 or 10 cells per 96w/plate in cancer stem cell medium (FIGS. 12A and 12B). In addition, a second screen was performed as above but with colon tumorspheres from primary colon tumor cells CT3. CT1 and CT3 are colon tumor cell lines that originated from fresh colon tumor patient biopsy samples, and were used to establish colon cancer stem cell (tumorsphere) lines. They are considered "primary" lines because they are low-passage (<10 passages) derived recently from the patient primary samples. They are considered cancer stem cell lines because they are grown under established cancer stem cell conditions (serum-free medium) and low-attachment plates (cells grow in suspension).

Figure 13:
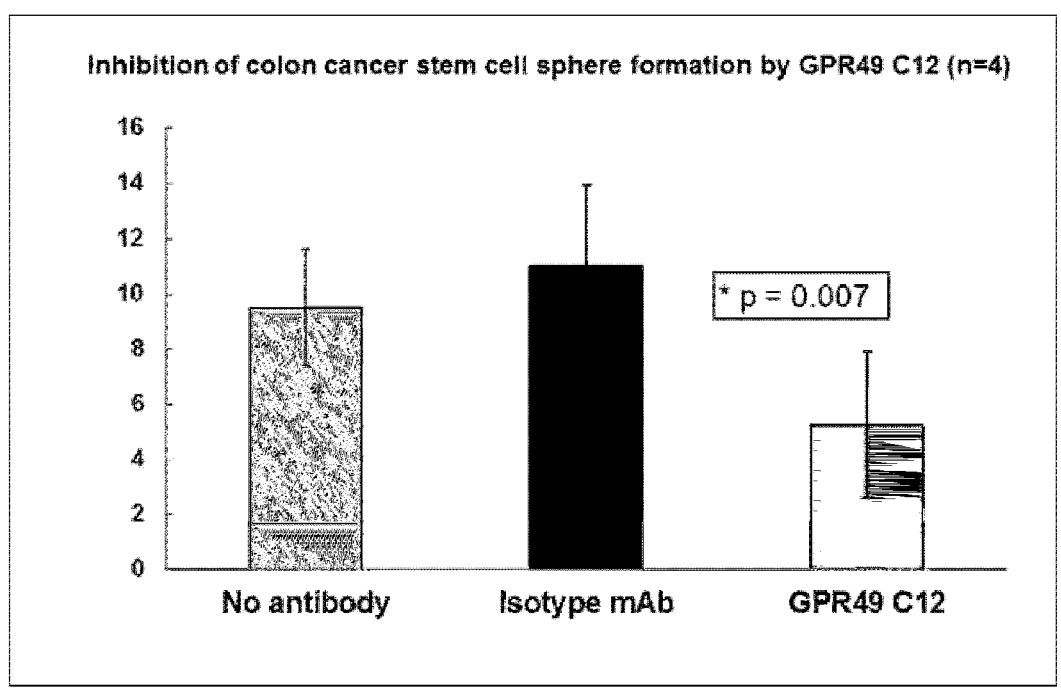
FIG. 13 is a graph showing inhibition of colon cancer stem cell sphere formation by treating cells with no antibody, isotype monoclonal antibody, or the 76C12 antibody.

Results:

76C12 caused an average of 44% growth inhibition (n>10 experiments) and 78F05 caused on average of 37% growth inhibition (4 experiments) in the number of tumorspheres or cancer stem cells (derived from CT1 colon tumor line) after 14 days (FIG. 13). Murine antibodies were also assayed with the tumorsphere assay and resulted in 9 with greater than 20% inhibition of cancer stem cell growth. One human mAb (76B04) and 38 murine anti-GPR49 mAbs showed no inhibition of tumorsphere growth. Data is summarized in Table 10. The top five GPR49 mAbs from above were also tested in a CT3 cancer stem cell (tumorsphere) assay and showed between 52 to 37% growth inhibition (Table 11). Finally, GPR49 mAb 76C12 showed a 27% growth inhibition against cancer stem cells derived from colon tumor cell line DLD1 (average of 5 experiments).

TABLE 10

CT1 Cancer Stem Cell Assay (Tumorsphere) mAb summary

| mAb | CT1 colon tumorsphere inhibition (%) | Antibody type | P value | Data reproducible in (N) experiments |
|-----|-----|-----|-----|-----|
| 76C12 | 44 | Human | p = 0.007 | >10 |
| 18G7.1 | 37 | Mouse 2G | p = 0.008 | 2 |
| 78F05 | 27 | Human | p = 0.04 | 4 |
| 5D6.3 | 30 | Mouse 1st Gen | p = 0.008 | 2 |
| 1B3.5 | 28 | Mouse 1st Gen | p = 0.008 | 3 |
| 14A8.1 | 27 | Mouse 2G | p = 0.02 | 2 |
| 5B10.1 | 24 | Mouse 2G | p = 0.008 | 3 |
| 14F7.1 | 20 | Mouse 2G | p = 0.002 | 3 |
| 5F2.5 | 21 | Mouse 1st Gen | p = 0.04 | 1 |
| 7C3.4 | 20 | Mouse 1st Gen | p = 0 .02 | 1 |
| 8E9.1 | 20 | Mouse 2G | | 2 |

TABLE 11

CT3 Cancer Stem Cell Assay (Tumorsphere) mAb summary

| mAb | CT3 colon tumorsphere inhibition (%) | Antibody type | Data reproducible in (N) experiments |
|-----|-----|-----|-----|
| 76C12 | 52 | Human | 3 |
| 18G7.1 | 42 | Mouse 2G | 3 |
| 78F05 | 37 | Human | 3 |
| 5D6.3 | 37 | Mouse 1st Gen | 3 |
| 1B3.5 | 46 | Mouse 1st Gen | 3 |

Example 21

In Vivo Inhibition of Primary Colon Cancer Tumors Having K-Ras P13K PTEN and p53 Mutations Using GPR49 Antibodies We performed an experiment to determine if GPR49 antibodies were effective in vivo to inhibit colon cancers that had particular mutations that can lead to resistance to known cancer therapies. For example, patients with the KRAS mutation may have a poor response to panitumumab (Vectibix®) and cetuximab (Erbitux®) therapy in colorectal cancer. Thus, we wanted to determine if the GPR49 antibodies could provide a useful treatment for colon cancers with these known therapeutic resistance markers.

Methods:

Single agent in vivo efficacy of murine antibodies 14F7.1, 18G7.1, 5B10.1, 14A8.1, 1B3.5 was evaluated in a primary colon tumor xenograft model system using CT1 primary xenograft cells. CT1 is a primary colorectal cancer (CRC) in vivo xenograft tumor established from a fresh CRC patient tumor sample. The mutational status of the tumor cells was determined by Ion Torrent® (Life Technologies, Carlsbad, Calif.) deep sequencing to identify oncogene mutations. Approximately 5-15% of CT1 tumors express GPR49. SCID beige female mice were inoculated with CT1 tumor cells and monitored for tumor growth. Mice were randomized into groups of 10 when mean tumor volume reached 175 mm$^3$. The antibodies were administered intraperitoneally (i.p.) at 15 mg/kg, twice weekly for 4 weeks. An isotype matched antibody IgG1 was administered as a negative control at 15 mg/kg twice per week for 4 weeks. Tumor volumes and body weights were measured 2×per week.

Figure 14:
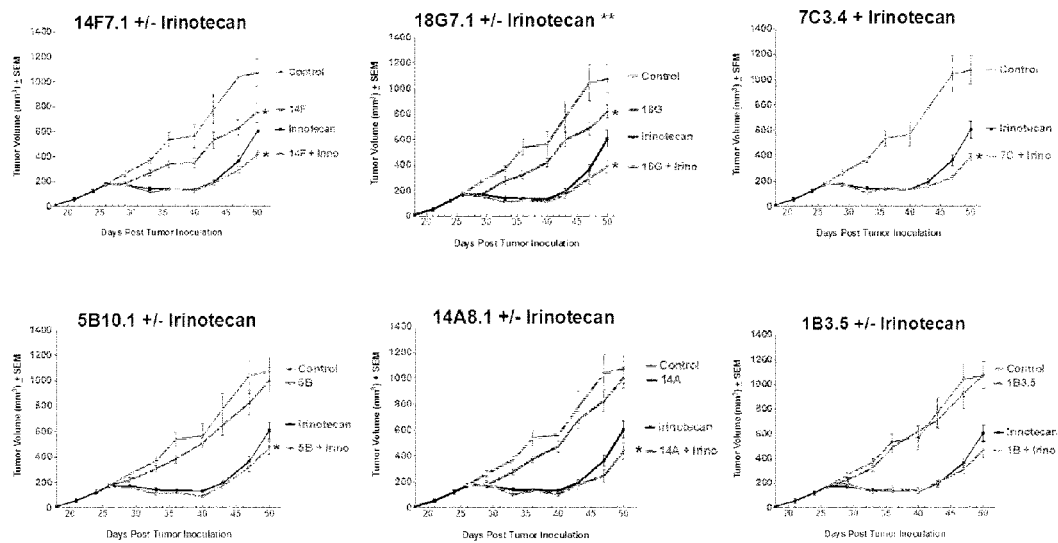
FIG. 14 is a set of graphs showing Tumor Growth Inhibition in a primary colon cancer model having K-Ras, PI3K, PTEN, and p53 mutations
Figure 15:
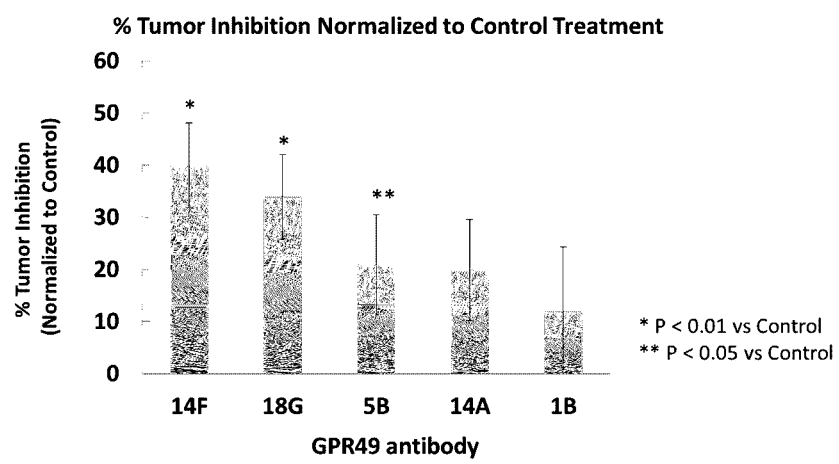
FIG. 15 is a chart showing Percentage Tumor Growth Inhibition.

Results:

The antibodies inhibited tumor growth up to 40% compared to control (FIGS. 14 and 15). Antibodies 14F7 and 18G7 exhibited the highest tumor growth inhibition (40% and 34% tumor inhibition, respectively). The 34% and 40% tumor growth inhibition by the antibodies is an "outsized" effect since GPR49 is only expressed on approximately 5-15% of the tumor cells. This outsized effect suggests that antibody inhibition of GPR49 positive cancer stem cells is targeting the source of the proliferating tumor cells in vivo.

Example 22

In Vivo Inhibition of Primary Colon Tumors Having K-Ras PI3K PTEN and p53 Mutations by GPR49 Antibodies in Combination with the Chemotherapeutic Irinotecan We also performed an experiment to determine if GPR49 antibodies in combination with well-known cancer therapeutic agents would be effective in vivo to inhibit colon cancers that had particular mutations that can lead to resistance to known cancer therapies.

Methods:

Single agent in vivo efficacy of murine antibodies 14F7.1, 18G7.1, 5B10.1, 14A8.1, 1B3.5 was evaluated in a primary colon tumor xenograft model system using CT1 primary xenograft cells. CT1 is a primary colorectal (CRC) in vivo xenograft tumor established from a fresh CRC patient tumor sample. The mutational status was determined by Ion Torrent deep sequencing to identify oncogene mutations. Approximately 5-15% of CT1 tumors express GPR49. SCID beige female mice were inoculated with CT1 tumor cells and monitored for tumor growth. Mice were randomized at day 0 into groups of 10 when mean tumor volume reached 175 mm$^3$. Chemotherapeutic irinotecan was administered IP at 10 mg/kg once per day for the first 5 days. The antibodies were administered intraperitoneally (i.p.) at 15 mg/kg administered twice weekly for 4 weeks. Tumors were measured at the indicated intervals post-inoculation for total tumor volume.

Figure 16:
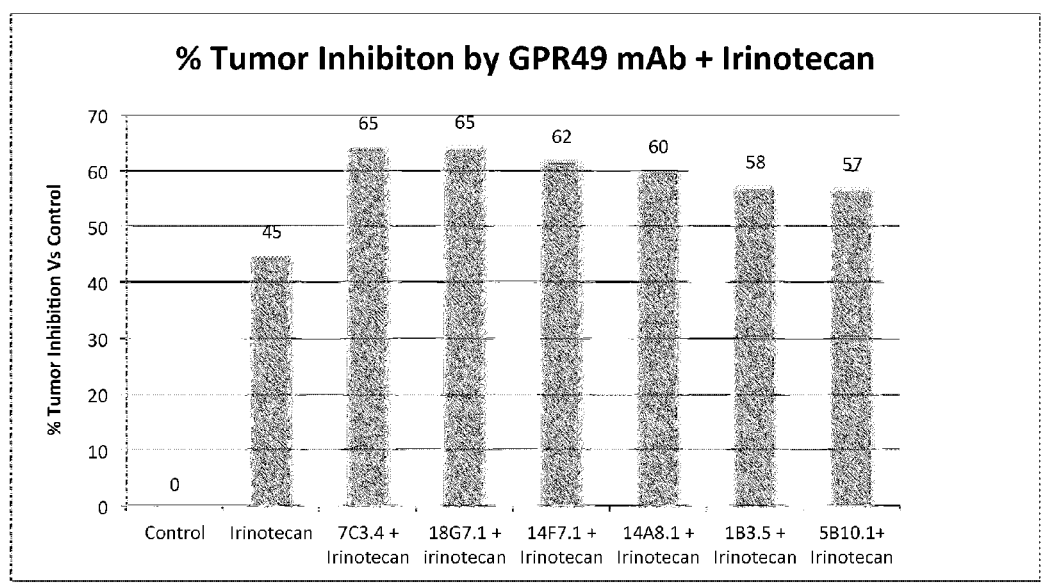
FIG. 16 is a chart showing Percentage Tumor Inhibition by GPR49 mAb+ irinotecan combination treated CRC tumors with K-Ras, PI3K, PTEN, and p53 mutations.

Results:

Anti-GPR49 antibodies in combination with irinotecan inhibited tumor growth by 57% to 65%, compared to 45% tumor inhibition by irinotecan alone (FIG. 14, FIG. 16). GPR49 antibodies therefore enhanced the anti-tumor activity of irinotecan by 27% to 44% in colon cancers known to be resistant to certain available therapeutics.

Example 23

In Vivo Inhibition of Primary Colon Cancer Tumors Having K-Ras PI3K PTEN H-Ras APC TP53 FGFR2 VANGL2 STK11 JAK2 and RB1 Mutations We performed an experiment to determine whether GPR49 antibodies would be effective as single agent inhibitors of colon cancer tumors that had particular mutations that can lead to resistance to known cancer therapies. We had determined, above, that GPR49 antibodies in combination with well-known cancer therapeutic agents were effective. In this experiment we determined the relative inhibition of tumor growth upon treatment with GPR49 antibodies compared to control treatment.

Methods:

Single agent in vivo efficacy of murine antibodies 18G7.1 and 7C3.4 was evaluated in a primary colon tumor xenograft model system using CT3 (primary colon cancer) cells. CT3 is a primary colon tumor xenograft derived from a fresh CRC patient tumor sample, and maintained in vivo at low passage number (p<4). The mutational status was determined by Ion Torrent deep sequencing to identify oncogene mutations. Approximately 15-20% of CT3 tumors express GPR49. CB17-Scid female mice were inoculated with CT3 cells and monitored for tumor growth. Mice were randomized into groups of 10 when mean tumor volume reached 130 mm$^3$ (Day 0). Antibodies were then dosed intraperitoneally (i.p.) at 15 mg/kg twice weekly for 4 weeks. An isotype matched antibody IgG1 was administered as a negative control at 15 mg/kg twice per week for 4 weeks. Tumor volume and body weight was measured twice per week until study completion.

Figure 17:
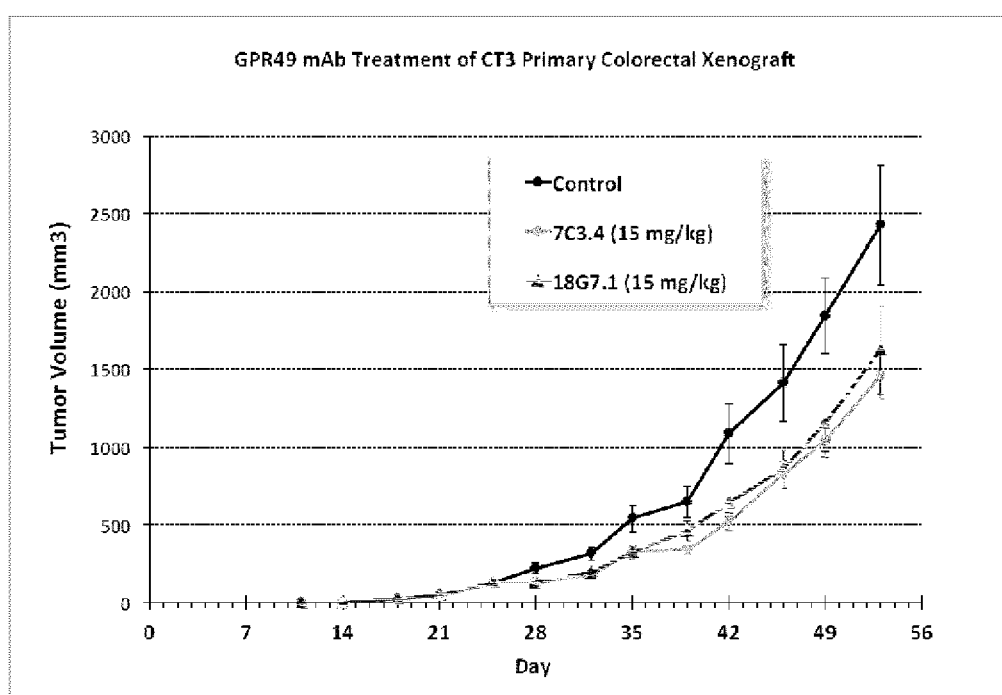
FIG. 17 is a graph showing Tumor Growth Inhibition in primary colon cancer model with K-Ras, PI3K, PTEN, H-Ras, APC, TP53, FGFR2, VANGL2, STK11, JAK2, and RB1 mutations.

Results:

The antibodies inhibited tumor growth up to 43%, compared to control treatment (FIG. 17). This >40% tumor growth inhibition is an "outsized" effect given the GPR49 antibodies only bind to a 15-20% subpopulation of the CT3 tumor cells. This outsized effect suggests that inhibition of GPR49 positive cancer stem cells is targeting the source of the proliferating tumor cells in vivo.

Example 24

GPR49 mAb Treatment Reduces Cancer Stem Cell Frequency In Vivo in Primary Colon Tumors Having K-Ras, PI3K, PTEN, and p53 Mutations We performed an experiment to assay for the impact of GPR49 antibodies on cancer stem cell frequency in cells derived from colon cancer tumors that had particular mutations that can lead to resistance to known cancer therapies. We had observed that GPR49 antibodies demonstrated a relative impact on tumor growth that was 'outsized' in comparison to the proportion of tumor cells bound. This experiment was to determine the effect of these antibodies on cancer stem cell frequency specifically.

Methods:

Isolated CT1 tumor cells from control, GPR49 mAb, irinotecan and GPR49 mAb in combination with irinotecan treatment and control groups from the in vivo studies outlined in Example 1 and 2 were harvested, pooled, dissociated and re-implanted in a limiting dilution secondary transplant assay to measure cancer stem cell frequency. For each treatment group, 8 mice were implanted with 30, 100 and 300 cells. Tumor formation (i.e. tumor take) and growth rate were monitored on a bi-weekly basis for 8 weeks. To calculate the frequency of cancer stem cells in each treatment group, linear regression analysis was performed with Prism GraphPad™ to calculate the frequency of cancer stem cells in each treatment group. This assay is considered the gold-standard for measuring CSCs, because it is a functional CSC assay that measures the frequency of CSC clones in any given tumor that can give rise to a new tumor in a secondary host. In this assay, tumors containing the CSCs to be measured were serially transplanted into secondary recipients in limiting dilution assay.

The assay is thus a functional in vivo measurement of self-renewal capacity, a key component of any stem cell. It does not rely on the as yet incomplete understanding and characterization of cell surface markers or enzyme assays that are often used to measure CSCs in vitro.

Figure 18:
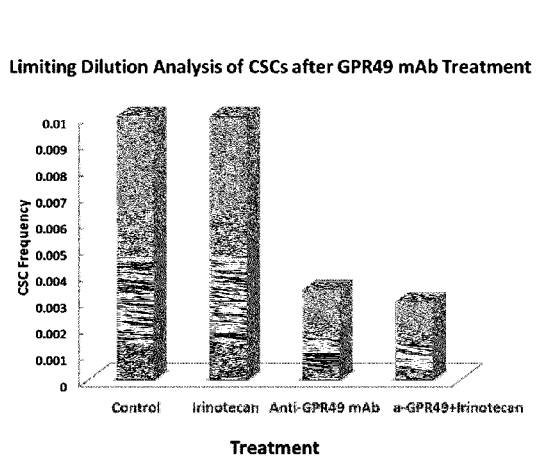
FIG. 18 panel A is a chart showing Anti-GPR49 antibodies reduce cancer stem cell frequency in colon cancer tumors with K-Ras, PI3K, PTEN, and p53 mutations.
Figure 18:
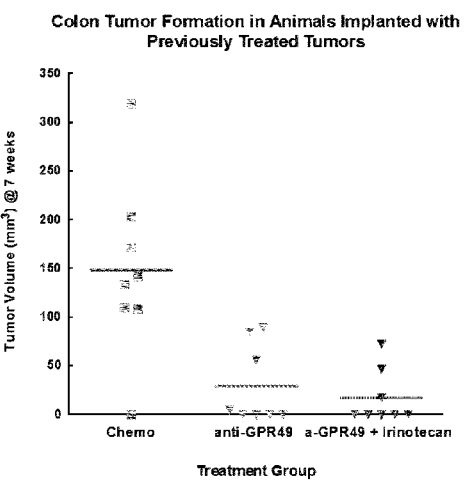

Results:

Tumor re-growth from GPR49 mAb and GPR49 mAb in combination with irinotecan pre-treated tumors was significantly inhibited (FIG. 18). Greater than 62% (5/8) of mice implanted with GPR49 mAb or GPR49 mAb+ irinotecan pre-treated tumors failed to show tumor formation (i.e. were tumor-free) 8 weeks post-transplant. In contrast, only 1/8 mice (13%) implanted with control treated tumors remained tumor-free 8 weeks post-transplant. Linear regression analysis showed a 3 fold reduction in the number of CSCs after GPR49 antibody treatment compared to controls (FIG. 18).

Example 25

GPR49 mAb Treatment Reduces Cancer Stem Cell Frequency In Vivo in Primary Colon Tumors Having K-Ras PI3K PTEN H-Ras APC TP53 FGFR2 VANGL2 STK11 JAK2 and RB1 Mutations We performed an experiment to determine if GPR49 antibodies had a similar impact on cancer cells harboring a larger array of mutations that lead to resistances to known cancer therapies. Expanding on the results above, we determined the effect of these antibodies on cancer stem cell frequency in cancer cell lines harboring a larger number of mutations.

Methods:

Isolated CT3 primary tumor cells from control, GPR49 mAb, irinotecan and GPR49 mAb+ irinotecan treated tumors from the treatment and control groups in the in vivo study outlined in Example 3 were harvested, pooled, dissociated and re-implanted in a limiting dilution secondary transplant assay to measure cancer stem cell frequency. For each treatment group, 8 mice were implanted with 10, 30, 100 cells. Tumor formation and growth rate were monitored on a bi-weekly basis for 12 weeks. To calculate the frequency of cancer stem cells in each treatment group, linear regression analysis was performed with Prism Graph Pad to calculate the frequency of cancer stem cells in each treatment group. This assay is considered the gold-standard for measuring CSCs, because it is a functional CSC assay that measures the frequency of CSC clones in any given tumor that can give rise to a new tumor in a secondary host. In this assay, tumors containing the CSCs to be measured were serially transplanted into secondary recipients in limiting dilution assay. The assay is thus a functional in vivo measurement of self-renewal capacity, a key component of any stem cell. It does not rely on the as yet incomplete understanding and characterization of cell surface markers or enzyme assays that are often used to measure CSCs in vitro.

Figure 19:
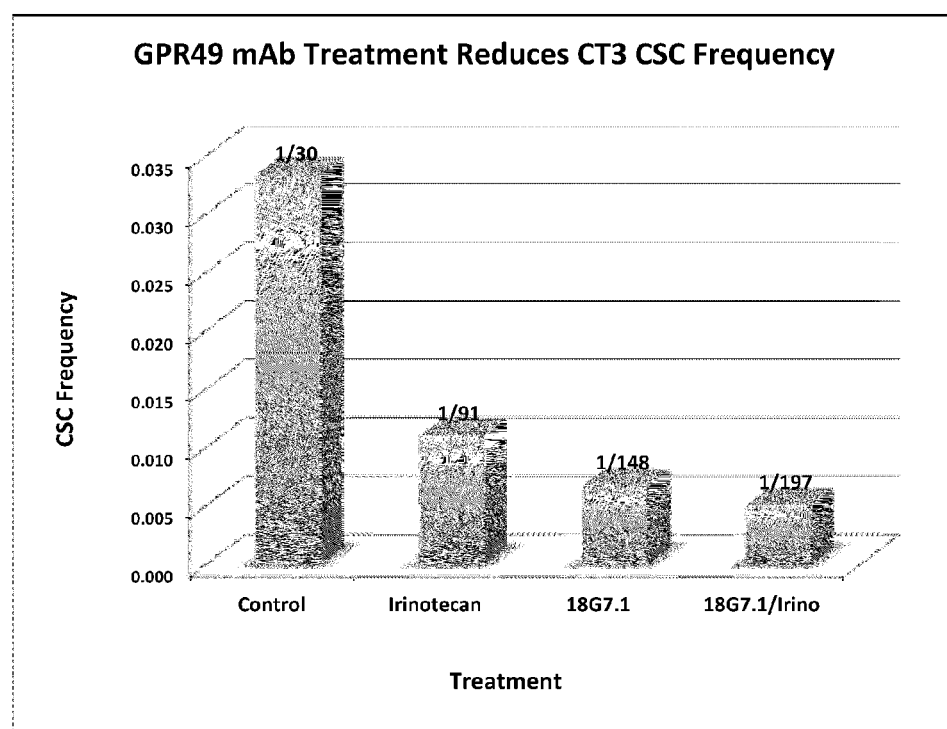
FIG. 19 is a chart showing that GPR49 mAb 18G.7.1 treatment reduces the frequency of cancer stem cells from CRC tumors with K-Ras, PI3K, PTEN, H-Ras, APC, TP53, FGFR2, VANGL2, STK11, JAK2, and RB1 mutations. CSC frequency was measured in a serial re-implantation, limiting dilution assay with primary CRC tumor cells previously treated as indicated.

Results:

GPR49 mAb treatment reduced CSC frequency by 5-fold compared to control (FIG. 19).

Example 26

GPR49 mAb Treatment in Combination with the Chemotherapeutic Irinotecan Prevents Colon Tumor Cells from Forming New Tumors in Secondary Recipients We performed an experiment to determine whether in vivo treatment of colon tumor xenografts with GPR49 mAb in combination with irinotecan would prevent the colon tumor cells from forming new tumors in secondary recipients. New secondary tumor formation in subjects implanted with previously-treated tumor cells is a proxy measurement of the frequency of tumor stem cells in the cancer cell population. We wanted to determine the effect of GPR49 antibodies and irinotecan in combination on secondary tumor formation in subjects receiving colon tumor cells.

Methods:

Isolated tumor cells from control or GPR49 mAb+ irinotecan treated tumors from the in vivo study outlined in Example 3 were harvested, pooled, dissociated and re-implanted in a limiting dilution secondary transplant assay to measure cancer stem cell frequency. For each treatment group, 8 mice were implanted with 10, 30, 100 cells. Tumor formation was monitored on a bi-weekly basis for 12 weeks.

Figure 20:
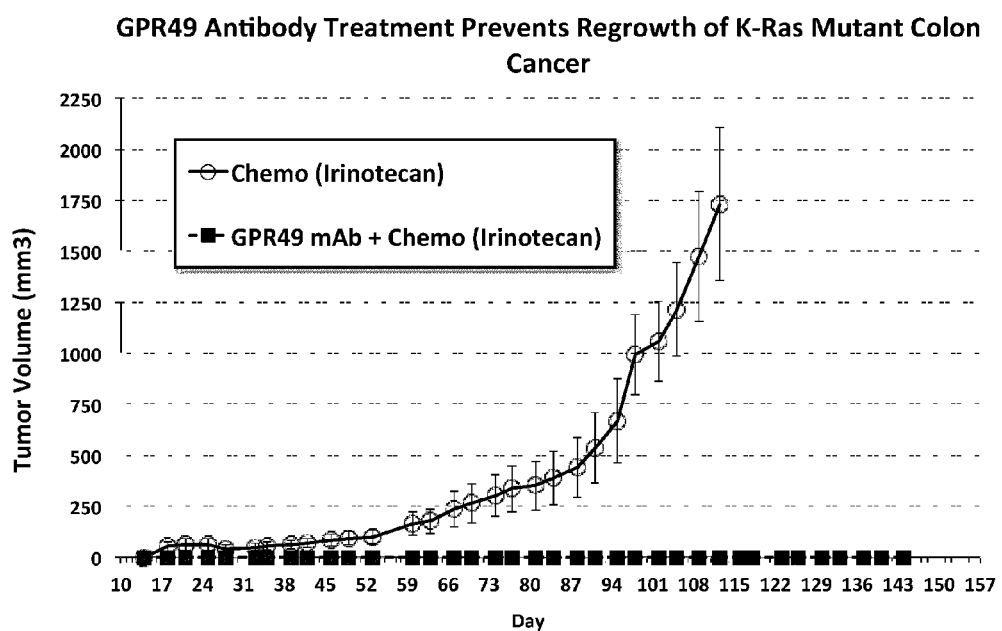
FIG. 20 is a graph showing that Anti-GPR49 antibodies+ irinotecan treatment inhibits the ability of CRC tumors having K-Ras, PI3K, PTEN, H-Ras, APC, TP53, FGFR2, VANGL2, STK11, JAK2, and RB1 mutations to grow upon re-implantation in secondary recipient mice.

Results:

After a 140 day follow-up, no tumor growth was observed from a GPR49 mAb+ irinotecan group (0/8 mice with tumors). In contrast, 5/8 animals implanted with control irinotecan treated mice formed tumors with an average size of 1729 mm$^3$ (FIG. 20). This showed that treatment with GPR49 antibodies destemmed the tumors and greatly reduced the capability of the cancer stem cells to continue proliferating, even after treatment with the GPR49 antibodies was discontinued.

What is claimed:

1. A method of treating a cancer comprising a solid tumor in a mammal, comprising administering to the mammal a therapeutic amount of a monoclonal antibody that binds to G-Protein Coupled Receptor 49 (GPR49) polypeptide and cross-reacts with G-Protein Coupled Receptor 48 (GPR48), wherein the therapeutic amount is sufficient to treat the cancer.

2. The method of claim 1, wherein the antibody does not cross-react with Leucine-rich Repeat Containing G-Protein Coupled Receptor 6 (LGR6) at a $K_d$ of less than $10^{-9}$ M.

3. The method of claim 2, wherein the antibody does not cross-react with LGR6 at a $K_d$ of less than $10^{-6}$ M.

4. The method of claim 3, wherein the antibody does not cross-react with LGR6 at a $K_d$ of less than $10^{-3}$ M.

5. The method of claim 1, wherein the antibody cross-reacts with GPR48 at a $K_d$ of less than $10^{-6}$.

6. The method of claim 5, wherein the antibody cross-reacts with GPR48 at a $K_d$ of less than $10^{-9}$.

7. The method of claim 1, wherein the GPR49 polypeptide has the amino acid sequence of SEQ ID NO: 1.

8. The method of claim 1, wherein the antibody is an IgG class antibody.

9. The method of claim 2, wherein the antibody is an IgG1 class antibody.

10. The method of claim 2, wherein the antibody is a human antibody.

11. The method of claim 2, wherein the antibody is a mouse antibody.

12. The method of claim 1, wherein the antibody binds GPR49 with a $K_d$ of less than $5\times10^{-9}$ M.

13. The method of claim 1, wherein the antibody binds GPR49 with a $K_d$ of less than $10^{-9}$ M.

14. The method of claim 1, wherein the antibody binds GPR49 with a $K_d$ of less than $10^{-10}$ M.

15. The method of claim 1, wherein the antibody binds to GPR49 polypeptide with a $K_d$ of less than $1\times10^{-12}$ M.

16. The method of claim 1, wherein the cancer is colon cancer.

17. The method of claim 1, wherein the cancer comprises colon cancer stem cells.

18. The method of claim 1, further comprising administering irinotecan.

19. The method of claim 1, wherein the cancer comprises a mutation in a gene known to cause cancer selected from the group consisting of K-Ras, PI3K, PTEN, H-Ras, APC, TP53, FGFR2, VANGL2, STK11, JAK2, and RB1.

20. The method of claim 1, wherein the cancer comprises a colon adenocarcinoma.

21. The method of claim 1, wherein the monoclonal antibody specifically binds to a polypeptide comprising SEQ ID NO:03.

22. The method of claim 1, wherein the monoclonal antibody comprises a Fab fragment obtained from an in vitro expression library.

* * * * *

SEQUENCE LISTING

```
<160> NUMBER OF SEQ ID NOS: 6

<210> SEQ ID NO 1
<211> LENGTH: 907
<212> TYPE: PRT
<213> ORGANISM: Homo sapiens

<400> SEQUENCE: 1

Met Asp Thr Ser Arg Leu Gly Val Leu Leu Ser Leu Pro Val Leu Leu
 1               5                  10                  15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
        35                  40                  45

Arg Val Asp Cys Ser Asp Leu Gly Leu Ser Glu Leu Pro Ser Asn Leu
```

```
                50                  55                  60
        Ser Val Phe Thr Ser Tyr Leu Asp Leu Ser Met Asn Ile Ser Gln
        65                  70                  75                  80

Leu Leu Pro Asn Pro Leu Pro Ser Leu Arg Phe Leu Glu Glu Leu Arg
                        85                  90                  95

Leu Ala Gly Asn Ala Leu Thr Tyr Ile Pro Lys Gly Ala Phe Thr Gly
                        100                 105                 110

Leu Tyr Ser Leu Lys Val Leu Met Leu Gln Asn Asn Gln Leu Arg His
                        115                 120                 125

Val Pro Thr Glu Ala Leu Gln Asn Leu Arg Ser Leu Gln Ser Leu Arg
                130                 135                 140

Leu Asp Ala Asn His Ile Ser Tyr Val Pro Pro Ser Cys Phe Ser Gly
        145                 150                 155                 160

Leu His Ser Leu Arg His Leu Trp Leu Asp Asp Asn Ala Leu Thr Glu
                        165                 170                 175

Ile Pro Val Gln Ala Phe Arg Ser Leu Ser Ala Leu Gln Ala Met Thr
                        180                 185                 190

Leu Ala Leu Asn Lys Ile His His Ile Pro Asp Tyr Ala Phe Gly Asn
                        195                 200                 205

Leu Ser Ser Leu Val Val Leu His Leu His Asn Asn Arg Ile His Ser
                210                 215                 220

Leu Gly Lys Lys Cys Phe Asp Gly Leu His Ser Leu Glu Thr Leu Asp
        225                 230                 235                 240

Leu Asn Tyr Asn Asn Leu Asp Glu Phe Pro Thr Ala Ile Arg Thr Leu
                        245                 250                 255

Ser Asn Leu Lys Glu Leu Gly Phe His Ser Asn Asn Ile Arg Ser Ile
                        260                 265                 270

Pro Glu Lys Ala Phe Val Gly Asn Pro Ser Leu Ile Thr Ile His Phe
                        275                 280                 285

Tyr Asp Asn Pro Ile Gln Phe Val Gly Arg Ser Ala Phe Gln His Leu
                290                 295                 300

Pro Glu Leu Arg Thr Leu Thr Leu Asn Gly Ala Ser Gln Ile Thr Glu
        305                 310                 315                 320

Phe Pro Asp Leu Thr Gly Thr Ala Asn Leu Glu Ser Leu Thr Leu Thr
                        325                 330                 335

Gly Ala Gln Ile Ser Ser Leu Pro Gln Thr Val Cys Asn Gln Leu Pro
                        340                 345                 350

Asn Leu Gln Val Leu Asp Leu Ser Tyr Asn Leu Leu Glu Asp Leu Pro
                        355                 360                 365

Ser Phe Ser Val Cys Gln Lys Leu Gln Lys Ile Asp Leu Arg His Asn
                370                 375                 380

Glu Ile Tyr Glu Ile Lys Val Asp Thr Phe Gln Gln Leu Leu Ser Leu
        385                 390                 395                 400

Arg Ser Leu Asn Leu Ala Trp Asn Lys Ile Ala Ile Ile His Pro Asn
                        405                 410                 415

Ala Phe Ser Thr Leu Pro Ser Leu Ile Lys Leu Asp Leu Ser Ser Asn
                        420                 425                 430

Leu Leu Ser Ser Phe Pro Ile Thr Gly Leu His Gly Leu Thr His Leu
                        435                 440                 445

Lys Leu Thr Gly Asn His Ala Leu Gln Ser Leu Ile Ser Ser Glu Asn
                450                 455                 460

Phe Pro Glu Leu Lys Val Ile Glu Met Pro Tyr Ala Tyr Gln Cys Cys
        465                 470                 475                 480
```

```
Ala Phe Gly Val Cys Glu Asn Ala Tyr Lys Ile Ser Asn Gln Trp Asn
                485                 490                 495

Lys Gly Asp Asn Ser Ser Met Asp Asp Leu His Lys Lys Asp Ala Gly
            500                 505                 510

Met Phe Gln Ala Gln Asp Glu Arg Asp Leu Glu Asp Phe Leu Leu Asp
        515                 520                 525

Phe Glu Glu Asp Leu Lys Ala Leu His Ser Val Gln Cys Ser Pro Ser
    530                 535                 540

Pro Gly Pro Phe Lys Pro Cys Glu His Leu Leu Asp Gly Trp Leu Ile
545                 550                 555                 560

Arg Ile Gly Val Trp Thr Ile Ala Val Leu Ala Leu Thr Cys Asn Ala
                565                 570                 575

Leu Val Thr Ser Thr Val Phe Arg Ser Pro Leu Tyr Ile Ser Pro Ile
            580                 585                 590

Lys Leu Leu Ile Gly Val Ile Ala Ala Val Asn Met Leu Thr Gly Val
        595                 600                 605

Ser Ser Ala Val Leu Ala Gly Val Asp Ala Phe Thr Phe Gly Ser Phe
    610                 615                 620

Ala Arg His Gly Ala Trp Trp Glu Asn Gly Val Gly Cys His Val Ile
625                 630                 635                 640

Gly Phe Leu Ser Ile Phe Ala Ser Glu Ser Ser Val Phe Leu Leu Thr
                645                 650                 655

Leu Ala Ala Leu Glu Arg Gly Phe Ser Val Lys Tyr Ser Ala Lys Phe
            660                 665                 670

Glu Thr Lys Ala Pro Phe Ser Ser Leu Lys Val Ile Ile Leu Leu Cys
        675                 680                 685

Ala Leu Leu Ala Leu Thr Met Ala Ala Val Pro Leu Leu Gly Gly Ser
    690                 695                 700

Lys Tyr Gly Ala Ser Pro Leu Cys Leu Pro Leu Pro Phe Gly Glu Pro
705                 710                 715                 720

Ser Thr Met Gly Tyr Met Val Ala Leu Ile Leu Leu Asn Ser Leu Cys
                725                 730                 735

Phe Leu Met Met Thr Ile Ala Tyr Thr Lys Leu Tyr Cys Asn Leu Asp
            740                 745                 750

Lys Gly Asp Leu Glu Asn Ile Trp Asp Cys Ser Met Val Lys His Ile
        755                 760                 765

Ala Leu Leu Leu Phe Thr Asn Cys Ile Leu Asn Cys Pro Val Ala Phe
    770                 775                 780

Leu Ser Phe Ser Ser Leu Ile Asn Leu Thr Phe Ile Ser Pro Glu Val
785                 790                 795                 800

Ile Lys Phe Ile Leu Leu Val Val Val Pro Leu Pro Ala Cys Leu Asn
                805                 810                 815

Pro Leu Leu Tyr Ile Leu Phe Asn Pro His Phe Lys Glu Asp Leu Val
            820                 825                 830

Ser Leu Arg Lys Gln Thr Tyr Val Trp Thr Arg Ser Lys His Pro Ser
        835                 840                 845

Leu Met Ser Ile Asn Ser Asp Asp Val Glu Lys Gln Ser Cys Asp Ser
    850                 855                 860

Thr Gln Ala Leu Val Thr Phe Thr Ser Ser Ile Thr Tyr Asp Leu
865                 870                 875                 880

Pro Pro Ser Ser Val Pro Ser Pro Ala Tyr Pro Val Thr Glu Ser Cys
                885                 890                 895
```

```
                  His Leu Ser Ser Val Ala Phe Val Pro Cys Leu
                              900                 905

<210> SEQ ID NO 2
<211> LENGTH: 2880
<212> TYPE: DNA
<213> ORGANISM: Homo sapiens
<220> FEATURE:
<221> NAME/KEY: CDS
<222> LOCATION: (49)...(2772)

<400> SEQUENCE: 2
tgctgctctc cgcccgcgtc cggctcgtgg cccctactt cgggcacc atg gac acc        57
                                                     Met Asp Thr
                                                       1 tcc cgg ctc ggt gtg ctc ctg tcc ttg cct gtg ctg ctg cag ctg gcg       105
Ser Arg Leu Gly Val Leu Leu Ser Leu Pro Val Leu Leu Gln Leu Ala
      5               10                  15 acc ggg ggc agc tct ccc agg tct ggt gtg ttg ctg agg ggc tgc ccc       153
Thr Gly Gly Ser Ser Pro Arg Ser Gly Val Leu Leu Arg Gly Cys Pro
 20              25                  30                  35 aca cac tgt cat tgc gag ccc gac ggc agg atg ttg ctc agg gtg gac       201
Thr His Cys His Cys Glu Pro Asp Gly Arg Met Leu Leu Arg Val Asp
                 40                  45                  50 tgc tcc gac ctg ggg ctc tcg gag ctg cct tcc aac ctc agc gtc ttc       249
Cys Ser Asp Leu Gly Leu Ser Glu Leu Pro Ser Asn Leu Ser Val Phe
             55                  60                  65 acc tcc tac cta gac ctc agt atg aac aac atc agt cag ctg ctc ccg       297
Thr Ser Tyr Leu Asp Leu Ser Met Asn Asn Ile Ser Gln Leu Leu Pro
         70                  75                  80 aat ccc ctg ccc agt ctc cgc ttc ctg gag gag tta cgt ctt gcg gga       345
Asn Pro Leu Pro Ser Leu Arg Phe Leu Glu Glu Leu Arg Leu Ala Gly
     85                  90                  95 aac gct ctg aca tac att ccc aag gga gca ttc act ggc ctt tac agt       393
Asn Ala Leu Thr Tyr Ile Pro Lys Gly Ala Phe Thr Gly Leu Tyr Ser
100                 105                 110                 115 ctt aaa gtt ctt atg ctg cag aat aat cag cta aga cac gta ccc aca       441
Leu Lys Val Leu Met Leu Gln Asn Asn Gln Leu Arg His Val Pro Thr
                120                 125                 130 gaa gct ctg cag aat ttg cga agc ctt caa tcc ctg cgt ctg gat gct       489
Glu Ala Leu Gln Asn Leu Arg Ser Leu Gln Ser Leu Arg Leu Asp Ala
            135                 140                 145 aac cac atc agc tat gtg ccc cca agc tgt ttc agt ggc ctg cat tcc       537
Asn His Ile Ser Tyr Val Pro Pro Ser Cys Phe Ser Gly Leu His Ser
        150                 155                 160 ctg agg cac ctg tgg ctg gat gac aat gcg tta aca gaa atc ccc gtc       585
Leu Arg His Leu Trp Leu Asp Asp Asn Ala Leu Thr Glu Ile Pro Val
    165                 170                 175 cag gct ttt aga agt tta tcg gca ttg caa gcc atg acc ttg gcc ctg       633
Gln Ala Phe Arg Ser Leu Ser Ala Leu Gln Ala Met Thr Leu Ala Leu
180                 185                 190                 195 aac aaa ata cac cac ata cca gac tat gcc ttt gga aac ctc tcc agc       681
Asn Lys Ile His His Ile Pro Asp Tyr Ala Phe Gly Asn Leu Ser Ser
                200                 205                 210 ttg gta gtt cta cat ctc cat aac aat aga atc cac tcc ctg gga aag       729
Leu Val Val Leu His Leu His Asn Asn Arg Ile His Ser Leu Gly Lys
            215                 220                 225 aaa tgc ttt gat ggg ctc cac agc cta gag act tta gat tta aat tac       777
Lys Cys Phe Asp Gly Leu His Ser Leu Glu Thr Leu Asp Leu Asn Tyr
        230                 235                 240 aat aac ctt gat gaa ttc ccc act gca att agg aca ctc tcc aac ctt       825
```

```
                Asn Asn Leu Asp Glu Phe Pro Thr Ala Ile Arg Thr Leu Ser Asn Leu
                245                 250                 255 aaa gaa cta gga ttt cat agc aac aat atc agg tcg ata cct gag aaa        873
Lys Glu Leu Gly Phe His Ser Asn Asn Ile Arg Ser Ile Pro Glu Lys
260                 265                 270                 275 gca ttt gta ggc aac cct tct ctt att aca ata cat ttc tat gac aat        921
Ala Phe Val Gly Asn Pro Ser Leu Ile Thr Ile His Phe Tyr Asp Asn
                280                 285                 290 ccc atc caa ttt gtt ggg aga tct gct ttt caa cat tta cct gaa cta        969
Pro Ile Gln Phe Val Gly Arg Ser Ala Phe Gln His Leu Pro Glu Leu
                295                 300                 305 aga aca ctg act ctg aat ggt gcc tca caa ata act gaa ttt cct gat       1017
Arg Thr Leu Thr Leu Asn Gly Ala Ser Gln Ile Thr Glu Phe Pro Asp
        310                 315                 320 tta act gga act gca aac ctg gag agt ctg act tta act gga gca cag       1065
Leu Thr Gly Thr Ala Asn Leu Glu Ser Leu Thr Leu Thr Gly Ala Gln
        325                 330                 335 atc tca tct ctt cct caa acc gtc tgc aat cag tta cct aat ctc caa       1113
Ile Ser Ser Leu Pro Gln Thr Val Cys Asn Gln Leu Pro Asn Leu Gln
340                 345                 350                 355 gtg cta gat ctg tct tac aac cta tta gaa gat tta ccc agt ttt tca       1161
Val Leu Asp Leu Ser Tyr Asn Leu Leu Glu Asp Leu Pro Ser Phe Ser
                360                 365                 370 gtc tgc caa aag ctt cag aaa att gac cta aga cat aat gaa atc tac       1209
Val Cys Gln Lys Leu Gln Lys Ile Asp Leu Arg His Asn Glu Ile Tyr
                375                 380                 385 gaa att aaa gtt gac act ttc cag cag ttg ctt agc ctc cga tcg ctg       1257
Glu Ile Lys Val Asp Thr Phe Gln Gln Leu Leu Ser Leu Arg Ser Leu
        390                 395                 400 aat ttg gct tgg aac aaa att gct att att cac ccc aat gca ttt tcc       1305
Asn Leu Ala Trp Asn Lys Ile Ala Ile Ile His Pro Asn Ala Phe Ser
        405                 410                 415 act ttg cca tcc cta ata aag ctg gac cta tcg tcc aac ctc ctg tcg       1353
Thr Leu Pro Ser Leu Ile Lys Leu Asp Leu Ser Ser Asn Leu Leu Ser
420                 425                 430                 435 tct ttt cct ata act ggg tta cat ggt tta act cac tta aaa tta aca       1401
Ser Phe Pro Ile Thr Gly Leu His Gly Leu Thr His Leu Lys Leu Thr
                440                 445                 450 gga aat cat gcc tta cag agc ttg ata tca tct gaa aac ttt cca gaa       1449
Gly Asn His Ala Leu Gln Ser Leu Ile Ser Ser Glu Asn Phe Pro Glu
                455                 460                 465 ctc aag gtt ata gaa atg cct tat gct tac cag tgc tgt gca ttt gga       1497
Leu Lys Val Ile Glu Met Pro Tyr Ala Tyr Gln Cys Cys Ala Phe Gly
        470                 475                 480 gtg tgt gag aat gcc tat aag att tct aat caa tgg aat aaa ggt gac       1545
Val Cys Glu Asn Ala Tyr Lys Ile Ser Asn Gln Trp Asn Lys Gly Asp
485                 490                 495 aac agc agt atg gac gac ctt cat aag aaa gat gct gga atg ttt cag       1593
Asn Ser Ser Met Asp Asp Leu His Lys Lys Asp Ala Gly Met Phe Gln
500                 505                 510                 515 gct caa gat gaa cgt gac ctt gaa gat ttc ctg ctt gac ttt gag gaa       1641
Ala Gln Asp Glu Arg Asp Leu Glu Asp Phe Leu Leu Asp Phe Glu Glu
                520                 525                 530 gac ctg aaa gcc ctt cat tca gtg cag tgt tca cct tcc cca ggc ccc       1689
Asp Leu Lys Ala Leu His Ser Val Gln Cys Ser Pro Ser Pro Gly Pro
                535                 540                 545 ttc aaa ccc tgt gaa cac ctg ctt gat ggc tgg ctg atc aga att gga       1737
Phe Lys Pro Cys Glu His Leu Leu Asp Gly Trp Leu Ile Arg Ile Gly
        550                 555                 560
```

```
                                                        -continued gtg tgg acc ata gca gtt ctg gca ctt act tgt aat gct ttg gtg act       1785
Val Trp Thr Ile Ala Val Leu Ala Leu Thr Cys Asn Ala Leu Val Thr
565                 570                 575 tca aca gtt ttc aga tcc cct ctg tac att tcc ccc att aaa ctg tta       1833
Ser Thr Val Phe Arg Ser Pro Leu Tyr Ile Ser Pro Ile Lys Leu Leu
580                 585                 590                 595 att ggg gtc atc gca gca gtg aac atg ctc acg gga gtc tcc agt gcc       1881
Ile Gly Val Ile Ala Ala Val Asn Met Leu Thr Gly Val Ser Ser Ala
                600                 605                 610 gtg ctg gct ggt gtg gat gcg ttc act ttt ggc agc ttt gca cga cat       1929
Val Leu Ala Gly Val Asp Ala Phe Thr Phe Gly Ser Phe Ala Arg His
            615                 620                 625 ggt gcc tgg tgg gag aat ggg gtt ggt tgc cat gtc att ggt ttt ttg       1977
Gly Ala Trp Trp Glu Asn Gly Val Gly Cys His Val Ile Gly Phe Leu
        630                 635                 640 tcc att ttt gct tca gaa tca tct gtt ttc ctg ctt act ctg gca gcc       2025
Ser Ile Phe Ala Ser Glu Ser Ser Val Phe Leu Leu Thr Leu Ala Ala
    645                 650                 655 ctg gag cgt ggg ttc tct gtg aaa tat tct gca aaa ttt gaa acg aaa       2073
Leu Glu Arg Gly Phe Ser Val Lys Tyr Ser Ala Lys Phe Glu Thr Lys
660                 665                 670                 675 gct cca ttt tct agc ctg aaa gta atc att ttg ctc tgt gcc ctg ctg       2121
Ala Pro Phe Ser Ser Leu Lys Val Ile Ile Leu Leu Cys Ala Leu Leu
                680                 685                 690 gcc ttg acc atg gcc gca gtt ccc ctg ctg ggt ggc agc aag tat ggc       2169
Ala Leu Thr Met Ala Ala Val Pro Leu Leu Gly Gly Ser Lys Tyr Gly
            695                 700                 705 gcc tcc cct ctc tgc ctg cct ttg cct ttt ggg gag ccc agc acc atg       2217
Ala Ser Pro Leu Cys Leu Pro Leu Pro Phe Gly Glu Pro Ser Thr Met
        710                 715                 720 ggc tac atg gtc gct ctc atc ttg ctc aat tcc ctt tgc ttc ctc atg       2265
Gly Tyr Met Val Ala Leu Ile Leu Leu Asn Ser Leu Cys Phe Leu Met
    725                 730                 735 atg acc att gcc tac acc aag ctc tac tgc aat ttg gac aag gga gac       2313
Met Thr Ile Ala Tyr Thr Lys Leu Tyr Cys Asn Leu Asp Lys Gly Asp
740                 745                 750                 755 ctg gag aat att tgg gac tgc tct atg gta aaa cac att gcc ctg ttg       2361
Leu Glu Asn Ile Trp Asp Cys Ser Met Val Lys His Ile Ala Leu Leu
                760                 765                 770 ctc ttc acc aac tgc atc cta aac tgc cct gtg gct ttc ttg tcc ttc       2409
Leu Phe Thr Asn Cys Ile Leu Asn Cys Pro Val Ala Phe Leu Ser Phe
            775                 780                 785 tcc tct tta ata aac ctt aca ttt atc agt cct gaa gta att aag ttt       2457
Ser Ser Leu Ile Asn Leu Thr Phe Ile Ser Pro Glu Val Ile Lys Phe
        790                 795                 800 atc ctt ctg gtg gta gtc cca ctt cct gca tgt ctc aat ccc ctt ctc       2505
Ile Leu Leu Val Val Val Pro Leu Pro Ala Cys Leu Asn Pro Leu Leu
    805                 810                 815 tac atc ttg ttc aat cct cac ttt aag gag gat ctg gtg agc ctg aga       2553
Tyr Ile Leu Phe Asn Pro His Phe Lys Glu Asp Leu Val Ser Leu Arg
820                 825                 830                 835 aag caa acc tac gtc tgg aca aga tca aaa cac cca agc ttg atg tca       2601
Lys Gln Thr Tyr Val Trp Thr Arg Ser Lys His Pro Ser Leu Met Ser
                840                 845                 850 att aac tct gat gat gtc gaa aaa cag tcc tgt gac tca act caa gcc       2649
Ile Asn Ser Asp Asp Val Glu Lys Gln Ser Cys Asp Ser Thr Gln Ala
            855                 860                 865 ttg gta acc ttt acc agc tcc agc atc act tat gac ctg cct ccc agt       2697
Leu Val Thr Phe Thr Ser Ser Ser Ile Thr Tyr Asp Leu Pro Pro Ser
        870                 875                 880
```

```
tcc gtg cca tca cca gct tat cca gtg act gag agc tgc cat ctt tcc    2745
Ser Val Pro Ser Pro Ala Tyr Pro Val Thr Glu Ser Cys His Leu Ser
            885                 890                 895 tct gtg gca ttt gtc cca tgt ctc taa ttaatatgtg aaggaaaatg           2792
Ser Val Ala Phe Val Pro Cys Leu *
900                 905 ttttcaaagg ttgagaacct gaaaatgtga gattgagtat atcagagcag taattaataa   2852
gaagagctga ggtgaaactc ggtttaaa                                      2880

<210> SEQ ID NO 3
<211> LENGTH: 802
<212> TYPE: PRT
<213> ORGANISM: Artificial Sequence
<220> FEATURE:
<223> OTHER INFORMATION: artificially synthesized GPR49-Fc-FLAG protein

<400> SEQUENCE: 3

Met Asp Thr Ser Arg Leu Gly Val Leu Leu Ser Leu Pro Val Leu Leu
 1               5                  10                  15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
        35                  40                  45

Arg Val Asp Cys Ser Asp Leu Gly Leu Ser Glu Leu Pro Ser Asn Leu
 50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
            100                 105                 110

Leu Tyr Ser Leu Lys Val Leu Met Leu Gln Asn Asn Gln Leu Arg His
        115                 120                 125

Val Pro Thr Glu Ala Leu Gln Asn Leu Arg Ser Leu Gln Ser Leu Arg
130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
            180                 185                 190

Leu Ala Leu Asn Lys Ile His His Ile Pro Asp Tyr Ala Phe Gly Asn
        195                 200                 205

Leu Ser Ser Leu Val Val Leu His Leu His Asn Asn Arg Ile His Ser
210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
                245                 250                 255

Ser Asn Leu Lys Glu Leu Gly Phe His Ser Asn Asn Ile Arg Ser Ile
            260                 265                 270

Pro Glu Lys Ala Phe Val Gly Asn Pro Ser Leu Ile Thr Ile His Phe
        275                 280                 285

Tyr Asp Asn Pro Ile Gln Phe Val Gly Arg Ser Ala Phe Gln His Leu
290                 295                 300
```

```
Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
            325                 330                 335

Gly Ala Gln Ile Ser Ser Leu Pro Gln Thr Val Cys Asn Gln Leu Pro
            340                 345                 350

Asn Leu Gln Val Leu Asp Leu Ser Tyr Asn Leu Leu Glu Asp Leu Pro
            355                 360                 365

Ser Phe Ser Val Cys Gln Lys Leu Gln Lys Ile Asp Leu Arg His Asn
    370                 375                 380

Glu Ile Tyr Glu Ile Lys Val Asp Thr Phe Gln Gln Leu Leu Ser Leu
385                 390                 395                 400

Arg Ser Leu Asn Leu Ala Trp Asn Lys Ile Ala Ile His Pro Asn
                405                 410                 415

Ala Phe Ser Thr Leu Pro Ser Leu Ile Lys Leu Asp Leu Ser Ser Asn
            420                 425                 430

Leu Leu Ser Ser Phe Pro Ile Thr Gly Leu His Gly Leu Thr His Leu
        435                 440                 445

Lys Leu Thr Gly Asn His Ala Leu Gln Ser Leu Ile Ser Ser Glu Asn
450                 455                 460

Phe Pro Glu Leu Lys Val Ile Glu Met Pro Tyr Ala Tyr Gln Cys Cys
465                 470                 475                 480

Ala Phe Gly Val Cys Glu Asn Ala Tyr Lys Ile Ser Asn Gln Trp Asn
            485                 490                 495

Lys Gly Asp Asn Ser Ser Met Asp Asp Leu His Lys Lys Asp Ala Gly
            500                 505                 510

Met Phe Gln Ala Gln Asp Glu Arg Asp Leu Glu Asp Phe Leu Leu Asp
        515                 520                 525

Phe Glu Glu Asp Leu Lys Ala Leu His Ser Val Gln Cys Ser Pro Ser
530                 535                 540

Pro Gly Pro Phe Lys Pro Cys Glu His Leu Leu Asp Gly Trp Leu Ile
545                 550                 555                 560

Arg Ile Gly Val Asp Lys Thr His Thr Cys Pro Pro Cys Pro Ala Pro
            565                 570                 575

Glu Leu Leu Gly Gly Pro Ser Val Phe Leu Phe Pro Pro Lys Pro Lys
            580                 585                 590

Asp Thr Leu Met Ile Ser Arg Thr Pro Glu Val Thr Cys Val Val Val
            595                 600                 605

Asp Val Ser His Glu Asp Pro Glu Val Lys Phe Asn Trp Tyr Val Asp
    610                 615                 620

Gly Val Glu Val His Asn Ala Lys Thr Lys Pro Arg Glu Glu Gln Tyr
625                 630                 635                 640

Asn Ser Thr Tyr Arg Val Val Ser Val Leu Thr Val Leu His Gln Asp
            645                 650                 655

Trp Leu Asn Gly Lys Glu Tyr Lys Cys Lys Val Ser Asn Lys Ala Leu
            660                 665                 670

Pro Ala Pro Ile Glu Lys Thr Ile Ser Lys Ala Lys Gly Gln Pro Arg
            675                 680                 685

Glu Pro Gln Val Tyr Thr Leu Pro Pro Ser Arg Asp Glu Leu Thr Lys
        690                 695                 700

Asn Gln Val Ser Leu Thr Cys Leu Val Lys Gly Phe Tyr Pro Ser Asp
705                 710                 715                 720
```

```
Ile Ala Val Glu Trp Glu Ser Asn Gly Gln Pro Glu Asn Asn Tyr Lys
                725                 730                 735

Thr Thr Pro Pro Val Leu Asp Ser Asp Gly Ser Phe Phe Leu Tyr Ser
            740                 745                 750

Lys Leu Thr Val Asp Lys Ser Arg Trp Gln Gln Gly Asn Val Phe Ser
            755                 760                 765

Cys Ser Val Met His Glu Ala Leu His Asn His Tyr Thr Gln Lys Ser
770                 775                 780

Leu Ser Leu Ser Pro Gly Lys Gly Gly Ser Asp Tyr Lys Asp Asp Asp
785                 790                 795                 800

Asp Lys

<210> SEQ ID NO 4
<211> LENGTH: 571
<212> TYPE: PRT
<213> ORGANISM: Artificial Sequence
<220> FEATURE:
<223> OTHER INFORMATION: artificially synthesized GPR49-His protein

<400> SEQUENCE: 4

Met Asp Thr Ser Arg Leu Gly Val Leu Leu Ser Leu Pro Val Leu Leu
1               5                   10                  15

Gln Leu Ala Thr Gly Gly Ser Ser Pro Arg Ser Gly Val Leu Leu Arg
            20                  25                  30

Gly Cys Pro Thr His Cys His Cys Glu Pro Asp Gly Arg Met Leu Leu
        35                  40                  45

Arg Val Asp Cys Ser Asp Leu Gly Leu Ser Glu Leu Pro Ser Asn Leu
    50                  55                  60

Ser Val Phe Thr Ser Tyr Leu Asp Leu Ser Met Asn Asn Ile Ser Gln
65                  70                  75                  80

Leu Leu Pro Asn Pro Leu Pro Ser Leu Arg Phe Leu Glu Glu Leu Arg
                85                  90                  95

Leu Ala Gly Asn Ala Leu Thr Tyr Ile Pro Lys Gly Ala Phe Thr Gly
            100                 105                 110

Leu Tyr Ser Leu Lys Val Leu Met Leu Gln Asn Asn Gln Leu Arg His
        115                 120                 125

Val Pro Thr Glu Ala Leu Gln Asn Leu Arg Ser Leu Gln Ser Leu Arg
    130                 135                 140

Leu Asp Ala Asn His Ile Ser Tyr Val Pro Pro Ser Cys Phe Ser Gly
145                 150                 155                 160

Leu His Ser Leu Arg His Leu Trp Leu Asp Asp Asn Ala Leu Thr Glu
                165                 170                 175

Ile Pro Val Gln Ala Phe Arg Ser Leu Ser Ala Leu Gln Ala Met Thr
            180                 185                 190

Leu Ala Leu Asn Lys Ile His His Ile Pro Asp Tyr Ala Phe Gly Asn
        195                 200                 205

Leu Ser Ser Leu Val Val Leu His Leu His Asn Asn Arg Ile His Ser
    210                 215                 220

Leu Gly Lys Lys Cys Phe Asp Gly Leu His Ser Leu Glu Thr Leu Asp
225                 230                 235                 240

Leu Asn Tyr Asn Asn Leu Asp Glu Phe Pro Thr Ala Ile Arg Thr Leu
                245                 250                 255

Ser Asn Leu Lys Glu Leu Gly Phe His Ser Asn Asn Ile Arg Ser Ile
            260                 265                 270

Pro Glu Lys Ala Phe Val Gly Asn Pro Ser Leu Ile Thr Ile His Phe
```

275                 280                 285
Tyr Asp Asn Pro Ile Gln Phe Val Gly Arg Ser Ala Phe Gln His Leu
        290                 295                 300

Pro Glu Leu Arg Thr Leu Thr Leu Asn Gly Ala Ser Gln Ile Thr Glu
305                 310                 315                 320

Phe Pro Asp Leu Thr Gly Thr Ala Asn Leu Glu Ser Leu Thr Leu Thr
                325                 330                 335

Gly Ala Gln Ile Ser Ser Leu Pro Gln Thr Val Cys Asn Gln Leu Pro
            340                 345                 350

Asn Leu Gln Val Leu Asp Leu Ser Tyr Asn Leu Leu Glu Asp Leu Pro
        355                 360                 365

Ser Phe Ser Val Cys Gln Lys Leu Gln Lys Ile Asp Leu Arg His Asn
370                 375                 380

Glu Ile Tyr Glu Ile Lys Val Asp Thr Phe Gln Gln Leu Leu Ser Leu
385                 390                 395                 400

Arg Ser Leu Asn Leu Ala Trp Asn Lys Ile Ala Ile Ile His Pro Asn
                405                 410                 415

Ala Phe Ser Thr Leu Pro Ser Leu Ile Lys Leu Asp Leu Ser Ser Asn
            420                 425                 430

Leu Leu Ser Ser Phe Pro Ile Thr Gly Leu His Gly Leu Thr His Leu
        435                 440                 445

Lys Leu Thr Gly Asn His Ala Leu Gln Ser Leu Ile Ser Ser Glu Asn
450                 455                 460

Phe Pro Glu Leu Lys Val Ile Glu Met Pro Tyr Ala Tyr Gln Cys Cys
465                 470                 475                 480

Ala Phe Gly Val Cys Glu Asn Ala Tyr Lys Ile Ser Asn Gln Trp Asn
                485                 490                 495

Lys Gly Asp Asn Ser Ser Met Asp Asp Leu His Lys Lys Asp Ala Gly
            500                 505                 510

Met Phe Gln Ala Gln Asp Glu Arg Asp Leu Glu Asp Phe Leu Leu Asp
        515                 520                 525

Phe Glu Glu Asp Leu Lys Ala Leu His Ser Val Gln Cys Ser Pro Ser
530                 535                 540

Pro Gly Pro Phe Lys Pro Cys Glu His Leu Leu Asp Gly Trp Leu Ile
545                 550                 555                 560

Arg Ile Gly Gly Gly His His His His His
                565                 570

<210> SEQ ID NO 5
<211> LENGTH: 22
<212> TYPE: PRT
<213> ORGANISM: Artificial Sequence
<220> FEATURE:
<223> OTHER INFORMATION: artificially synthesized protein

<400> SEQUENCE: 5

Met Asp Met Arg Val Pro Ala Gln Leu Leu Gly Leu Leu Leu Leu Trp
1               5                   10                  15

Leu Pro Gly Ala Arg Cys
            20

<210> SEQ ID NO 6
<211> LENGTH: 19
<212> TYPE: PRT
<213> ORGANISM: Artificial Sequence
<220> FEATURE:
<223> OTHER INFORMATION: artificially synthesized protein

```
<400> SEQUENCE: 6

Met Gly Trp Ser Leu Ile Leu Leu Phe Leu Val Ala Val Ala Thr Arg
 1               5                  10                  15

Val Leu Ser
```